United States Patent
Johnson et al.

(10) Patent No.: US 10,912,770 B2
(45) Date of Patent: Feb. 9, 2021

(54) TARGETING AMP DEAMINASE 2 FOR AMELIORATING CRAVING FOR SUGAR AND OTHER SUBSTANCES

(71) Applicant: The Regents of the University of Colorado, a body coporate, Denver, CO (US)

(72) Inventors: Richard J Johnson, Centennial, CO (US); Ana Andres Hernando, Denver, CO (US); Miguel A Lanaspa Garcia, Denver, CO (US)

(73) Assignee: Regents of the University of Colorado, A Body Corporate, Denver, CO (US)

( * ) Notice: Subject to any disclaimer, the term of this patent is extended or adjusted under 35 U.S.C. 154(b) by 0 days.

(21) Appl. No.: 16/093,196

(22) PCT Filed: Apr. 12, 2017

(86) PCT No.: PCT/US2017/027207
§ 371 (c)(1),
(2) Date: Oct. 12, 2018

(87) PCT Pub. No.: WO2017/180743
PCT Pub. Date: Oct. 19, 2017

(65) Prior Publication Data
US 2019/0117642 A1    Apr. 25, 2019

Related U.S. Application Data

(60) Provisional application No. 62/321,348, filed on Apr. 12, 2016.

(51) Int. Cl.
| | |
|---|---|
| *A61K 31/4725* | (2006.01) |
| *A61K 31/713* | (2006.01) |
| *A61K 45/06* | (2006.01) |
| *A61K 31/4418* | (2006.01) |
| *A61K 31/426* | (2006.01) |
| *A61K 31/455* | (2006.01) |
| *A61K 31/472* | (2006.01) |
| *C12N 15/113* | (2010.01) |

(52) U.S. Cl.
CPC ........ *A61K 31/4725* (2013.01); *A61K 31/426* (2013.01); *A61K 31/4418* (2013.01); *A61K 31/455* (2013.01); *A61K 31/472* (2013.01); *A61K 31/713* (2013.01); *A61K 45/06* (2013.01); *C12N 15/1137* (2013.01); *C12Y 305/04006* (2013.01); *C12N 2310/11* (2013.01); *C12N 2310/12* (2013.01); *C12N 2310/14* (2013.01); *C12N 2310/315* (2013.01); *C12N 2310/3233* (2013.01); *C12N 2310/531* (2013.01)

(58) Field of Classification Search
None
See application file for complete search history.

(56) References Cited

U.S. PATENT DOCUMENTS

| 8,697,628 B2 | 4/2014 | Garcia et al. | |
|---|---|---|---|
| 2013/0209484 A1* | 8/2013 | Garcia .................. | A61K 31/05 424/158.1 |
| 2013/0224218 A1 | 8/2013 | Johnson et al. | |

FOREIGN PATENT DOCUMENTS

| EP | 745684 | 12/1996 |
|---|---|---|
| WO | 2001/07413 | 2/2001 |
| WO | 2017/180743 | 10/2017 |

OTHER PUBLICATIONS

International Search Report and Written Opinion for PCT Application PCT/US17/027207 dated Aug. 8, 2017, pp. 1-19.
Admyre T., et al., "Inhibition of AMP Deaminase Activity Does Not Improve Glucose Control in Rodent Models of Insulin Resistance or Diabetes", Chemistry & Biology 21, 1486-1496, Nov. 20, 2014.
Avena NM, et al, "After daily bingeing on a sucrose solution, food deprivation induces anxiety and accumbens dopamine/acetylcholine imbalance", Physiol Behav. 2008;94(3):309-15.
Avena NM, et al, "Evidence for sugar addiction: behavioral and neurochemical effects of intermittent, excessive sugar intake", Neurosci Biobehav Rev. 2008;32(1):20-39.
Blumenthal DM, Gold MS, "Neurobiology of food addiction", Curr Opin Clin Nutr Metab Care. 2010;13(4):359-65.
Cicerchi C, et al, "Uric acid-dependent inhibition of AMP kinase induces hepatic glucose production in diabetes and starvation: evolutionary implications of the uricase loss in hominids", FASEB journal : official publication of the Federation of American Societies for Experimental Biology. 2014;28(8):3339-50.
Colantuoni C, et al, "Evidence that intermittent, excessive sugar intake causes endogenous opioid dependence", Obes. Res. 2002;10(6):478-88.
De Araujo IE, et al, "Food reward in the absence of taste receptor signaling", Neuron. 2008;57(6):930-41.
Kasibhatla SR, et al, "AMP deaminase inhibitors. 3. SAR of 3-(carboxyarylalkyl)coformycin aglycon analogues", Journal of medicinal chemistry. 2000;43(8):1508-18.
Lanaspa MA, et al, "Counteracting Roles of AMP Deaminase and AMP Kinase in the Development of Fatty Liver", PloS one. 2012;7(11):e48801.
Lanaspa MA, et al, "Opposing activity changes in AMP deaminase and AMP-activated protein kinase in the hibernating ground squirrel", PloS one. 2015;10(4):e0123509.

(Continued)

*Primary Examiner* — Tracy Vivlemore
(74) *Attorney, Agent, or Firm* — Timothy H. Van Dyke; Wolter Van Dyke Davis, PLLC

(57) ABSTRACT

The invention relates to the use of adenosine monophosphate deaminase 2 (AMPD2) inhibitors alone or in combination with various agents to treat a wide variety of diseases including, but not limited to, sugar craving, salt craving, umami craving, and addictions including drug, tobacco, nicotine and alcohol addictions. Embodiments of the invention may also relate to stimulation of AMPD2 activity to treat anorexia nervosa or stimulate food intake in a subject.

4 Claims, 8 Drawing Sheets

Specification includes a Sequence Listing.

(56) References Cited

OTHER PUBLICATIONS

Mathupala S, "Delivery of small-interfering RNA (siRNA) to the brain", Expert Opin Ther Pat, pp. 137-140, vol. 19, Issue 2 (2009).
Moore SC, et al, "Confectionery consumption in childhood and adult violence", Br J Psychiatry. 2009;195(4):366-7.
Nakagawa T, et al, "A causal role for uric acid in fructose-induced metabolic syndrome", Am J Physiol Renal Physiol. 2006;290(3):F625-31.
Rada P, et al, "Daily bingeing on sugar repeatedly releases dopamine in the accumbens shell", Neuroscience. 2005;134(3):737-44.
Stephan BC, et al, "Increased fructose intake as a risk factor for dementia", J Gerontol A Biol Sci Med Sci. 2010;65(8):809-14.
Stice E, et al, "Weight gain is associated with reduced striatal response to palatable food", J Neurosci. 2010;30(39):13105-9.
Volkow ND, et al, "Evaluating dopamine reward pathway in ADHD: clinical implications", JAMA. 2009;302(10):1084-91.
Von Holstein-Rathlou S, et al, "FGF21 Mediates Endocrine Control of Simple Sugar Intake and Sweet Taste Preference by the Liver", Cell Metab. 2016;23(2):335-43.
Avena NM, et al, "Sugar bingeing in rats", Curr Protoc Neurosci. 2006; pp. 1-6.
Johnson RJ, et al, "Attention Deficit-Hyperactivity Disorder: Is It Time to Reappraise the Role of Sugar Consumption?", Postgraduate Med. 2011:in press.

\* cited by examiner

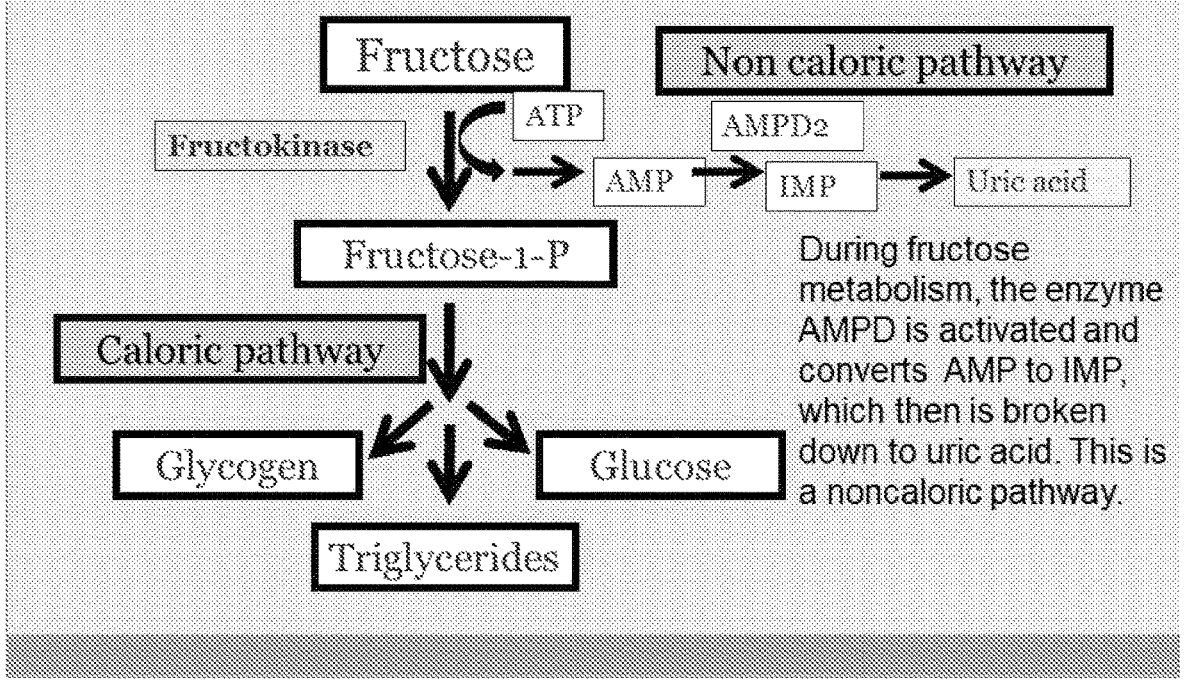

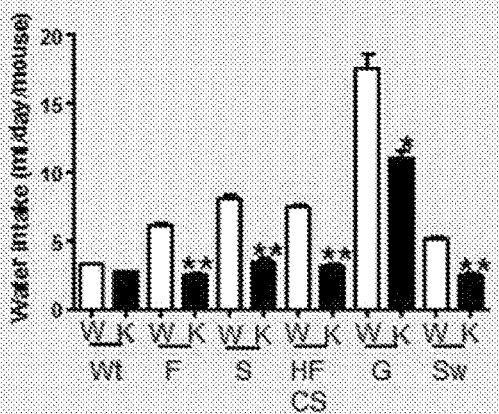
Figure 2 AMPD2 KO Mice Do not Like Simple Sugars or Artificial Sugar
Mice were offered water (Wt) or water with 15% fructose (F), sucrose (S), High fructose corn syrup (HFCS), glucose (G) or 0.04% sucralose (SW). While Wild type mice (W) preferred sweetened fluids over water, AMPD2 Knockout mice (K) showed much less liking of sweetened fluids.

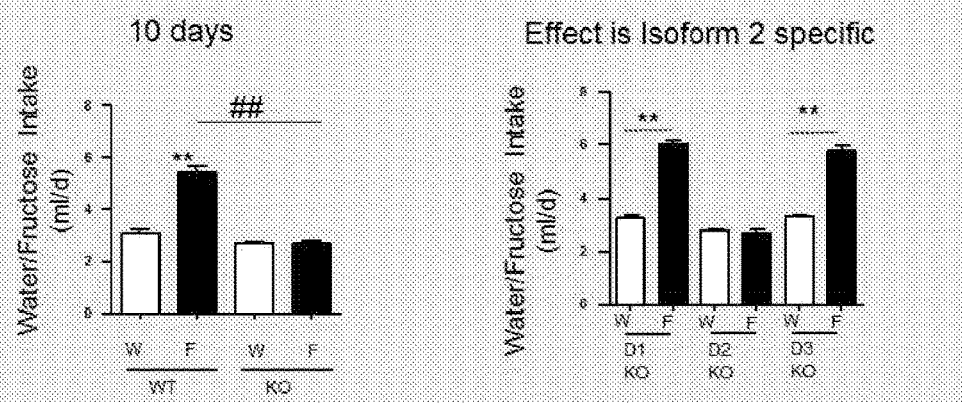

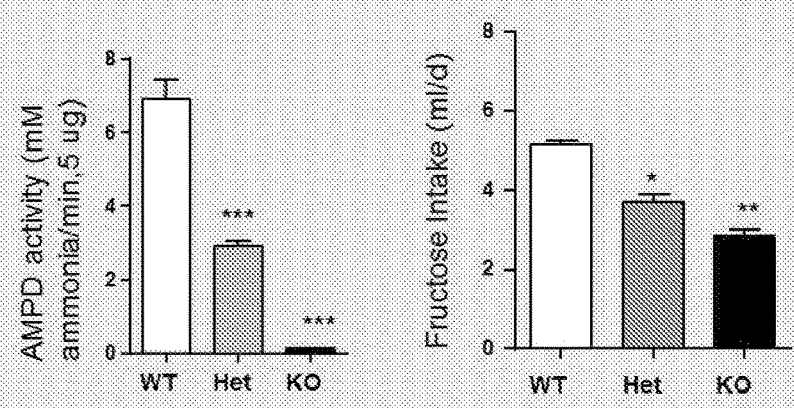
Figure 4 AMPD2 Heterozygotes show half the Effect as the AMPD2 KO (Dose Dependency)
Left: Wild type (WT) mice have significant AMPD activity in their liver while AMPD KO mice (K) have none and AMPD heterozygote (Hets) have intermediate activity. Right: While WT mice like to drink fructose (15%) drinking water, Hets drink significantly less and KO drink even less.

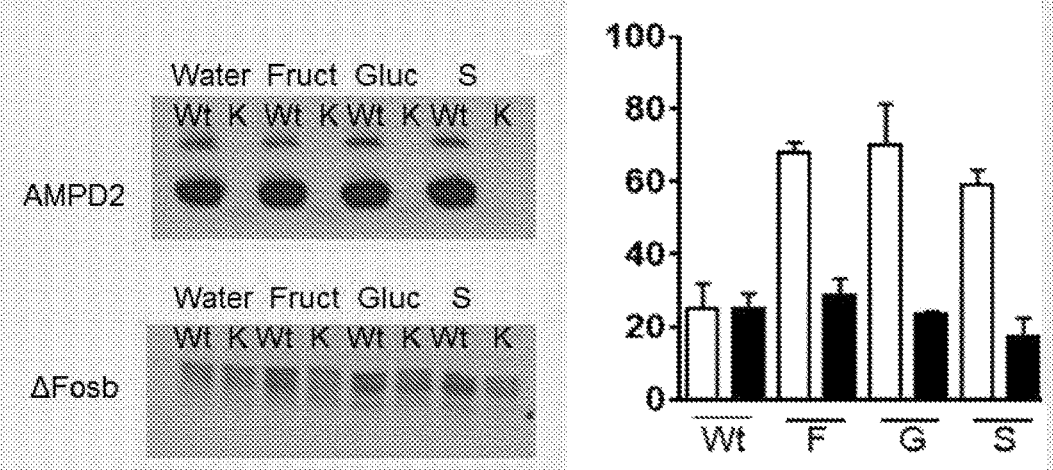

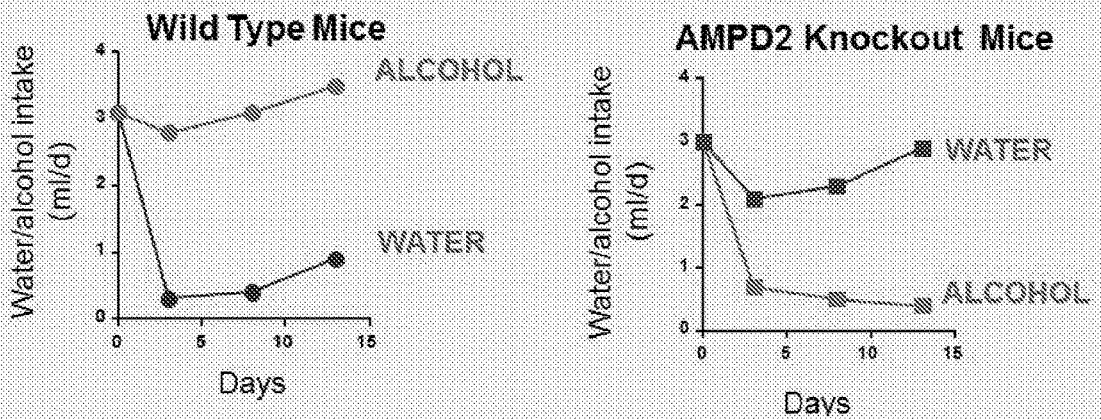

Figure 6 AMPD2 KO Mice Do not Crave Alcohol:
Two bottle preference with water or increasing alcohol (3 days 3%, 5 days 6%, 7 days 10%)

Left: Wild type mice will prefer alcohol containing water (red) over regular water. Right: AMPD2 KO mice prefer water over alcohol..

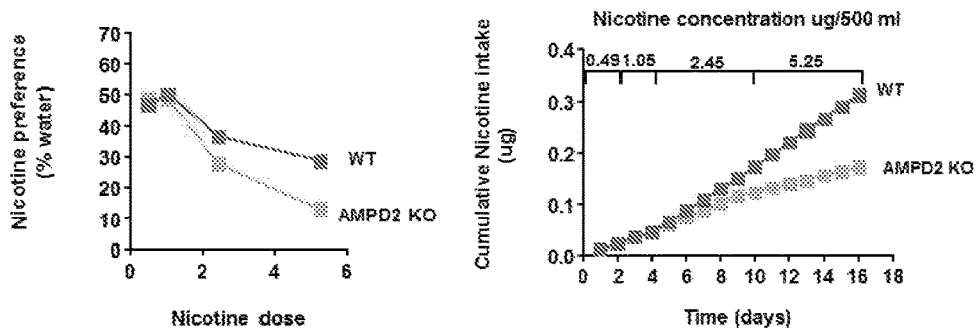

Figure 7 AMPD2 Knockout Mice Show Reduced Preference for Nicotine and Decreased Total Intake

Using a 2-bottle choice preference (water versus increasing levels of nicotine) in wild type WT (red) and AMPD2 Knockout mice ( blue). WT mice demonstrated preference for nicotine over 30% of the time compared to water while AMPD2 KO mice preferred nicotine less than 10 % of the time. Right: Cumulative nicotine intake over 16 days in the 2-bottle choice preference. Differences between nicotine intake between WT and KO are highly statistically significant.

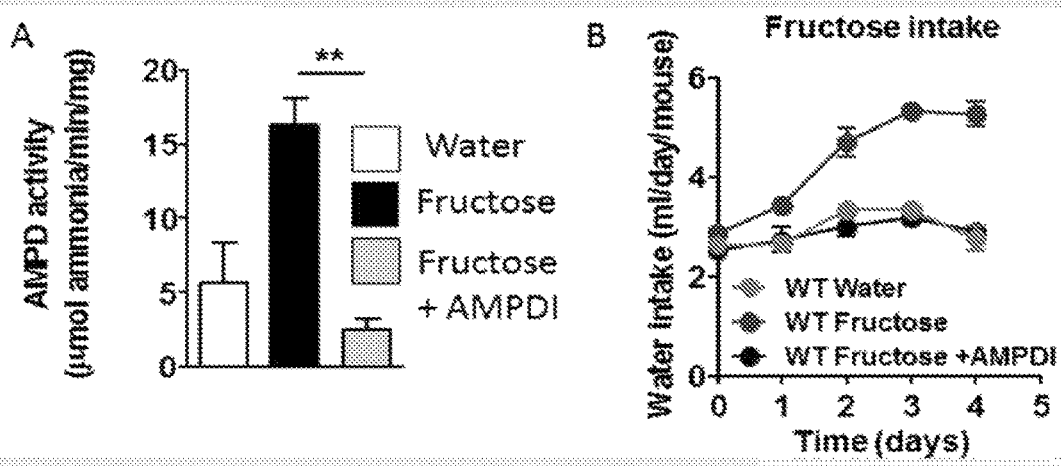

Figure 9 IMP is a stimulant for Food intake

Wild type animals gain weight with IMP added to fructose

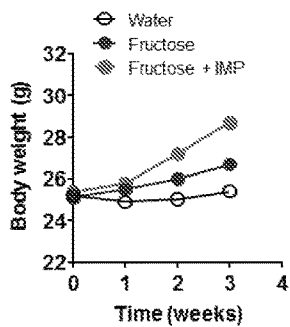

Wild type animals gain weight with IMP added to fructose

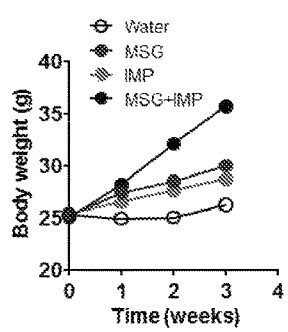

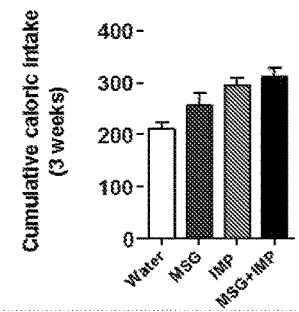

Left: IMP (300 uM), the product of AMPD, stimulates weight gain in animals given fructose (5%) in the drinking water. Center: IMP also stimulates weight gain in mice on regular chow, and also potentiates the effect of monosodium glutamate (MSG, 5%). Right panel: Energy intake on mice receiving regular chow with regular drinking water, water containing MSG, or MSG plus IMP.

TARGETING AMP DEAMINASE 2 FOR AMELIORATING CRAVING FOR SUGAR AND OTHER SUBSTANCES

FIELD

The present inventors have identified adenosine monophosphate deaminase isoform 2 (AMPD2) as a key enzyme that contributes to metabolic conditions characterized by craving for sugar, salt, and umami foods and drinks, as well as other cravings such as nicotine, alcohol, opiates, cocaine and other drug cravings familiar to drug addictions. In particular, isoform specific inhibitors targeting AMPD 2, or pan AMPD inhibitors will be effective for the prevention and/or treatment of these conditions. On the other hand, potentiators of AMPD2 activity and/or expression will be an effective therapeutic approach for anorexia nervosa as it would stimulate appetite.

BACKGROUND

Fructokinase (ketohexokinase, KHK) is a key enzyme in fructose metabolism, and phosphorylates fructose to fructose-1-phosphate. In turn, fructose 1-phosphate (F-1-P) is metabolized by aldolase B and triokinase to dihydroxyacetone phosphate (DHAP) and glyceraldehyde that continue to be metabolized, eventually generating glucose, glycogen and triglycerides. While this latter pathway is the classical caloric pathway by which fructose is metabolized, there is also a noncaloric sidechain reaction triggered when fructose is phosphorylated to F-1-P by fructokinase C (one of the isoforms). Specifically, the phosphorylation of fructose occurs very rapidly due to an inefficient negative regulation of fructokinase by downstream products—unlike glucokinase and most sugar kinases—thus causing adenosine triphosphate (ATP) and intracellular phosphate to become depleted. Adenosine monophosphate (AMP) then accumulates from ATP depletion (FIG. 1) and is metabolized by the enzyme, adenosine monophosphate deaminase 2 (AMPD2) to generate inosine monophosphate (IMP) which is progressively broken down, eventually to uric acid by xanthine oxidoreductase (XO).

Humans are known to like multiple types of sugars (table sugar also known as sucrose but also monosaccharides alone—glucose, fructose- or in mixtures—high fructose corn syrup-), as the stimulation of sweet taste causes a rapid feeling of pleasantness due in part to the stimulation of dopamine in the brain(1, 2). and/or by inefficiently stimulating the activity of the sugar satiety hormone fgf21 produced in the liver Other sweet substances, such as high fructose corn syrup, glucose, fructose, and even artificial sugars (sucralose) can also stimulate dopamine responses. However, it has been shown that the repeated ingestion of sugar in mice can lead to a craving or addiction syndrome characterized by altered levels of dopamine and dopamine receptors in dopaminergic neurons, thus leading to the necessity of more sugar to induce similar dopamine responses in the brain. Animals addicted to sugar develop features similar to that observed with drug addiction, and show signs of anxiety or withdrawal following elimination of sugar from the diet or the administration of naloxone (3, 4). The mechanism relates in part to a reduction in dopamine receptors (especially D2 receptors) in the nucleus accumbens from chronic dopamine stimulation, leading to a loss of control mechanisms in the frontal and prefrontal cortex.(5) The importance of this pathway is being increasingly recognized as a mechanism that results in lack of normal control, and may have a role in the pathogenesis of obesity, attention deficit hyperactivity disorder, drug addictions, sex addictions, and even aggressive behavior and dementia (2, 6-11). Thus, identifying a way to modulate metabolic pathways which cause or result in these cravings, including sugar, and other food cravings as well as cravings in general, such as nicotine, alcohol, opiates, cocaine and related agents, and including sexual cravings, among others could be beneficial in reducing diseases that result from these cravings, e.g., metabolic syndrome, and diabetes, as well as drug addiction and dependence.

Our published data demonstrate that the sidechain reaction involving ATP depletion, activation of AMPD isoform 2, and the generation of uric acid plays a role in driving the metabolic syndrome in response to fructose[27-29]. However, while blocking xanthine oxidase to reduce uric acid levels can improve fructose-induced metabolic syndrome, it does not have any effect on the craving for fructose or sucrose. Likewise, while blocking fructokinase C does block the craving of fructose (US Pat. Pub. No. 2013/0224218), it was not known, prior to this disclosure, if this is due to blocking the side chain reaction initiated by AMPD, or whether it is from blocking the ATP consumption and intracellular phosphate consumption, or from blocking intracellular F-1-P formation and its further metabolism via the caloric pathway (FIG. 1).

Thus, these observations indicate that to date, there was no a priori reason to believe that blocking AMPD2 could treat fructose or sugar craving (see data below).

BRIEF DESCRIPTION OF THE DRAWINGS

The invention is explained in the following description in view of the drawings that show (note that the word "figure" in the drawings has been abbreviated to "FIG."):

FIG. 1 shows the classic caloric pathway of fructose metabolism and the side chain reaction in which AMPD2 is activated.

FIG. 2 shows that AMPD2 deficiency is associated with a decreased or an absence of craving to sugars, including fructose (F), sucrose (S), high fructose corn syrup (HFCS) (mixture containing a 2 to 1 ratio of fructose and glucose monomers), glucose water (G), and sweetener—sucralose-water (SW) at 8 weeks. Concentrations were 15% in the water except for sucralose which was 0.04%. AMPD2 deficiency is also associated with reduced drinking of glucose compared to wildtype (WT) mice and no increased consumption of artificial sweeteners, such as sucralose-containing water.

FIG. 3 illustrates that AMPD2 deficient mice (KO) (knockout) do not show an increase in fructose-water intake as compared to wild type (WT) mice after 10 days of exposure to drinking fructose-containing (15%) water. The left panel shows results of overall water (W) and fructose-water (F) intake in wild type (WT) and AMPD2 deficient (KO) mice at 10 days after the start of the experiment. $P<0.01$ between mice of the same group (WT or KO), ##$P<0.01$. The right panel shows the overall water (W) and fructose-water (F) intake in AMPD2 deficient (D1KO), AMPD2 deficient (D2KO) and AMPD3 deficient, (D3KO) mice at 8 weeks ($P<0.01$ between mice of the same group (D1KO, D2KO or D3KO), ##$P<0.01$). The right panel shows that the observed effects are specific to isoform 2 of AMPD as deficiency of AMPD1 or AMPD3 in mice do not eliminate the craving for sugar or fructose.

FIG. 4 shows a dose-dependent effect in AMPD2 activity in the liver between wild type (W) (i.e, containing the AMPD2 gene in both alleles of their genome), heterozygous (Het) mice (i.e, containing only one allele copy of AMPD2 in their genome) and AMPD2 deficient mice (K) (containing no AMPD2 alleles in their genome). **P<0.001 versus WT. The right panel shows daily fructose-water intake in wild type (WT), AMPD2 heterozygous (Het), and AMPD2 deficient (KO) mice. *P<0.05 and **P<0.01 versus WT.

FIG. 5 provides a representative western blot from nucleus accumbens (NAcc) extracts for AMPD2 and deltaFosB expression from wild type (Wt) and AMPD2 deficient (K) mice exposed to water (wat), fructose (Fru), gluose (glu) or sucralose (S) for 24 hours. Left: The western blot demonstrates that AMPD2 protein is expressed in nucleus accumbens of wild type (Wt) but not AMPD2 deficient mice (K). It also shows that upon exposure of glucose, fructose and sucralose but not regular tap water there is an elevation in the expression of the transcription factor, deltaFosB (ΔFosB), in the nucleus accumbens in wild type (Wt) but not AMPD2 deficient mice (K) (right panel). Drugs and compounds that cause addiction are known to increase ΔFosB in the nucleus accumbens and this change is thought to be critical for addiction to occur (see Li et al, and Ruffle cited supra). The results of the experiments performed by the inventors herein show that AMPD2 blockade results in decreased activation of ΔFosB induced by sugar, including some not regulated by fructokinase (sucralose) suggest AMPD2 blockade may be blocking addiction pathways directly at the nucleus accumbens.

FIG. 6 shows the role of AMPD2 in the craving of alcohol. On the left panel is shown a two bottle preference study in which wild type mice can choose between regular drinking water and water that contains alcohol, with the alcohol concentration being increased from 3% (days 0-3), 6% (days 3-8) and 10% (day 8 onward). Wild type mice will rapidly prefer to drink alcohol containing water, and this increases significantly with increasing alcohol concentrations. In contrast, AMPD2 KO mice (right panel) markedly prefer regular water over alcohol-containing water, and show no increase in alcohol intake with time. This shows evidence AMPD2 KO mice not only do not crave alcohol, but have no inclination for addiction-like behavior in which alcohol intake increases with time.

FIG. 7 shows the role of AMPD2 in nicotine craving. Again, this is a two bottle preference study in which mice choose between regular drinking water and water containing nicotine. Wild type mice drinking nicotine-containing water about 30 percent of the time, while the percent of nicotine water drunk by AMPD2 KO mice is significantly less (left panel). This results in significantly less nicotine exposure over time in the AMPD2 KO mouse (right panel). Thus, blocking AMPD2 should lead to less smoking in individuals with nicotine dependence.

FIG. 8 shows the effect of an orally administered pan AMPD inhibitor (see Admyre et al., *Chem Biol*, 2014, 21(11):1486-96) on fructose craving in wild type mice. Mice were administered the racemate of the active compound 1 (FIG. 2 in the paper by Admyre et al Chem Biol 2014; 21:1488-1496) by gavage at a dose of 25 mg/kg twice daily beginning two days before administering fructose (15%) in the drinking water. As shown in the left panel, this dose could significantly block AMPD2 activity in the liver. As shown in the right panel, this dose could also significantly reduce the intake of fructose-containing water. Indeed, mice given the inhibitor drank the same amount of fructose-water as mice given regular water, documenting that the inhibitor completely blocked the craving for fructose.

FIG. 9 shows graphical data illustrating how inositol monophosphate (IMP) is a stimulant for food intake. The left panel shows that IMP (300 μM) stimulates weight gain in animals given fructose (5%) in the drinking water. The center panel shows that IMP stimulates weight gain in mice on regular chow, and also potentiates the effect of monosodium glutamate (MSG, 5%). The right panel shows energy intake on mice receiving regular chow with regular drinking water, water containing MSG, or MSG plus IMP.

DETAILED DESCRIPTION

The specifics of the discovery include the use of an agent that can specifically inhibit AMPD2 to treat specific conditions as outlined below.

To date, studies inhibiting AMPD are limited. It has been reported that inhibition of AMPD does not improve glucose control of insulin resistance or diabetes (16). However, it has been identified for the first time herein, novel roles for AMPD, which constitutes the basis for this patent application.

Our recent studies have identified roles for AMPD and its blockade in reducing or eliminating sugar (for example fructose, sucrose, high fructose corn syrup) cravings as well as potentially other cravings, including salt cravings and/or umami cravings that were not previously noted in the literature. Furthermore, our recent studies have identified roles for AMPD inhibition in ameliorating drug and other addictions.

In one non-limiting embodiment, a primary discovery relates to the finding that AMPD2 has an important role in driving a craving for sugar, e.g., sucrose, as well as glucose and artificial sugars (FIG. 2). Sugar craving is a distinct process and consists of a specific desire for sugar. It has been shown to be mediated by dopaminergic signaling in the brain and is similar to the addictive response one can observe with narcotics[30],[(12)] It had been thought to be mediated by taste receptors, but when the taste receptor signaling is blocked, craving for sugar still occurs.[31] Thus, the specific mechanism responsible for sugar craving had been unknown.

We have previously found that AMPD2 has a role in driving obesity and metabolic syndrome (U.S. Pat. No. 8,697,628B, Apr. 15 2014). However, prior to the discovery provided herein, AMPD2 had not been identified as a target for inhibiting or reducing sugar craving or for the craving for other foods or drug addiction. The discovery that blocking AMPD2 blocks sugar craving was unexpected. Indeed, one might a priori think that blocking AMPD2 should be similar to blocking uric acid production (which is a downstream product of AMPD), in which lowering uric acid improves fructose induced metabolic syndrome but does not block sugar craving[29] (13).

Consequently, the novel discovery of the inventors provided for the first time herein, that blocking or inhibiting AMPD2 decreases sugar craving is not intuitive. Furthermore, our data also demonstrate that the blockade of other isoforms of AMPD, namely AMPD1 and AMPD3, does not prevent sugar craving thus indicating that this is a specific effect related to AMPD2 inhibition, discovered by the inventors herein (FIG. 3).

Our recent studies show that mice lacking AMPD2 show no craving for fructose and that this effect is dose-dependent as heterozygous mice, i.e. mice that have approximately 50% expression and activity of AMPD2, have an intermediate effect in their liking of sugar (FIG. 4). As mentioned, Interestingly, AMPD2 deficient mice also show significantly less craving than wild type mice for other sugars including glucose, sucrose and high fructose corn syrup and artificial sweeteners like sucralose (FIG. 2). Some of these features, such as blocking the craving for artificial sugars or for glucose, are not involved in fructose metabolism and clearly demonstrate that some of the actions of AMPD2 on craving are outside the fructose metabolic pathway. Indeed, the finding that AMPD2 is highly expressed in dopaminergic neurons of the nucleus accumbens (where dopamine signaling in response to food or drugs occurs) suggests that AMPD2 has effects on craving at the central level independently of fructose metabolism, especially since to date fructokinase C has not been detected in this part of the brain.

We also have found that mice lacking AMPD1 or AMPD3 (the two other isoforms of AMPD) do not show craving for fructose, showing that the craving effects of sugar and fructose are specific for the AMPD2 isoform (FIG. 3). Thus, to block the craving to sugar, sucralose or other dopamine stimulating agents, one must either use a specific AMPD2 inhibitor or a pan AMPD inhibitor with activity against the AMPD2 isoform.

One of the major pathways involved in addiction is the activation of the transcription factor, delta Fos B ($\Delta$FosB) in the nucleus accumbens. This activation is common to multiple addictive drugs, including alcohol, cocaine, and narcotics (Chao & Nestler, *Annu Rev Med*, 2004, 55:113-32). As shown in FIG. 5, delta FosB is also activated in the nucleus accumbens in response to sugar (sucrose), fructose, glucose and other sweeteners. However, mice lacking AMPD2 show no induction of $\Delta$FosB.

Consistent with direct activity on the nucleus accumbens, we have also found that AMPD2 KO mice are protected from the craving of alcohol (FIG. 6). Specifically, when Wild type C57Bl6 mice are provided a choice between drinking water containing alcohol versus regular water (two bottle preference testing), the mice preferentially drink alcohol, and this increases over time as the alcohol content is progressively increased from 3 to 10 percent. In contrast, AMPD2 KO mice prefer water over alcohol, and drink less alcohol containing water as the alcohol concentration is increased.

Nicotine is another substance known to be addicting in humans. AMPD2 also has a role in the craving for nicotine (FIG. 7). When wild type mice are offered water containing either nicotine or regular water, they will drink nicotine-containing water approximately 30 percent of the time, but AMPD2 KO mice only drink nicotine-containing water about 10 percent of the time, and over time this results in a significant decreased nicotine intake in mice lacking AMPD2.

The benefit from blocking AMPD2 on craving is not limited to mice genetically lacking AMPD2. Recently an inhibitor for AMPD2 was published, and we made a racemate of the active compound 1 (FIG. 2 in the paper by Admyre et al Chem Biol 2014; 21:1488-1496). As shown in FIG. 8, the administration of the AMPD inhibitor orally by gavage (50 mg/kg/d) resulted in both an inhibition of AMPD2 activity in the liver and also blocked the craving for fructose.

The use of AMPD inhibitors may thus provide a variety of benefits. First, they will have significant benefit in blocking the craving of sugar or other sweeteners. This indirectly may lead to a reduction in sugar intake, that could have downstream benefits for those trying to diet or lose weight, or who are trying to block the metabolic effects of fructose. Second, blocking AMPD2 will also have other benefits by blocking the craving for other addictive or 'habit-forming' substances, including, for example, nicotine, cocaine, opioids, alcohol, cannabinoids, methylphenidate, phencyclidine, and substituted amphetamines. This benefit is expected due to the ability of AMPD2 blockade to prevent the upregulation of $\Delta$FosB in the nucleus accumbens, which is a critical regulator of craving and addiction to cocaine, narcotics, alcohol, opiates, amphetamines, marijuana, and other addicting drugs (see Li et al. *Synapse* 2008, 62(5): 358-69, and Ruffle, *Am J Drug Alcohol Abuse*, 2014 40(6): 428-37).

In another embodiment, AMPD2 could be activated in order to treat or subjects suffering from anorexia nervosa or to stimulate food intake, such as in a person with cachexia from cancer or other illnesses. AMPD2 can also generate IMP (see FIG. 1), which is taste enhancer. We found, however, that IMP also enhanced the intake of food (which was not anticipated based on the literature), including in response to fructose or regular chow. FIG. 9 shows the effect of adding IMP to the water of rats receiving fructose (5%) in their water. Within 3 weeks the addition of IMP was associated with increased weight gain. Likewise, IMP was also found to stimulate weight gain and food intake in animals in normal chow (right panel) and that this potentiated the effects of MSG (5% in the water). Hence, IMP, a product of AMPD2, when given in the diet can enhance food intake and weight gain, and hence may be useful as a means for increasing food intake in subjects with low body weight, anorexia nervosa, or cachexia of any cause.

Exemplary disorders to be treated, and exemplary risk factors to be ameliorated by the compositions and methods described herein include, but are not limited to, sugar craving, salt craving, umami craving, alcohol or drug addiction, sex addiction, addiction to nicotine, and/or other craving or addiction-related behavior of a mammal. Other disorders include obesity, fatty liver, or diabetes where craving for sugar and sweets may be problematic. In further embodiments, the compositions and methods described herein may be or may also be administered to a subject to provide a diminished craving in the subject for fructose and/or fructose-containing sugars or other sugars such as sucrose, glucose or sucralose, in non-limiting examples, to reduce body mass index or to improve kidney function. As set forth herein, the methods and compositions described herein may be administered to a subject as the single therapy or along with a conjunctive therapeutic agent, which is administered to a subject to treat or prevent the same or distinct disorder or physical condition as the AMPD2 inhibitor.

Definitions

As used herein, the terms "administering" or "administration" of an agent, drug, or peptide to a subject includes any route of introducing or delivering to a subject a compound to perform its intended function. The administering or administration can be carried out by any suitable route, including orally, intranasally, parenterally (intravenously, intramuscularly, intraperitoneally, or subcutaneously), rectally, or topically. Administering or administration includes self-administration and the administration by another.

As used herein, the terms "co-administered, "co-administering," or "concurrent administration", when used, for example with respect to administration of a conjunctive agent along with administration of an AMPD or AMPD2 inhibitor refers to administration of the AMPD or AMPD2 inhibitor and the conjunctive agent such that both can simultaneously achieve a physiological effect. The two agents, however, need not be administered together. In certain embodiments, administration of one agent can precede administration of the other, however, such co-administering typically results in both agents being simultaneously present in the body (e.g. in the plasma) of the subject.

As used herein, the terms "diabetic" or "diabetes" refers to Type 1 diabetes, wherein the pancreas produces little or no insulin; Type 2 diabetes, wherein the body becomes resistant to the effects of insulin or produces little or no insulin; or disease state occurring as sequelae of other primary diseases that include the symptoms of either or both of elevated blood sugar (hyperglycemia) and the excretion of sugar in the urine (glycosuria).

As used herein, the terms "disease," "disorder," or "complication" refers to any deviation from a normal state in a subject. In exemplified embodiments, the disease, disorder or complication pertains to a craving or addiction. The disease, disorder or complication may be characterized where the expression and/or activity of an AMPD2 protein differs between subjects with disease and subjects not having disease or where a change in ΔFosB expression in the nucleus accumbens differs between subjects with disease and subjects not having disease. Diseases may include psychological diseases, such as drug or alcohol addictions, and also cravings for sugar, salt, umami, and other cravings known to those skilled in the art. Diseases may include diabetic-related diseases.

As used herein, by the term "effective amount," "amount effective," "therapeutically effective amount," or the like, it is meant an amount effective at dosages and for periods of time necessary to achieve the desired result. In the case of the co-administration of an AMPD2 inhibitor with a conjunctive agent as described herein, the conjunctive agent, the AMPD2 inhibitor, or the combination of the AMPD2 inhibitor and the conjunctive agent may supply the effective amount.

As used herein, the term "expression" in the context of a gene or polynucleotide involves the transcription of the gene or polynucleotide into RNA. The term may also, but not necessarily, involve the subsequent translation of the RNA into polypeptide chains and their assembly into proteins.

As used herein, the terms "interfering molecule" refer to all molecules, e.g., RNA or RNA-like molecules, which have a direct or indirect influence on gene expression, such as the silencing of a target gene sequence. Examples of other interfering RNA molecules include siRNAs, short hairpin RNAs (shRNAs), single-stranded siRNAs, microRNAs (miRNAs), methylated siRNAs or other siRNAs treated to protect the siRNA from degradation by circulating RNases, and dicer-substrate 27-mer duplexes. Examples of "RNA-like" molecules include, but are not limited to, siRNA, single-stranded siRNA, microRNA, and shRNA molecules that contain one or more chemically modified nucleotides, one or more non-nucleotides, one or more deoxyribonucleotides, and/or one or more non-phosphodiester linkages. Thus, siRNAs, single-stranded siRNAs, shRNAs, miRNAs, and dicer-substrate 27-mer duplexes are subsets of "interfering molecules." "Interfering molecules" also may include PMOs.

As used herein, the terms "phosphothioate morpholino oligomer(s)," "a PMO" "PMOs" refer to molecules having the same nucleic acid bases naturally found in RNA or DNA (i.e. adenine, cytosine, guanine, uracil or thymine), however, they are bound to morpholine rings instead of the ribose rings used by RNA. They may also linked through phosphorodiamidate rather than phosphodiester or phosphorothioate groups. This linkage modification eliminates ionization in the usual physiological pH range, so PMOs in organisms or cells are uncharged molecules. The entire backbone of a PMO is made from these modified subunits.

As used herein, the term "antisense sequence" refers to an oligomeric compound that is at least partially complementary to a target nucleic acid molecule to which it hybridizes. In certain embodiments, an antisense compound modulates (increases or decreases) expression of a target nucleic acid. Antisense compounds include, but are not limited to, compounds that are oligonucleotides, oligonucleosides, oligonucleotide analogs, oligonucleotide mimetics, and chimeric combinations of these.

As used herein, the term "RNA interference" (RNAi) refers to a post-transcriptional gene silencing (PGSR) process whereby one or more exogenous small interfering RNA (siRNA) molecules are used to silence expression of a target gene. RNAi includes double-stranded RNA species mediating RNA interference (RNAi). RNAi is the process of sequence-specific, post-transcriptional gene silencing in animals and plants, initiated by double-stranded RNA (dsRNA) that is homologous in sequence to the silenced gene. Methods relating to the use of RNAi to silence genes in humans are known in the art (Fire A, et al., 1998 Nature 391: 806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619; Elbashir S M, et al., 2001 Nature 411: 494-498). RNAi may be used to knock down expression of AMPD GI #s 4557310, 14043442, and 4502078 in various cell lines using small interfering RNAs (siRNA, Elbashir et al, supra). Examples of RNAi agents include siRNA and shRNA.

As used herein, "siRNAs" (short interfering RNAs) refer to double-stranded RNA molecules, generally around 15-30 nucleotides in length, that are complementary to the sequence of the mRNA molecule transcribed from a target gene.

As used herein, "shRNAs" (small hairpin RNAs) are short "hairpin-turned" RNA sequences that may be used to inhibit or suppress gene expression.

As used herein, a "composition," "pharmaceutical composition" or "therapeutic agent" all include a composition comprising at least an AMPD2 inhibitor. Optionally, the "composition," "pharmaceutical composition" or "therapeutic agent" further comprises pharmaceutically acceptable diluents or carriers. In the case of an interfering molecule, for example, the interfering molecule may be combined with one or more pharmaceutically acceptable diluents, such as phosphate-buffered saline, for example. As used herein, a pharmaceutical composition particularly refers to a composition comprising at least an AMPD2 inhibitor that is intended to be administered to a subject as described herein.

As used herein, the term "AMPD2 inhibitor" is an agent that inhibits AMPD2. It also includes a PAN AMPD inhibitor that has AMPD2 inhibitory activity. AMPD inhibitors are known[12-14] and include molecules and compounds such as those described herein, and those described in Admyre and Kasibhalta references incorporated by reference herein[12-14]. For example, AMPD inhibitors include: N3-Substituted coformycin aglycon analogues with improved AMP deaminase (AMPDA) inhibitory potency are described. Replacement of the 5-carboxypentyl substituent in the lead AMPDA inhibitor 3-(5-carboxypentyl)-3,6,7,8-tetrahydroimidazo[4,5-d][1, 3]diazepin-8-ol (2) described in the previous article with various carboxyarylalkyl groups resulted in compounds with 10-100-fold improved AMPDA inhibitory potencies. The optimal N3 substituent had m-carboxyphenyl with a two-carbon alkyl tether. For example, 3-[2-(3-carboxy-5-ethylphenyl)ethyl]-3,6,7,8-tetrahydroimidazo[4, 5-d][1,3]diazepin-8-ol (43 g) inhibited human AMPDA with a K(i) =0.06 microM. The compounds within the series also exhibited >1000-fold specificity for AMPDA relative to adenosine deaminase[13-14]. 3-[2-(3-carboxy-4-bromo-5,6,7,8-tetrahydronaphthyl)ethyl]-3,6,7,8-tetrahydroimidazo[4,5-d][1,3]diazepin-8-ol (24b), represents a 10- to 250-fold enhancement in AMPDA inhibitory potency without loss in the enzyme specificity. The potency of the inhibitor 24b (AMPDA K(i)=0.002 microM) is 10(5)-fold lower than the Km for the substrate AMP. It represents the most potent nonnucleotide AMPDA inhibitor known[13-14]. Additional compounds include those disclosed in Admyre et al. (supra): Compound I, Compound II and Compound III 6-(4-((1-(Isoquinolin-8-yl)ethylamino)methyl)phenyl)nicotinic acid (including enantiomers), Compound IV 4'-((1-(Isoquinolin-8-yl)ethylamino)methyl)-3-methoxybiphenyl-4-carboxylic acid, and others: N-(Isoquinolin-8-ylmethylene)-2-methyl-propane-2-sulfinamide; 4'-Formyl-3-methoxybiphenyl-4-carboxylic acid[12].

As used herein, the term "AMPD" refers to AMPD2 and other isoforms of AMPD, including AMPD2, unless otherwise specified.

As used herein, the term "subject" refers to any animal (e.g., a mammal), including, but not limited to, humans, non-human primates, rodents, and the like, which is to be the recipient of a particular treatment.

As used herein, the terms "treating" or "treatment" or "alleviation" refers to both therapeutic treatment and prophylactic or preventative measures, wherein the object is to prevent or slow down (lessen), reduce symptoms, or delay progression the targeted disease, disorder or complication.

As used herein, the terms "craving" and "addiction" may be used interchangeably in certain embodiments. Typically "craving" is used in reference to sugar, salt and umami, and "addiction" is used in reference to addictive substances that, for example, stimulate dopaimine, including alcohol, sex and drugs such as nicotine, cocaine, opioids, cannabinoids, methylphenidate, phencyclidine, and substituted amphetamines, See Nieh et al., 2015, Cell 160, 528-541; Shulte et al., PLOSone, 10(2): e0117959. Doi:10.1371/journal.Pone.0177959, and Avena et al., *Neurosci Biobehav Rev.* 2008; 32(1): 20-39 for sugar addiction. In a specific embodiment, an AMPD2 related addiction refers to an addiction associated with elevated amounts of ΔFosB in the nucleus accumbens of a subject.

Description of Exemplary Embodiments

The mechanism by which sugar and other cravings occur has remained a mystery. It was originally thought that there might be a major role for taste receptors, but when taste receptor signaling is blocked, sugar (sucrose) still induces a robust dopamine response in the brain (14). The present inventors have shown that the craving for fructose and sugar (sucrose) is dependent on AMPD2. Specifically, AMPD2 deficient, also known as, knockout mice (KO mice) show a decrease in preference to no preference of water containing fructose (fructose-water), or fructose-containing sugar (sucrose, high fructose corn syrup) over drinking water alone. Also, AMPD2 deficiency in these mice is associated with reduced intake of glucose. In contrast, mice expressing AMPD2 (wild type, WT mice) exposed to both water and fructose-water show an increase in consumption of and an increase in preference to drinking fructose-water as compared to non-fructose water. Similarly, wild type mice have increased preference for sucrose, high fructose corn syrup and glucose than AMPD2 deficient mice.

These studies show that blocking AMPD2 can decrease or inhibit the craving of fructose and other sugars including fructose- and non-fructose containing sugars, and also reduce the craving for fructose-containing sugars, sucralose, and glucose, for example.

In accordance with one aspect of the present invention, there are provided methods and compositions comprising AMPD2 inhibitors for blocking AMPD2 to correspondingly reduce the craving of sugars, including fructose, sucralose, glucose, sucrose, and other monosaccharides. The craving for sugars that can be converted to fructose in the body, such as sorbitol, will also be reduced.

In accordance with another aspect of the present invention, since repeated sugar intake from craving can induce obesity, there are provided methods and compositions comprising AMPD2 inhibitors that are able to block sugar craving syndromes and hence be an adjunctive treatment for obesity. Accordingly, one embodiment provided is treatment of obesity by administering a therapeutically effective amount of an AMPD2 inhibitor.

In accordance with another aspect of the present invention, there is provided a method for reducing a craving for fructose and/or fructose-containing sugars or other sugars in a subject, the method comprising inhibiting AMDP2 activity in the subject. In one embodiment, the method comprises administering an AMPD2 inhibitor to the subject.

In accordance with another aspect of the present invention, there is provided a composition useful for decreasing a craving for sugar, sugar-containing compounds, other sweeteners and monosaccharides, the composition comprising an AMPD2 inhibitor and optionally, a conjunctive therapeutic agent.

In accordance with another aspect of the present invention, there is provided a method for treating a sugar craving, a salt-craving, and/or an umami craving. The method comprises administering to the subject a therapeutically effective amount of an AMPD2 inhibitor. A composition for treating a sugar craving, a salt-craving, an umami craving, and methods or compositions for treating other addictions, including narcotic or other drug (cocaine) additions, alcohol addictions, smoking (nicotine) addiction, sex addiction among other addictions is also provided, as well as a method of treating such cravings or addiction by administering a therapeutically effective amount of an AMPD2 inhibitor containing composition to a subject are also provided herein.

In accordance with another aspect of the present invention, there is provided a method for diminishing, inhibiting or eliminating addiction-related behavior of a subject, wherein said method comprises administering a composition comprising an AMPD2 inhibitor (to inhibit AMPD2) to the subject, and wherein the addiction-related behavior is associated with a craving for sugar, salt, umami, or addiction to drug or alcohol intake or a sex addiction. A composition for diminishing, inhibiting or eliminating addiction-related behavior of a mammal comprising an AMPD2 inhibitor may likewise be provided.

The present inventors have made novel discoveries that were not predicted based on the currently published literature. First, the inventors have discovered that a limitation or elimination of craving for sugar and or fructose can be accomplished with the inhibition or blocking of AMPD2 enzyme or a pan-AMPD inhibitor in a subject. Furthermore, the inventors have discovered that inhibition of the AMPD2 isoform or a general AMPD inhibitor that has activity against AMPD2 may also be able to block other types of craving unrelated to fructose metabolism (such as for glucose, sucralose, or other) is particularly relevant in eliminating or limiting cravings as described herein.

Further, the present inventors have also shown a dose-dependent effect of AMPD2 inhibition. The inventors have demonstrated that heterozygous mice have half the AMPD2 expression, and, half the response to fructose-water as compared to wild type mice and knockout mice. Heterozygous mice have less preference to fructose-water than wild type mice, but show an increased preference to fructose-water than knockout mice.

Moreover, the present inventors have found that AMPD2 inhibitors are also useful in decreasing a craving or decreasing a preference for sweeteners and other monosaccharides (i.e, fructose, glucose) as well as artificial sweeteners (sucralose) compared to wild type animals. In one example, a 24 hour study was conducted in which mice were exposed to water, sucralose (0.04%), glucose (10%), and fructose (15%), and the water consumption was higher in the wild type mice than in AMPD2 deficient mice (KO) exposed to these sweeteners and monosaccharides.

In accordance with one aspect of the present invention, the AMPD2 inhibitors described herein are useful as an adjunct treatment for obesity in subjects by helping in reducing sugar craving and consumption.

In accordance with another aspect of the present invention, there is provided a composition for treating or preventing a complication characterized by an increased presence or activity of AMPD2 by administering an AMPD2 inhibitor.

The AMPD2 inhibitor may include one or more of a ribozyme, an interfering molecule, a peptide, a small molecule, or an antibody targeted to AMPD2. In a particular embodiment, the AMPD2 inhibitor comprises an interfering molecule that can participate in changes in gene expression of AMPD2, such as the silencing of expression of the AMPD2. Without limitation, the interfering molecule may comprise a phosphothioate morpholino oligomer (PMO), miRNA, siRNA, shRNA, any other antisense sequence, or any combination thereof.

AMPD2 can be inhibited by a number of means as set forth further below, including silencing via miRNA, shRNA, siRNA, or a PMO directed to a portion of the sequence described at the genbank accession numbers provided below. See U.S Patent Publication 20060110440 for background on siRNA silencing, the entirety of which is hereby incorporated by reference. As discussed above, agents can be developed to inhibit AMPD2 to achieve a beneficial effect on obesity, metabolic syndrome and related diseases and complications, sugar and other cravings discussed herein and other addictions including drug and alcohol addictions.

It is noted that the compositions and methods disclosed herein may be administered to any subject as defined herein. In one embodiment, the subject is human. In another embodiment, the subject is a pet, e.g., cat, dog, or the like, and in a particular embodiment, is an overweight pet or animal. It is further noted that a corresponding composition, e.g., a pharmaceutical composition, may be provided for use in any method described Gene Expression In another embodiment, test compounds which increase or decrease AMPD2 gene expression are identified. An AMPD polynucleotide is contacted with a test compound, and the expression of an RNA or polypeptide product of the AMPD polynucleotide is determined. The level of expression of appropriate mRNA or polypeptide in the presence of the test compound is compared to the level of expression of mRNA or polypeptide in the absence of the test compound. The test compound can then be identified as a modulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of AMPD2 mRNA or polypeptide expression in the cells can be determined by methods well known in the art for detecting mRNA or polypeptide. Either qualitative or quantitative methods can be used. The presence of polypeptide products of an AMPD2 polynucleotide can be determined, for example, using a variety of techniques known in the art, including immunochemical methods such as radio-immunoassay, Western blotting, and immunohistochemistry. Alternatively, polypeptide synthesis can be determined in vivo, in a cell culture, or in an in vitro translation system by detecting incorporation of labeled amino acids into an AMPD2 polypeptide.

Such screening can be carried out either in a cell-free assay system or in an intact cell. Any cell which expresses an AMPD2 polynucleotide can be used in a cell-based assay system. The AMPD2 polynucleotide can be naturally occurring in the cell or can be introduced using techniques such as those described above. Either a primary culture or an established cell line, such as CHO or human embryonic kidney 293 cells, can be used.

Pharmaceutical Compositions

The invention also pertains to compositions, e.g., pharmaceutical compositions, comprising one or more therapeutic agents that inhibit AMPD2. In one embodiment, the therapeutic agents inhibit AMPD2. Therapeutic agents include those that are identified by screening methods that utilize AMPD2 polypeptides and/or polynucleotides. Therapeutic agent(s) can be administered to a patient to achieve a therapeutic effect, i.e. useful in modulating AMPD2 activity and in turn, treating and/or preventing obesity, sugar cravings, and/or other cravings described herein. Compositions of the invention can comprise, for example, therapeutic agents identified by a screening method embodiment described herein, which are identified by their ability to bind to or affect activity of AMPD2 polypeptides, or bind to and/or affect expression of AMPD2 polynucleotides. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these compositions can contain suitable pharmaceutically acceptable carriers comprising excipients and auxiliaries which facilitate processing of the active compounds into preparations which can be used pharmaceutically. Compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Further details on techniques for formulation and administration can be found in the latest edition of REMINGTON'S PHARMACEUTICAL SCIENCES (Maack Publishing Co., Easton, Pa., which is incorporated herein by reference). After pharmaceutical compositions have been prepared, they can be placed in an appropriate container and labeled for treatment of an indicated condition. Such labeling would include amount, frequency, and method of administration.

Accordingly, some examples of an agent having therapeutic activity as described herein, include but are not limited to a modulating agent, an antisense nucleic acid molecule, small molecule AMPD2 inhibitors, peptide inhibitors, a specific antibody, ribozyme, interfering molecules, or an AMPD2 polypeptide binding molecule targeted to AMPD2. In one embodiment, the agent comprises an interfering molecule and the interfering molecule comprises a phosphothioate morpholino oligomer (PMO), miRNA, methylated miRNA, treated-miRNA, siRNA, shRNA, antisense RNA, and any combination thereof.

Each of the compositions and methods described herein may include an effective amount of the AMPD2 inhibitor. In one embodiment, the AMPD2 inhibitor is combined with one or more conjunctive therapeutic agents to bring about a desired effect in the subject. This effect may be realized by an effective amount of the AMPD2 inhibitor, an effective amount of the conjunctive agent, or an effective amount of the combination of the AMPD2 and the one or more conjunctive therapeutic agents. It is understood that the administration of the AMPD2 inhibitor with one or more conjunctive therapeutic agents may advantageously increase an efficacy of the AMPD2 inhibitor, the conjunctive therapeutic agent, or both.

In certain embodiments, inhibiting AMPD2 involves downregulation of gene expression, translation or activity of AMPD genes.

The methods and compositions described herein may be directed at inhibiting expression of inhibiting the gene expression, translation or activity of genes. In a particular embodiment, the methods and compositions described herein are directed at inhibiting the gene expression, translation or activity of AMPD2.

Agents can be used in an animal model to determine the efficacy, toxicity, or side effects of treatment with such an agent. In addition, compositions may include a conjunctive agent in addition to the therapeutic agents of the present invention. A comprehensive discussion of many different agents that can be used in combination with a therapeutic agent comprising an AMPD2 inhibitor is described in U.S. Patent Pub. 20080255101, the entirety of which is incorporated by reference herein. According to specific embodiments, small molecule AMPD2 inhibitors include, but are not limited to, 3-[2-(3-carboxy-4-bromo-5,6,7,8-tetrahydronaphthyl)ethyl]-3,6,7,8-tetrahydroimidazo[4,5-d][1,3]diazepin-8-ol[13].

Exemplary compounds include for use in combination or co-administration with the therapeutic agent(s) or composition comprising an AMPD2inhibitor as described herein may be selected from the group consisting of angiotensin-converting enzyme (ACE) inhibitors, aldosterone antagonists, amphetamines, amphetamine-like agents, Angiotensin II receptor antagonists, anti-oxidants, aldose reductase inhibitors, biguanides, sorbitol dehydrogenase inhibitors, thiazolidinediones (glitazones), thiazide and thiazide-like diuretics, triglyceride synthesis inhibitors, uric acid lowering drugs, e.g., xanthine oxidase inhibitors, ketohexokinase (fructokinase) inhibitors and combinations thereof.

Those skilled in the art will appreciate that numerous delivery mechanisms are available for delivering a therapeutic agent to an area of need. By way of example, the agent may be delivered using a liposome as the delivery vehicle. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human.

A liposome useful in the present invention comprises a lipid composition that is capable of fusing with the plasma membrane of the targeted cell to deliver its contents to the cell. Preferably, the transfection efficiency of a liposome is about 0.5 µg of DNA per 16 nmole of liposome delivered to about $10^6$ cells, more preferably about 1.0 µg of DNA per 16 nmole of liposome delivered to about $10^6$ cells, and even more preferably about 2.0 µg of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes conventionally used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

Complexing a liposome with a reagent such as an antisense oligonucleotide or ribozyme can be achieved using methods which are standard in the art (see, for example, U.S. Pat. No. 5,705,151). Preferably, from about 0.1 µg to about 10 µg of polynucleotide is combined with about 8 nmol of liposomes, more preferably from about 0.5 µg to about 5 µg of polynucleotides are combined with about 8 nmol liposomes, and even more preferably about 1.0 µg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. Trends in Biotechnol. 11, 202-05 (1993); Chiou et al., GENE THERAPEUTICS: METHODS AND APPLICATIONS OF DIRECT GENE TRANSFER (J. A. Wolff, ed.) (1994); Wu & Wu, J. Biol. Chem. 263, 621-24 (1988); Wu et al., J. Biol. Chem. 269, 542-46 (1994); Zenke et al., Proc. Natl. Acad. Sci. U.S.A. 87, 3655-59 (1990); Wu et al., J. Biol. Chem. 266, 338-42 (1991).

2.1 Determination of a Therapeutically Effective Dose

The determination of a therapeutically effective dose of therapeutic agents identified by a screening method herein is well within the capability of those skilled in the art. A therapeutically effective dose refers to that amount of active ingredient which modulates AMPD2 activity compared to that which occurs in the absence of the therapeutically effective dose.

Therapeutic efficacy and toxicity, e.g., ED50 (the dose therapeutically effective in 50% of the population) and LD50 (the dose lethal to 50% of the population), can be determined by standard pharmaceutical procedures in cell cultures or experimental animals. The dose ratio of toxic to therapeutic effects is the therapeutic index, and it can be expressed as the ratio, LD50/ED50.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Preferably, a therapeutic agent reduces expression of an AMPD gene or the activity of an AMPD polypeptide by at least about 10, preferably about 50, more preferably about 75, 90, or 100% relative to the absence of the reagent. The effectiveness of the mechanism chosen to decrease the level of expression of an AMPD gene or the activity of an AMPD polypeptide can be assessed such as by hybridization of nucleotide probes to AMPD-specific mRNA, quantitative RT-PCR, immunologic detection of an AMPD polypeptide, or measurement of AMPD activity.

2.2 Conjunctive Therapeutic Agents

In any of the embodiments described above, any of the compositions of the invention can be co-administered with other appropriate therapeutic agents (conjunctive agent or conjunctive therapeutic agent) for the treatment or prevention of a target disease. Selection of the appropriate conjunctive agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects. Exemplary conjunctive agents that may be formulated and/or administered with any form of an AMPD2 inhibitor as described herein include, but are not limited to, angiotensin-converting enzyme (ACE) inhibitors, aldosterone antagonists, amphetamines, amphetamine-like agents, Angiotensin II receptor antagonists, antioxidants, aldose reductase inhibitors, biguanides, sorbitol dehydrogenase inhibitors, thiazolidinediones (glitazones), thiazide and thiazide-like diuretics, triglyceride synthesis inhibitors, uric acid lowering agents, e.g., xanthine oxidase inhibitors, fructokinase inhibitors, and combinations thereof.

Exemplary ACE inhibitors include, but are not limited to, Benazepril (Lotensin), Captopril, Enalapril (Vasotec), Fosinopril, Lisinopril (Prinivil, Zestril), Moexipril (Univasc), Perindopril (Aceon), Quinapril (Accupril), Ramipril (Altace), Trandolapril (Mavik), and combinations thereof.

Exemplary aldosterone antagonists include, but are not limited to, Spironolactone, Eplerenone, Canrenone (canrenoate potassium), Prorenone (prorenoate potassium), Mexrenone (mexrenoate potassium), and combinations thereof.

Exemplary amphetamines include, but are not limited to, amphetamine, methamphetamine, methylphenidate, p-methoxyamphetamine, methylenedioxyamphetamine, 2,5-dimethoxy-4-methylamphetamine, 2,4,5-trimethoxyamphetamine, and 3,4-methylenedioxymethamphetamine, N-ethylamphetamine, fenethylline, benzphetamine, and chlorphentermine as well as the amphetamine compounds of Adderall®; actedron; actemin; adipan; akedron; allodene; alpha-methyl-(.+-.)-benzeneethanamine; alpha-methylbenzeneethanamine; alpha-methylphenethylamine; amfetamine; amphate; anorexine; benzebar; benzedrine; benzyl methyl carbinamine; benzolone; beta-amino propylbenzene; beta-phenylisopropylamine; biphetamine; desoxynorephedrine; dietamine; DL-amphetamine; elastonon; fenopromin; finam; isoamyne; isomyn; mecodrin; monophos; mydrial; norephedrane; novydrine; obesin; obesine; obetrol; octedrine; oktedrin; phenamine; phenedrine; phenethylamine, alpha-methyl-; percomon; profamina; profetamine; propisamine; racephen; raphetamine; rhinalator; sympamine; simpatedrin; simpatina; sympatedrine; and weckamine. Exemplary amphetamine-like agents include but are not limited to methylphenidate. Exemplary compounds for the treatment of ADD include, but are not limited to, methylphenidate, dextroamphetamine/amphetamine, dextroamphetamine, and atomoxetine (non-stimulant).

Exemplary Angiotensin II receptor antagonists or angiotensin receptor blockers (ARBs) include, but are not limited to losartan, irbesartan, olmesartan, candesartan, valsartan, and combinations thereof.

Exemplary anti-oxidant compounds include but are not limited to L-ascorbic acid or L-ascorbate (vitamin C), menaquinone (vitamin K 2), plastoquinone, phylloquinone (vitamin K 1), retinol (vitamin A), tocopherols (e.g., $\alpha$, $\beta$, $\gamma$ and $\delta$-tocotrienols, ubiquinol, and ubiquione (Coenzyme Q10)); and cyclic or polycyclic compounds including acetophenones, anthroquinones, benzoquiones, biflavonoids, catechol melanins, chromones, condensed tannins, coumarins, flavonoids (catechins and epicatechins), hydrolyzable tannins, hydroxycinnamic acids, hydroxybenzyl compounds, isoflavonoids, lignans, naphthoquinones, neolignans, phenolic acids, phenols (including bisphenols and other sterically hindered phenols, aminophenols and thiobisphenols), phenylacetic acids, phenylpropenes, stilbenes and xanthones. Additional cyclic or polycyclic antioxidant compounds include apigenin, auresin, aureusidin, Biochanin A, capsaicin, catechin, coniferyl alcohol, coniferyl aldehyde, cyanidin, daidzein, daphnetin, deiphinidin, emodin, epicatechin, eriodicytol, esculetin, ferulic acid, formononetin, gernistein, gingerol, 3-hydroxybenzoic acid, 4-hydroxybenzoic acid, 3-hydroxycoumarin, juglone, kaemferol, lunularic acid, luteolin, malvidin, mangiferin, 4-methylumbelliferone, mycertin, naringenin, pelargonidin, peonidin, petunidin, phloretin, p-hydroxyacetophenone, (+)-pinoresinol, procyanidin B-2, quercetin, resveratol, resorcinol, rosmaric acid, salicylic acid, scopolein, sinapic acid, sinapoyl-(S)-maleate, sinapyl aldehyde, syrginyl alcohol, telligrandin umbelliferone and vanillin. Antioxidants may also be obtained from plant extracts, e.g., from blackberries, blueberries, black carrots, chokecherries, cranberries, black currants, elderberries, red grapes and their juice, hibiscus, oregano, purple sweet potato, red wine, rosemary, strawberries, tea (e.g., black, green or white tea), and from various plant ingredients as ellagic acid.

Exemplary aldose reductase inhibitors include, but are not limited to, epalrestat, ranirestat, fidarestat, sorbinil, and combinations thereof.

Exemplary biguanides include, but are not limited to, metformin, and less rarely used phenformin and buformin, proguanil, and combinations thereof.

Exemplary thiazolidinediones include, but are not limited to, troglitazone, pioglitazone, ciglitazone, rosiglitazone, englitazone, and combinations thereof.

Exemplary sorbitol dehydrogenase inhibitors are disclosed in U.S. Pat. Nos. 6,894,047, 6,570,013, 6,294,538, and US Published Patent Application No. 20050020578, the entirety of which are incorporated by reference herein.

Exemplary thiazide and thiazide-like diuretics include, but are not limited to, benzothiadiazine derivatives, chlortalidone, metolazone, and combinations thereof.

Exemplary triglyceride synthesis inhibitors include, but are not limited to, diglyceride acyltransferase 1 (DGAT-1) inhibitors.

Exemplary uric acid lowering agents include, but are not limited to, xanthine oxidase inhibitors, such as allopurinol, oxypurinol, tisopurine, febuxostat, inositols (e.g., phytic acid and myo-inositol), fructokinase inhibitors, and combinations thereof.

Exemplary fructokinase inhibitors include, but are not limited to, osthol, alpha mangosteen, luteolin, osthenol, or indazole derivatives (see US Pub No. 2011/0263559) or Pyrimidinopyrimidine derivatives (US2011/0263559).

It is appreciated that suitable conjuvant therapeutic agents for use in the present invention may also comprise any combinations, prodrugs, pharmaceutically acceptable salts, analogs, and derivatives of the above compounds.

In one embodiment, the AMPD inhibitor may be administered to the subject along with one or more other therapeutic agents that are active in acute and chronic kidney disease. Exemplary conjuvant therapeutic agents for this use include but are not limited to angiotensin-converting enzyme (ACE) inhibitors, aldosterone antagonists, Angiotensin II receptor antagonists, anti-oxidants, aldose reductase inhibitors, biguanides, sorbitol dehydrogenase inhibitors, thiazolidinediones (glitazones), xanthine oxidase inhibitors, and/or any other agent used to treat acute or chronic kidney disease.

It is appreciated by one skilled in the art that when any one or more the AMPD inhibitors described herein are combined with another therapeutic agent, the AMPD inhibitor(s) may critically allow for increased efficacy of the therapeutic agent or allow for reduction of the dose of the other therapeutic agent that may have a dose-related toxicity associated therewith.

The mode of administration for a conjunctive formulation in accordance with the present invention is not particularly limited, provided that the AMPD2 inhibitor and the conjunctive agent are combined upon administration. Such an administration mode may, for example, be (1) an administration of a single formulation obtained by formulating an AMPD2 inhibitor and the conjunctive agent simultaneously; (2) a simultaneous administration via an identical route of the two agents obtained by formulating an AMPD2 inhibitor and a conjunctive agent separately; (3) a sequential and intermittent administration via an identical route of the two agents obtained by formulating an AMPD2 inhibitor and a conjunctive agent separately; (4) a simultaneous administration via different routes of two formulations obtained by formulating an AMPD2 inhibitor and a conjunctive agent separately; and/or (5) a sequential and intermittent administration via different routes of two formulations obtained by formulating an AMPD2 inhibitor and a conjunctive agent separately (for example, an AMPD2 or its composition followed by a conjunctive agent or its composition, or inverse order) and the like.

The dose of a conjunctive formulation may vary depending on the formulation of the AMPD2 inhibitor and/or the conjunctive agent, the subject's age, body weight, condition, and the dosage form as well as administration mode and duration. One skilled in the art would readily appreciate that the dose may vary depending on various factors as described above, and a less amount may sometimes be sufficient and an excessive amount should sometimes be required.

The conjunctive agent may be employed in any amount within the range causing no problematic side effects. The daily dose of a conjunctive agent is not limited particularly and may vary depending on the severity of the disease, the subject's age, sex, body weight and susceptibility as well as time and interval of the administration and the characteristics, preparation, type and active ingredient of the pharmaceutical formulation. An exemplary daily oral dose per kg body weight in a subject, e.g., a mammal, is about 0.001 to 2000 mg, preferably about 0.01 to 500 mg, more preferably about 0.1 to about 100 mg as medicaments, which is given usually in 1 to 4 portions.

When an AMPD2 inhibitor and a conjunctive agent are administered to a subject, the agents may be administered at the same time, but it is also possible that the conjunctive agent is first administered and then the AMPD2 inhibitor is administered, or that the AMPD2 is first administered and then the conjunctive agent is administered. When such an intermittent administration is employed, the time interval may vary depending on the active ingredient administered, the dosage form and the administration mode, and for example, when the conjunctive agent is first administered, the AMPD2-inhibitor may be administered within 1 minute to 3 days, preferably 10 minutes to 1 day, more preferably 15 minutes to 1 hour after the administration of the conjunctive agent. When the AMPD2 inhibitor is first administered, for example, then the conjunctive agent may be administered within 1 minute to 1 day, preferably 10 minutes to 6 hours, more preferably 15 minutes to 1 hour after the administration of the AMPD2 inhibitor.

It is understood that when referring to an AMPD2 inhibitor and a conjunctive agent, it is meant an AMPD2 inhibitor alone, a conjunctive agent alone, as a part of a composition, e.g., composition, which optionally includes one or more pharmaceutical carriers. It is also contemplated that more than one conjunctive agent may be administered to the subject if desired.

Polypeptides

AMPD polypeptides according to an aspect of the present invention comprise at least 12, 15, 25, 50, 75, 100, 125, 150, 175, 200, 225, 250 or 265 contiguous amino acids selected from the amino acid sequence shown in SEQ ID NOs: 7, 8, 9, 10, 11, and 12 or a biologically active variant thereof, as defined below. An AMPD polypeptide of the invention therefore can be a portion of an AMPD protein, a full-length AMPD protein, or a fusion protein comprising all or a portion of AMPD protein.

Biologically Active Variants

AMPD polypeptide variants which are biologically active, i.e., confer an ability to deaminate adenosine monophosphate (AMP), also are considered AMPD polypeptides for purposes of this application. Preferably, naturally or non-naturally occurring AMPD polypeptide variants have amino acid sequences which are at least about 55, 60, 65, or 70, preferably about 75, 80, 85, 90, 96, 96, or 98% identical to the amino acid sequence shown in SEQ. ID NOS.: 7, 8, 9, 10, 11, 12 for all the AMPD2 protein isofroms derived from each transcript variant identified or a fragment thereof. Percent identity between a putative AMPD polypeptide variant and an amino acid sequence of SEQ. ID NOS: 7, 8, 9, 10, 11, 12 determined using the Blast2 alignment program (Blosum62, Expect 10, standard genetic codes).

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of aleucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of a AMPD polypeptide can be found using computer programs well known in the art, such as DNASTAR software. Whether an amino acid change results in a biologically active AMPD polypeptide can readily be determined by assaying for AMPD activity, as described herein, for example. Mass.), and Quantum Biotechnologies (Montreal, Canada; 1-888-DNA-KITS).

Polynucleotides

An AMPD polynucleotide can be single- or double-stranded and comprises a coding sequence or the complement of a coding sequence for an AMPD polypeptide. A coding sequence for AMPD polypeptide of SEQ ID NOS: 1, 2, 3, 4, 5, or 6 for each transcript variant identified to date.

Degenerate nucleotide sequences encoding AMPD polypeptides, as well as homologous nucleotide sequences which are at least about 50, 55, 60, 65, 60, preferably about 75, 90, 96, or 98% identical to the nucleotide sequence shown in SEQ ID NOS: 1, 2, 3, 4, 5, or 6 for each transcript variant identified to date also are AMPD-like enzyme polynucleotides. Percent sequence identity between the sequences of two polynucleotides is determined using computer programs such as ALIGN which employ the FASTA algorithm, using an affine gap search with a gap open penalty of –12 and a gap extension penalty of –2. Complementary DNA (cDNA) molecules, species homologs, and variants of AMPD polynucleotides which encode biologically active AMPD polypeptides also are AMPD polynucleotides.

4.1 Identification of Polynucleotide Variants and Homologs

Variants and homologs of the AMPD polynucleotides described above also are AMPD polynucleotides. Typically, homologous AMPD polynucleotide sequences can be identified by hybridization of candidate polynucleotides to known AMPD polynucleotides under stringent conditions, as is known in the art. For example, using the following wash conditions: 2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each homologous sequences can be identified which contain at most about 25-30% basepair mismatches. More preferably, homologous nucleic acid strands contain 15-25% basepair mismatches, even more preferably 5-15% basepair mismatches.

Species homologs of the AMDP polynucleotides disclosed herein also can be identified by making suitable probes or primers and screening cDNA expression libraries.

It is well known that the Tm of a double-stranded DNA decreases by 1-1.5° C. with every 1% decrease in homology (Bonner et al., J. Mol. Biol. 81, 123 (1973). Variants of AMPD polynucleotides or polynucleotides of other species can therefore be identified by hybridizing a putative homologous AMPD polynucleotide with a polynucleotide having a nucleotide sequence of SEQ ID NO.: 1, 2, 3, 4, 5, or 6 for each transcript variant identified to date or the complement thereof to form a test hybrid. The melting temperature of the test hybrid is compared with the melting temperature of a hybrid comprising polynucleotides having perfectly complementary nucleotide sequences, and the number or percent of basepair mismatches within the test hybrid is calculated.

Nucleotide sequences which hybridize to AMPD polynucleotides or their complements following stringent hybridization and/or wash conditions also are AMPD polynucleotides. Stringent wash conditions are well known and understood in the art and are disclosed, for example, in Sambrook et al., MOLECULAR CLONING: A LABORATORY MANUAL, $2^{nd}$ ed., 1989, at pages 9.50-9.51.

Typically, for stringent hybridization conditions a combination of temperature and salt concentration should be chosen that is approximately 12-20° C. below the calculated $T_m$ of the hybrid under study. The $T_m$ of a hybrid between an AMPD polynucleotide having a nucleotide sequence shown in SEQ ID NO.: 1, 2, 3, 4, 5, or 6 for each transcript variant identified to date or the complement thereof and a polynucleotide sequence which is at least about 50, preferably about 75, 90, 96, or 98% identical to one of those nucleotide sequences can be calculated, for example, using the equation of Bolton and McCarthy, Proc. Natl. Acad. Sci. U.S.A. 48, 1390 (1962):

$T_m$=81.5° C.-16.6($\log_{10}$ [Na$^+$])+0.41(% G+C)–0.63(% formamide)–600/l), where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Preparation of Polynucleotides

A naturally occurring AMPD polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated AMPD polynucleotides. For example, restriction enzymes and probes can be used to isolate polynucleotide fragments which comprises AMPD nucleotide sequences. Isolated polynucleotides are in preparations which are free or at least 70, 80, or 90% free of other molecules.

AMPD DNA molecules can be made with standard molecular biology techniques, using AMPD mRNA as a template. AMPD DNA molecules can thereafter be replicated using molecular biology techniques known in the art and disclosed in manuals such as Sambrook et al. (1989). An amplification technique, such as PCR, can be used to obtain additional copies of polynucleotides of the invention. The inventors have successfully demonstrated this approach.

Alternatively, synthetic chemistry techniques can be used to synthesize AMPD polynucleotides. The degeneracy of the genetic code allows alternate nucleotide sequences to be synthesized which will encode a AMPD polypeptide having, for example, an amino acid sequence shown in SEQ ID NOs: 7, 8, 9, 10, 11, 12 for all the AMPD2 protein isofroms derived from each transcript variant identified or a biologically active variant thereof.

Expression of Polynucleotides

To express an AMPD polynucleotide, the polynucleotide can be inserted into an expression vector which contains the necessary elements for the transcription and translation of the inserted coding sequence. Methods which are well known to those skilled in the art can be used to construct expression vectors containing sequences encoding AMPD polypeptides and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., CURRENT PROTOCOLS IN MOLECULAR BIOLOGY, John Wiley & Sons, New York, N.Y., 1989.

A variety of expression vector/host systems can be utilized to contain and express sequences encoding an AMPD enzyme polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those nontranslated regions of the vector enhancers, promoters, 5' and 3' untranslated regions which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUE-SCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding an AMPD polypeptide, vectors based on SV40 or EBV can be used with an appropriate selectable marker.

Host Cells

According to certain embodiments of the subject invention, an AMPD polynucleotide will need to be inserted into a host cell, for expression, processing and/or screening. A host cell strain can be chosen for its ability to modulate the expression of the inserted sequences or to process the expressed AMPD polypeptide in the desired fashion. Such modifications of the polypeptide include, but are not limited to, acetylation, carboxylation, glycosylation, phosphorylation, lipidation, and acylation. Posttranslational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; 10801 University Boulevard, Manassas, Va. 20110-2209) and can be chosen to ensure the correct modification and processing of the foreign protein.

Stable expression is preferred for long-term, high yield production of recombinant proteins. For example, cell lines which stably express AMPD polypeptides can be transformed using expression vectors which can contain viral origins of replication and/or endogenous expression elements and a selectable marker gene on the same or on a separate vector. Following the introduction of the vector, cells can be allowed to grow for 12 days in an enriched medium before they are switched to a selective medium. The purpose of the selectable marker is to confer resistance to selection, and its presence allows growth and recovery of cells which successfully express the introduced AMPD sequences. Resistant clones of stably transformed cells can be proliferated using tissue culture techniques appropriate to the cell type. See, for example, ANIMAL CELL CULTURE, R. I. Freshney, ed., 1986.

Detecting Expression

A variety of protocols for detecting and measuring the expression of an AMPD polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a KHK polypeptide can be used, or a competitive binding assay can be employed. These and other assays are described in Hampton et al., SEROLOGICAL METHODS: A LABORATORY MANUAL, APS Press, St. Paul, Minn., 1990) and Maddox et al., J. Exp. Med. 158, 12111216, 1983).

Expression and Purification of Polypeptides

Host cells transformed with nucleotide sequences encoding AMPD polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode KHK polypeptides can be designed to contain signal sequences which direct secretion of soluble AMPD polypeptides through a prokaryotic or eukaryotic cell membrane or which direct the membrane insertion of membrane-bound AMPD polypeptide.

Antibodies

Antibodies are referenced herein and various aspects of the subject invention utilize antibodies specific to AMPD polypeptide(s). As described above, one example of a therapeutic agent may pertain to an antibody. Any type of antibody known in the art can be generated to bind specifically to an epitope of an AMPD polypeptide. "Antibody" as used herein includes intact immunoglobulin molecules, as well as fragments thereof, which are capable of binding an epitope of an AMPD polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of an AMPD polypeptide can be used therapeutically, as mentioned, as well as in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen. Antibodies useful for embodiments of the subject invention may be polyclonal, but are preferably monoclonal antibodies.

Ribozymes

Ribozymes may be one category of compounds useful as therapeutic agents for modulating AMDP activity. Ribozymes are RNA molecules with catalytic activity. See, e.g., Cech, Science 236, 15321539; 1987; Cech, Ann. Rev. Biochem. 59, 543568; 1990, Cech, Curr. Opin. Struct. Biol. 2, 605609; 1992, Couture & Stinchcomb, Trends Genet. 12, 510515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

Accordingly, another aspect of the invention pertains to using the coding sequence of an AMPD polynucleotide to generate ribozymes which will specifically bind to mRNA transcribed from the AMPD polynucleotide. Methods of designing and constructing ribozymes which can cleave other RNA molecules in trans in a highly sequence specific manner have been developed and described in the art (see Haseloff et al. Nature 334, 585591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within an AMPD RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate AMPD RNA targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease AMPD expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, the entirety of which is incorporated by reference, ribozymes can be engineered so that ribozyme expression will occur in response to factors which induce expression of a target gene. Ribozymes also can be engineered to provide an additional level of regulation, so that destruction of mRNA occurs only when both a ribozyme and a target gene are induced in the cells.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989); Methods in Plant Molecular Biology, Maliga et al, Eds., Cold Spring Harbor Laboratory Press, New York (1995); Arabidopsis, Meyerowitz et al, Eds., Cold Spring Harbor Laboratory Press, New York (1994) and the various references cited therein.

Interfering Molecules

AMPD can be inhibited by a number of means including silencing via miRNA, shRNA, or siRNA, for example, directed to a portion of the sequence described at the genbank accession numbers provided above. siRNA molecules can be prepared against a portion of SEQ ID NOs: 1, 2, 3, 4, 5, 6 according to the techniques provided in U.S Patent Publication 20060110440 and used as therapeutic compounds. RNAi against AMPD is commercially available from, for example, Santa Cruz Biotechnology, including AMPD2 siRNA (catalog #sc-78844), AMPD2 shRNA plasmid (catalog #sc-78844-SH), AMPD2 shRNA lentiviral particles (catalog #sc-78844-V), in non limiting examples. shRNA constructs are typically made from one of three possible methods; (i) annealed complementary oligonucleotides, (ii) promoter based PCR or (iii) primer extension. See Design and cloning strategies for constructing shRNA expression vectors, Glen J McIntyre, Gregory C Fanning BMC Biotechnology 2006, 6:1 (5 Jan. 2006).

For background information on the preparation of miRNA molecules, see e.g. U.S. patent applications 20110020816, 2007/0099196; 2007/0099193; 2007/0009915; 2006/0130176; 2005/0277139; 2005/0075492; and 2004/0053411, the disclosures of which are hereby incorporated by reference herein. See also, U.S. Pat. Nos. 7,056,704 and 7,078,196 (preparation of miRNA molecules), incorporated by reference herein. Synthetic miRNAs are described in Vatolin, et al 2006 J Mol Biol 358, 983-6 and Tsuda, et al 2005 Int J Oncol 27, 1299-306, incorporated by reference herein.

It is within the scope of aspects of the present invention to provide agents to silence AMPD2 genes to achieve a therapeutic effect using interfering molecules.

Exemplary AMPD2 Inhibitor Compounds

To document that small molecule compounds are available to inhibit AMPD2 specifically, the present inventors proposed the following compounds and the following scheme to arrive at the compound below:
AMPD2 inhibitors provided
in Admyre et al.(supra)
B

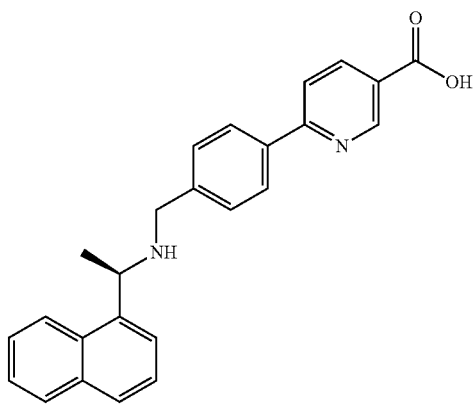
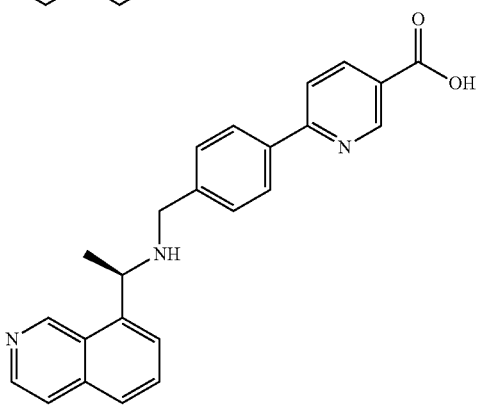
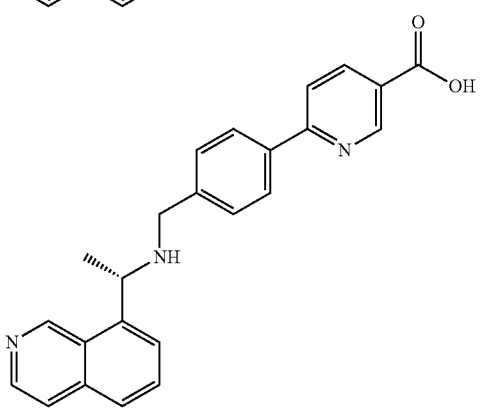
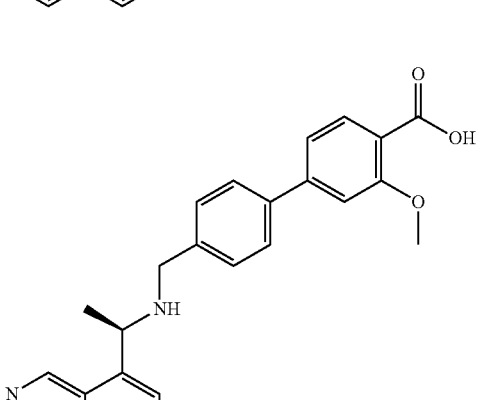
In a particular embodiment, the AMPD inhibitor is as follows:
| | |
|---|---|
| Proposal | (S)-6-(4-((1-(isoquinolin-8-yl)ethylamino)methyl)phenyl)nicotinic acid |
| Structure | 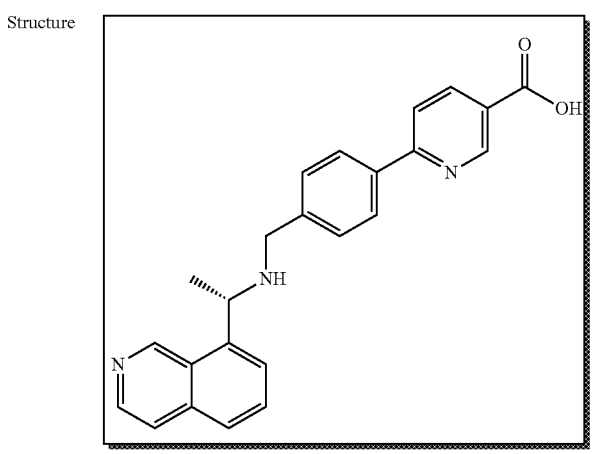 |
| Quantity | ~50 mg |
Proposed Scheme:
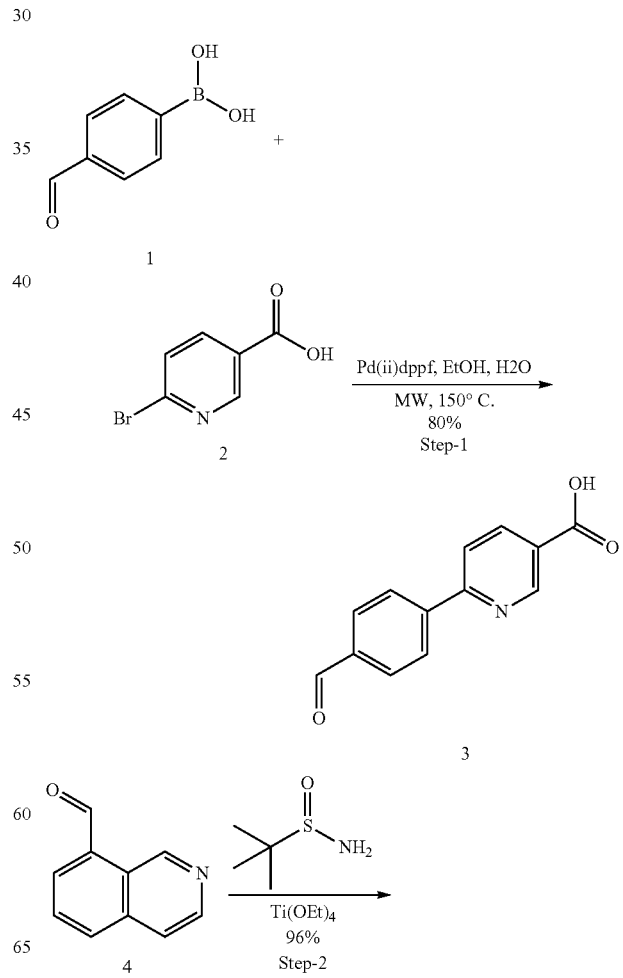

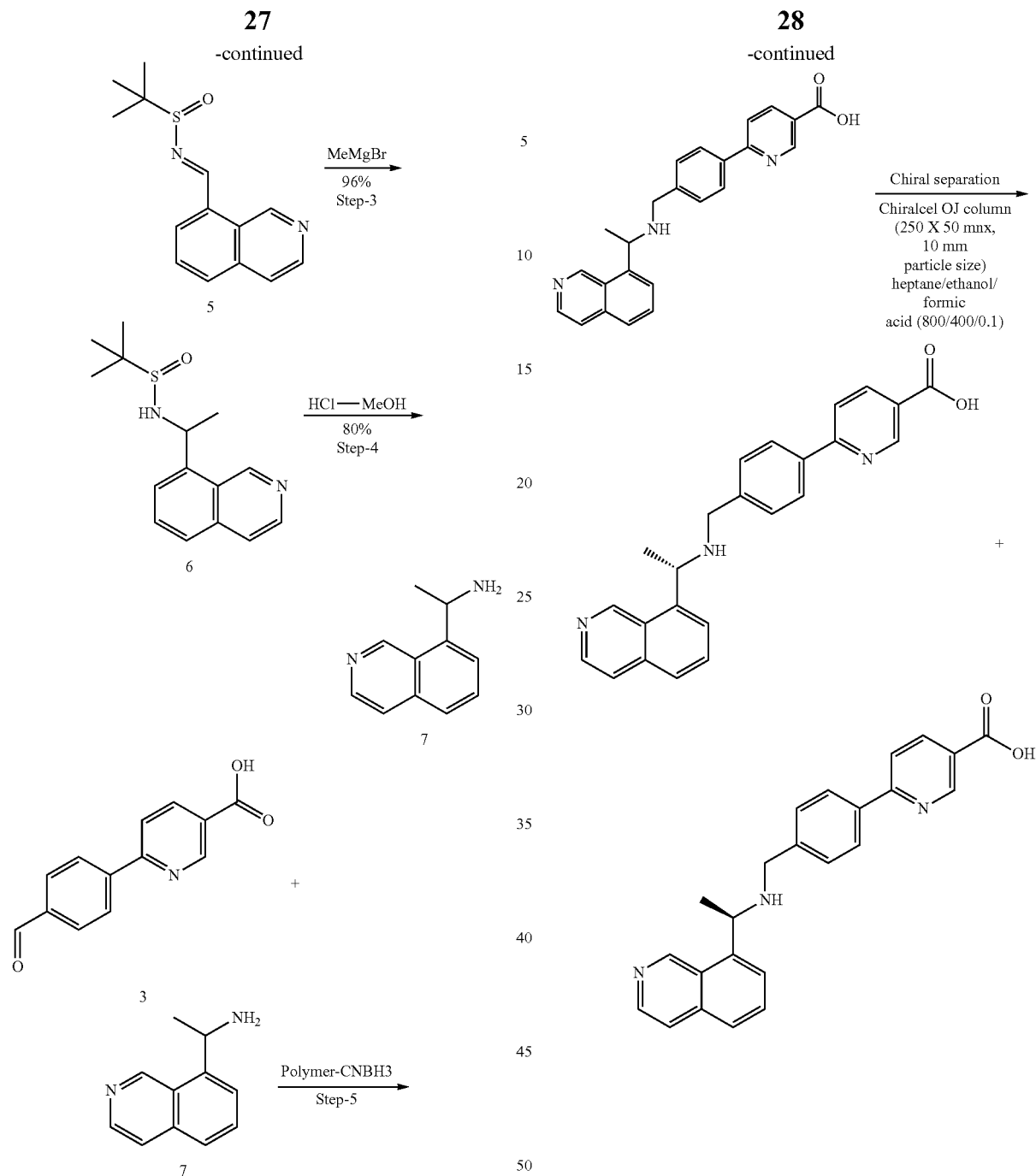
| S. No. | Chemical Name | CAS No. | Vendor | Quantity | Cost ($) |
|---|---|---|---|---|---|
| 1 | 4-formylphenylboronic acid | 87199-17-5 | Sigma-Aldrich | 10 g | 205 |
| 2 | 6-bromonicotinic acid | 6311-35-9 | Sigma-Aldrich | 10 g | 225 |
| 3 | 1,1'-bis(diphenylphosphino)-ferrocenedichloropalladium(II) | 72287-26-4 | Sigma-Aldrich | 5 g | 255 |
| 4 | isoquinoline-8-carbaldehyde | | Sigma-Aldrich | | |
| 5 | Titanium ethoxide | 3087-36-3 | Sigma-Aldrich | 50 g | 55 |
| 6 | 2-methylpropane-2-sulfinamide (racemic) | 146374-27-8 | Sigma-Aldrich | 5 g | 193 |

| S. No. | Chemical Name | CAS No. | Vendor | Quantity | Cost ($) |
|---|---|---|---|---|---|
| 7 | Methylmagnesium bromide 3M | 75-16-1 | Sigma-Aldrich | 100 ml | 48 |
| 8 | Polymer supported cyanoborohydride Chiralcel OJ column (250 × 50 mm; 10 μm particle size) heptane/ethanol/formic acid (60/40/0.1) | | Sigma-Aldrich | 25 g | 268 |

Derivatives of AMPD2 Inhibitors

According to certain embodiments, the term AMPD2 inhibitors may include derivatives, salts, esters, enol ethers, enol esters, acetals, ketals, orthoesters, hemiacetals, hemiketals, solvates, hydrates, metabolites or prodrugs thereof. Derivatives may be readily prepared by those of skill in this art using known methods for such derivatization. (see also, Admyre et al cited supra, which describes different derivatives of the compounds described above, particularly those shown in FIG. 2A). The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, alk(en)(yn)yl, aryl, aralkyl, and cycloalkyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, alk(en)(yn)yl, aryl, aralkyl, or cycloalkyl. Pharmaceutically acceptable enol esters include, but are not limited to, derivatives of formula C=C(OC(O)R) where R is hydrogen, alkyl, alkenyl, alkynyl, aryl, aralkyl, or cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

According to further embodiments, derivatives may include, but are not limited to, specific substitutions of reactive constituents on or emanating from the AMPD2 inhibitor, and may include, but are not limited to, one or more of the following: a hydrogen, hydroxy, halo, haloalkyl, thiocarbonyl, alkoxy, alkenoxy, alkylaryloxy, aryloxy, arylalkyloxy, cyano, nitro, imino, alkylamino, aminoalkyl, thio, sulfhydryl, thioalkyl, alkylthio, sulfonyl, C1-C6 straight or branched chain alkyl, C2-C6 straight or branched chain alkenyl or alkynyl, aryl, aralkyl, heteroaryl, carbocycle, or heterocycle group or moiety, or CO2 R7 where R7 is hydrogen or C1-C9 straight or branched chain alkyl or C2-C9 straight or branched chain alkenyl group or moiety.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, alkyl refers to an unbranched or branched hydrocarbon chain. An alkyl group may be unsubstituted or substituted with one or more heteroatoms.

As used herein, alkenyl refers to an unbranched or branched hydrocarbon chain comprising one or more double bonds. The double bond of an alkenyl group may be unconjugated or conjugated to another unsaturated group. An alkenyl group may be unsubstituted or substituted with one or more heteroatoms.

As used herein, alkynyl refers to an unbranched or branched hydrocarbon chain comprising one of more triple bonds therein. The triple bond of an alkynyl group may be unconjugated or conjugated to another unsaturated group. An alkynyl group may be unsubstituted or substituted with one or more heteroatoms.

As used herein, alk(en)(yn)yl refers to an unbranched or branched hydrocarbon group comprising at least one double bond and at least one triple bond. The double bond or triple bond of an alk(en)(yn)yl group may be unconjugated or conjugated to another unsaturated group. An alk(en)(yn)yl group may be unsubstituted or substituted with one or more heteroatoms. Exemplary alkyl, alkenyl, alkynyl, and alk(en)(yn)yl groups herein include, but are not limited to, methyl, ethyl, propyl, isopropyl, isobutyl, n-butyl, sec-butyl, tert-butyl, isopentyl, neopentyl, tert-pentyl, isohexyl, allyl (propenyl) and propargyl (propynyl).

As used herein, "aryl" refers to aromatic monocyclic or multicyclic groups containing from 6 to 19 carbon atoms. Aryl groups include, but are not limited to groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl or isoquinolinyl.

As used herein, "halo," "halogen," or "halide" refers to F, Cl, Br or I.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

REFERENCES

References cited by parenthetical numbers are as follows:
1. Rada P, Avena N M, Hoebel B G. Daily bingeing on sugar repeatedly releases dopamine in the accumbens shell. Neuroscience. 2005; 134(3):737-44.
2. Avena N M, Rada P, Hoebel B G. Evidence for sugar addiction: behavioral and neurochemical effects of intermittent, excessive sugar intake. Neurosci Biobehav Rev. 2008; 32(1):20-39.
3. Colantuoni C, Rada P, McCarthy J, Patten C, Avena N M, Chadeayne A, et al. Evidence that intermittent, excessive sugar intake causes endogenous opioid dependence. Obes Res. 2002; 10(6):478-88.
4. Avena N M, Bocarsly M E, Rada P, Kim A, Hoebel B G. After daily bingeing on a sucrose solution, food deprivation induces anxiety and accumbens dopamine/acetylcholine imbalance. Physiol Behav. 2008; 94(3):309-15.
5. Johnson R J, Gold M S, Johnson D R, Ishimoto T, Lanaspa M, Zahniser N R, et al. Attention Deficit-Hyperactivity Disorder: Is It Time to Reappraise the Role of Sugar Consumption? Postgraduate Med. 2011:in press.
6. Stice E, Yokum S, Blum K, Bohon C. Weight gain is associated with reduced striatal response to palatable food. J Neurosci. 2010; 30(39):13105-9.
7. Volkow N D, Wang G J, Kollins S H, Wigal T L, Newcorn J H, Telang F, et al. Evaluating dopamine reward pathway in ADHD: clinical implications. JAMA. 2009; 302(10):1084-91.
8. Blumenthal D M, Gold M S. Neurobiology of food addiction. Curr Opin Clin Nutr Metab Care. 2010; 13(4):359-65.
9. Stephan B C, Wells J C, Brayne C, Albanese E, Siervo M. Increased fructose intake as a risk factor for dementia. J Gerontol A Biol Sci Med Sci. 2010; 65(8):809-14.
10. Moore S C, Carter L M, van Goozen S. Confectionery consumption in childhood and adult violence. Br J Psychiatry. 2009; 195(4):366-7.
11. Johnson R J, Gold M S, Johnson D R, Ishimoto T, Lanaspa M A, Zahniser N R, et al. Attention-deficit/hyperactivity disorder: is it time to reappraise the role of sugar consumption?Postgrad Med. 2011; 123(5):39-49.
12. Avena N M, Rada P, Hoebel B G. Sugar bingeing in rats. Curr Protoc Neurosci. 2006; Chapter 9:Unit9 23C.
13. Nakagawa T, Hu H, Zharikov S, Tuttle K R, Short R A, Glushakova O, et al. A causal role for uric acid in fructose-induced metabolic syndrome. Am J Physiol Renal Physiol. 2006; 290(3):F625-31.
14. de Araujo I E, Oliveira-Maia A J, Sotnikova T D, Gainetdinov R R, Caron M G, Nicolelis M A, et al. Food reward in the absence of taste receptor signaling. Neuron. 2008; 57(6):930-41.

References cited by superscript are as follows:
12. Admyre T., et al., Inhibition of AMP Deaminase Activity Does Not Improve Glucose Control in Rodent Models of Insulin Resistance or Diabetes. Chemistry & Biology 21, 1486-1496, Nov. 20, 2014.
13. Kasibhatla, Srinivas, et. al., AMP Deaminase Inhibitors. 5. Design, Synthesis, and SAR of a Highly Potent Inhibitor Series. American Chemical Society. J. Med Chem. 2001, 44, 613-618, Aug. 16, 2000.
14. Kasibhatla S R, Bookser B C, Probst G, Appleman J R, Erion M D. AMP deaminase inhibitors. 3. SAR of 3-(carboxyarylalkyl)coformycin aglycon analogues. Journal of medicinal chemistry. 2000; 43(8):1508-18.
15. Rada P, Avena N M, Hoebel B G. Daily bingeing on sugar repeatedly releases dopamine in the accumbens shell. Neuroscience. 2005; 134(3):737-44.
16. Avena N M, Rada P, Hoebel B G. Evidence for sugar addiction: behavioral and neurochemical effects of intermittent, excessive sugar intake. Neurosci Biobehav Rev. 2008; 32(1):20-39.
17. Colantuoni C, Rada P, McCarthy J, Patten C, Avena N M, Chadeayne A, et al. Evidence that intermittent, excessive sugar intake causes endogenous opioid dependence. Obes Res. 2002; 10(6):478-88.
18. Avena N M, Bocarsly M E, Rada P, Kim A, Hoebel B G. After daily bingeing on a sucrose solution, food deprivation induces anxiety and accumbens dopamine/acetylcholine imbalance. Physiology & behavior. 2008; 94(3):309-15.
19. Johnson R J, Gold M S, Johnson D R, Ishimoto T, Lanaspa M, Zahniser N R, et al. Attention Deficit-Hyperactivity Disorder: Is It Time to Reappraise the Role of Sugar Consumption? Postgraduate Med. 2011:in press.
20. Stice E, Yokum S, Blum K, Bohon C. Weight gain is associated with reduced striatal response to palatable food. J Neurosci. 2010; 30(39):13105-9.
21. Volkow N D, Wang G J, Kollins S H, Wigal T L, Newcorn J H, Telang F, et al. Evaluating dopamine reward pathway in ADHD: clinical implications. JAMA. 2009; 302(10):1084-91.
22. Blumenthal D M, Gold M S. Neurobiology of food addiction. Curr Opin Clin Nutr Metab Care. 2010; 13(4):359-65.
23. Stephan B C, Wells J C, Brayne C, Albanese E, Siervo M. Increased fructose intake as a risk factor for dementia. J Gerontol A Biol Sci Med Sci. 2010; 65(8):809-14.
24. Moore S C, Carter L M, van Goozen S. Confectionery consumption in childhood and adult violence. Br J Psychiatry. 2009; 195(4):366-7.
25. Johnson R J, Gold M S, Johnson D R, Ishimoto T, Lanaspa M A, Zahniser N R, et al. Attention-deficit/hyperactivity disorder: is it time to reappraise the role of sugar consumption?Postgraduate medicine. 2011; 123(5):39-49.
26. Cicerchi C, Li N, Kratzer J, Garcia G, Roncal-Jimenez C A, Tanabe K, et al. Uric acid-dependent inhibition of AMP kinase induces hepatic glucose production in diabetes and starvation: evolutionary implications of the uricase loss in hominids. FASEB journal: official publication of the Federation of American Societies for Experimental Biology. 2014; 28(8):3339-50.
27. Lanaspa M A, Cicerchi C, Garcia G, Li N, Roncal-Jimenez C A, Rivard C J, et al. Counteracting Roles of AMP Deaminase and AMP Kinase in the Development of Fatty Liver. PloS one. 2012; 7(11):e48801.
28. Lanaspa M A, Epperson L E, Li N, Cicerchi C, Garcia G E, Roncal-Jimenez C A, et al. Opposing activity changes in AMP deaminase and AMP-activated protein kinase in the hibernating ground squirrel. PloS one. 2015; 10(4):e0123509.
29. Nakagawa T, Hu H, Zharikov S, Tuttle K R, Short R A, Glushakova 0, et al. A causal role for uric acid in fructose-induced metabolic syndrome. American journal of physiology Renal physiology. 2006; 290(3):F625-31.
30. Avena N M, Rada P, Hoebel B G. Sugar bingeing in rats. Curr Protoc Neurosci. 2006; Chapter 9:Unit9 23C.
31. de Araujo I E, Oliveira-Maia A J, Sotnikova T D, Gainetdinov R R, Caron M G, Nicolelis M A, et al. Food reward in the absence of taste receptor signaling. Neuron. 2008; 57(6):930-41.
32. von Holstein-Rathlou S, BonDurant L D, Peltekian L, Naber M C, Yin T C, Claflin K E, et al. FGF21 Mediates Endocrine Control of Simple Sugar Intake and Sweet Taste Preference by the Liver. Cell Metab. 2016; 23(2): 335-43.

The teachings of the references, including patents and patent related documents, cited herein are incorporated herein in their entirety to the extent not inconsistent with the teachings herein.

```
SEQUENCE INFORMATION:
(Pub Med Accession #NM_001257360):
                                                          SEQ. ID. NO. 1
   1 gcggggccag gcggggcgg ggccaagggc cgcagagcct ggcgcggagc cggcgagatt 61 ttggtggggt ctcacctgtt gcgtgactcc cccacagtcc ggccgcggga gtccgaccct 121 gaatgcccag ggagtgttga gagaaatctg gacgagtttc gggtcccgct cccttgggag 181 cacgtggcct accagcctct cgattgcagg gttgggtggt cgcgacaccg gggtcgcctt 241 gaggccagtc cggctgccga ggtctgcggg agtccacctc cggccagctg gcaattttga 301 aagactgcct tactttcccc atctcagtgc cagggcaggg gcccttggag tgacttggct 361 ggggtctgtg gcccgatccc cctgccgtcc ctcaggaccc gggctttctg ctgtacagac 421 ttctcgtggg cagcctcccc tcggaactcg ggcatcatgg cctcaggccc agccaccatc 481 agtcacgtca ctcctgggac tgaggaggca ggggagggat aaggggcaga gatggaggcc 541 ccactcccg aggttgccta gacaacatga gaaatcgtgg ccagggcctc ttccgcctgc 601 ggagccgctg cttcctgcat cagtcactcc cgctggggc ggggcggagg aaggggttgg 661 atgtggcaga gccaggcccc agccggtgcc gctcagactc ccccgctgtc gccgccgtgg 721 tcccagccat ggcatcctat ccatctggct ctggcaagcc caaggccaaa tatcccttta 781 agaagcgggc cagcctgcag gcctccactg cagctccaga ggctcggggt ggtctggggg 841 ccctccgct gcagtctgcc cgatccctgc cgggccccgc ccctgcctc aagcacttcc 901 cgctcgacct gcgcacgtct atggatggca aatgcaagga gatcgccgag gagctgttca 961 cccgctcact ggctgagagc gagctccgta gtgccccgta tgagttcccc gaggagagcc 1021 ccattgaaca gctggaggag cggcggcagc ggctggagcg gcagatcagc caggatgtca 1081 agctggagcc agacatcctg cttcgggcca agcaagattt cctgaagacg gacagtgact 1141 cggacctaca gctctacaag gaacagggtg aggggcaggg tgaccggagc ctgcgggagc 1201 gtgatgtgct ggaacgggag tttcagcggg tcaccatctc tggggaggag aagtgtgggg 1261 tgccgttcac agacctgctg gatgcagcca agagtgtggt gcgggcgctc ttcatccggg 1321 agaagtacat ggccctgtcc ctgcagagct tctgccccac caccgccgc tacctgcagc 1381 agctggctga aaagcctctg gagacccgga cctatgaaca gggccccgac accctgtgt 1441 ctgctgatgc cccggtgcac ccccctgcgc tggagcagca cccgtatgag cactgtgagc 1501 caagcaccat gcctgggac ctgggcttgg gtctgcgcat ggtgcgggt gtggtgcacg 1561 tctacacccg cagggaaccc gacgagcatt gctcagaggt ggagctgcca taccctgacc 1621 tgcaggaatt tgtggctgac gtcaatgtgc tgatggccct gattatcaat ggccccataa 1681 agtcattctg ctaccgccgg ctgcagtacc tgagctccaa gttccagatg catgtgctac 1741 tcaatgagat gaaggagctg gccgcccaga agaaagtgcc acccgagat ttctacaaca 1801 tccgcaaggt ggacacccac atccatgcct cgtcctgcat gaaccagaag catctgctgc
```

-continued

```
1861 gcttcatcaa gcgggcaatg aagcggcacc tggaggagat cgtgcacgtg gagcagggcc
1921 gtgaacagac gctgcgggag gtctttgaga gcatgaatct cacggcctac gacctgagtg
1981 tggacacgct ggatgtgcat gcggacagga acactttcca tcgctttgac aagtttaatg
2041 ccaaatacaa ccctattggg gagtccgtcc tccgagagat cttcatcaag acggacaaca
2101 gggtatctgg gaagtacttt gctcacatca tcaaggaggt gatgtcagac ctggaggaga
2161 gcaaatacca gaatgcagag ctgcggctct ccatttacgg gcgctcgagg gatgagtggg
2221 acaagctggc gcgctgggcc gtcatgcacc gcgtgcactc ccccaacgtg cgctggctgg
2281 tgcaggtgcc ccgcctcttt gatgtgtacc gtaccaaggg ccagctggcc aacttccagg
2341 agatgctgga gaacatcttc ctgccactgt tcgaggccac tgtgcaccct gccagccacc
2401 cggaactgca tctcttctta gagcacgtgg atggttttga cagcgtggat gatgagtcca
2461 agcctgaaaa ccatgtcttc aacctggaga gcccctgcc tgaggcgtgg gtggaggagg
2521 acaacccacc ctatgcctac tacctgtact acacctttgc caacatggcc atgttgaacc
2581 acctgcgcag gcagaggggc ttccacacgt tgtgctgag gccacactgt ggggaggctg
2641 ggcccatcca ccacctggtg tcagccttca tgctggctga gaacatttcc cacgggctcc
2701 ttctgcgcaa ggcccccgtc ctgcagtacc tgtactacct ggcccagatc ggcatcgcca
2761 tgtctccgct cagcaacaac agcctcttcc tcagctatca ccggaatccg ctaccggagt
2821 acctgtcccg cggcctcatg gtctccctgt ccactgatga tcccttgcag ttccacttca
2881 ccaaggagcc gctgatggag gagtacagca tcgccaccca ggtgtggaag ctcagctcct
2941 gcgatatgtg tgagctggcc cgcaacagcg tgctcatgag cggcttctcg cacaaggtaa
3001 agagccactg gctgggaccc aactatacca aggaaggccc tgaggggaat gacatccgcc
3061 ggaccaatgt gccagacatc cgcgtgggct accgctacga gaccctgtgc caggagctgg
3121 cgctcatcac gcaggcagtc cagagtgaga tgctggagac cattccagag gaggcgggta
3181 tcaccatgag cccagggcct caatgagcct ggtccatgaa gtgcccacca catcgcagca
3241 cttttaccac gttttgtcct cagaccccgc ccatgctgtg tggtctctgc atgtctccat
3301 tcttctctgt ctctgtcttg catgtctcct accatgtcac tgtccctggg ccacccagtg
3361 aaagcaaagc ctgggaatct gctcattgtt gtttgggctc aggtattgag cctgatggcc
3421 caggtattga gggcctcccc tgctggtggc cctgtcctgg gatcctcaga agcctgactg
3481 tcctatgggc ttctccagtg tccacagggg cttgggatgg ttgtgggggg ctggcccctc
3541 tagccttttcc ggtccttcct gggcaaatct aagccttggc cagggccgaa gtttaggccc
3601 ctgtcttgtt catgtagccg aggggcaggc gggggacctc tacacctctg ctgtgggcac
3661 ggggctgctg agggtctgtg gaactccagc agctctgcac tgggtagagc tgggcctaga
3721 gctcagtcac aggcctgggc ttcctggcct gagtgggtag acgcaggcgg cagaggtgct
3781 ggaccacatc tccgccaagt cactgcccag cagccttctc cgtcctgtcc ccagcccacg
3841 tgctccttgg gtgtcagctt cctgtgcctc tgtgggagag ggcagctgcc ttgtgttatg
3901 tctgggccca cagttgctgc aaagtcctgg atctgccact caaccccggg agtggtgttc
3961 ccagtgtggc tcccagagct ttgaccagat tgtgatccca gctggcccct atgttgtgtt
4021 ctggactgag gcctttgctg tgaactgcag tgtttcatac gaaccatctt tcctagtgca
4081 tgagaaataa agattatttta agtaatgaga aaaaaaaaaa aaaaaaaaaa aaaaaaaa
```

(NM_004037):

SEQ. ID. NO 2

```
   1 gattctcggt tcttccccct cctcccagag ctgggctacc ccgggagctg agggtcagat
```

-continued

```
  61 gtggaaggaa agtgggtgct gggttttcac ggagtatgcc tgccctgccc cgggaggact
 121 gtgtttgagc ttggactcgc tcgctgctga attcctgttt gttattcttt tttcttccag
 181 gctagctgga aggaccagct agcctggact ttggcttctt tgcccgggag ccctggcatg
 241 atggggtgag ggctcttggt gggttagtgg agagctgggg gctggcccct ccccatcttc
 301 ttttctaccc acccccctccc cgccccccgc caggcccagc caccatcagt cacgtcactc
 361 ctgggactga ggaggcaggg gagggataag gggcagagat ggaggcccca ctccccgagg
 421 ttgcctagac aacatgagaa atcgtggcca gggcctcttc cgcctgcgga gccgctgctt
 481 cctgcatcag tcactcccgc tggggcgggg cggaggaag gggttggatg tggcagagcc
 541 aggccccagc cggtgccgct cagactcccc cgctgtcgcc gccgtggtcc cagccatggc
 601 atcctatcca tctggctctg gcaagcccaa ggccaaatat ccctttaaga agcgggccag
 661 cctgcaggcc tccactgcag ctccagaggc tcggggtggt ctgggggccc ctccgctgca
 721 gtctgcccga tccctgccgg gccccgcccc ctgcctcaag cacttcccgc tcgacctgcg
 781 cacgtctatg gatggcaaat gcaaggagat cgccgaggag ctgttcaccc gctcactggc
 841 tgagagcgag ctccgtagtg ccccgtatga gttccccgag gagagcccca ttgaacagct
 901 ggaggagcgg cggcagcggc tggagcggca gatcagccag gatgtcaagc tggagccaga
 961 catcctgctt cgggccaagc aagatttcct gaagacggac agtgactcgg acctacagct
1021 ctacaaggaa cagggtgagg ggcagggtga ccggagcctg cggagcgtg atgtgctgga
1081 acgggagttt cagcgggtca ccatctctgg ggaggagaag tgtgggtgc cgttcacaga
1141 cctgctggat gcagccaaga gtgtggtgcg ggcgctcttc atccgggaga agtacatggc
1201 cctgtccctg cagagcttct gccccaccac ccgccgctac ctgcagcagc tggctgaaaa
1261 gcctctggag acccggacct atgaacaggg ccccgacacc cctgtgtctg ctgatgcccc
1321 ggtgcacccc cctgcgctgg agcagcaccc gtatgagcac tgtgagccaa gcaccatgcc
1381 tggggacctg gcttgggtc tgcgcatggt gcggggtgtg gtgcacgtct acacccgcag
1441 ggaacccgac gagcattgct cagaggtgga gctgccatac cctgacctgc aggaatttgt
1501 ggctgacgtc aatgtgctga tggccctgat tatcaatggc cccataaagt cattctgcta
1561 ccgccggctg cagtacctga gctccaagtt ccagatgcat gtgctactca atgagatgaa
1621 ggagctggcc gcccagaaga aagtgccaca ccgagatttc tacaacatcc gcaaggtgga
1681 cacccacatc catgcctcgt cctgcatgaa ccagaagcat ctgctgcgct tcatcaagcg
1741 ggcaatgaag cggcacctgg aggagatcgt gcacgtggag cagggccgtg aacagacgct
1801 gcgggaggtc tttgagagca tgaatctcac ggcctacgac ctgagtgtgg acacgctgga
1861 tgtgcatgcg gacaggaaca ctttccatcg ctttgacaag tttaatgcca aatacaaccc
1921 tattggggag tccgtcctcc gagagatctt catcaagacg gacaacaggg tatctgggaa
1981 gtactttgct cacatcatca aggaggtgat gtcagacctg gaggagagca ataccagaa
2041 tgcagagctg cggctctcca tttacgggcg ctcgaggat gagtgggaca gctggcgcg
2101 ctgggccgtc atgcaccgcg tgcactcccc caacgtgcgc tggctggtgc aggtgccccg
2161 cctctttgat gtgtaccgta ccaagggcca gctggcaac ttccaggaga tgctggagaa
2221 catcttcctg ccactgttcg aggccactgt gcaccctgcc agccacccgg aactgcatct
2281 cttcttagag cacgtggatg gttttgacag cgtggatgat gagtccaagc tgaaaaacca
2341 tgtcttcaac ctggagagcc ccctgcctga ggcgtgggtg gaggaggaca acccacccta
2401 tgcctactac ctgtactaca cctttgccaa catggccatg ttgaaccacc tgcgcaggca
2461 gaggggcttc cacacgtttg tgctgaggcc acactgtggg gaggctgggc ccatccacca
```

-continued

```
2521 cctggtgtca gccttcatgc tggctgagaa catttcccac gggctccttc tgcgcaaggc
2581 ccccgtcctg cagtacctgt actacctggc ccagatcggc atcgccatgt ctccgctcag
2641 caacaacagc ctcttcctca gctatcaccg gaatccgcta ccggagtacc tgtcccgcgg
2701 cctcatggtc tccctgtcca ctgatgatcc cttgcagttc cacttcacca aggagccgct
2761 gatggaggag tacagcatcg ccacccaggt gtggaagctc agctcctgcg atatgtgtga
2821 gctggcccgc aacagcgtgc tcatgagcgg cttctcgcac aaggtaaaga gccactggct
2881 gggacccaac tataccaagg aaggccctga ggggaatgac atccgccgga ccaatgtgcc
2941 agacatccgc gtgggctacc gctacgagac cctgtgccag gagctggcgc tcatcacgca
3001 ggcagtccag agtgagatgc tggagaccat tccagaggag gcgggtatca ccatgagccc
3061 agggcctcaa tgagcctggt ccatgaagtg cccaccacat cgcagcactt ttaccacgtt
3121 ttgtcctcag accccgccca tgctgtgtgg tctctgcatg tctccattct tctctgtctc
3181 tgtcttgcat gtctcctacc atgtcactgt ccctgggcca cccagtgaaa gcaaagcctg
3241 ggaatctgct cattgttgtt tgggctcagg tattgagcct gatggcccag gtattgaggg
3301 cctcccctgc tggtggccct gtcctgggat cctcagaagc ctgactgtcc tatgggcttc
3361 tccagtgtcc acaggggctt gggatggttg tggggggctg gcccctctag cctttccggt
3421 ccttcctggg caaatctaag ccttggccag ggccgaagtt taggcccctg tcttgttcat
3481 gtagccgagg ggcaggcggg ggacctctac acctctgctg tgggcacggg gctgctgagg
3541 gtctgtggaa ctccagcagc tctgcactgg gtagagctgg gcctagagct cagtcacagg
3601 cctgggcttc ctggcctgag tgggtagacg caggcggcag aggtgctgga ccacatctcc
3661 gccaagtcac tgcccagcag ccttctccgt cctgtcccca gcccacgtgc tccttgggtg
3721 tcagcttcct gtgcctctgt gggagagggc agctgccttg tgttatgtct ggggccacag
3781 ttgctgcaaa gtcctggatc tgccactcaa ccccggagt ggtgttccca gtgtggctcc
3841 cagagctttg accagattgt gatcccagct ggcccctatg ttgtgttctg gactgaggcc
3901 tttgctgtga actgcagtgt tcatacgaa ccatctttcc tagtgcatga gaaataaaga
3961 ttatttaagt aatgagaaaa aaaaaaaaaa aaaaaaaaaa aaaaa
```

(NM_139156):

SEQ ID NO. 3

```
  1 gcggggccag gcggggcgg ggccaagggc cgcagagcct ggcgcggagc cggcgagatt
 61 ttggtggggt ctcacctgtt gcgtgactcc cccacagtcc ggccgcggga gtccgaccct
121 gaatgcccag ggagtgttga gagaaatctg gacgagtttc gggtcccgct cccttgggag
181 cacgtggcct accagcctct cgattgcagg gttgggtggt cgcgacaccg gggtcgcctt
241 gaggccagtc cggctgccga ggtctgcggg agtccacctc cggccagctg caattttga
301 aagactgcct tactttcccc atctcagtgc cagggcaggg gcccttggag tgacttggct
361 ggggtctgtg gcccgatccc cctgccgtcc ctcaggaccc gggctttctg ctgtacagac
421 ttctcgtggg cagcctcccc tcggaactcg gcatcatgg cctcagaggc tcgggtggt
481 ctggggccc ctccgctgca gtctgcccga tccctgccgg ccccgcccc ctgcctcaag
541 cacttcccgc tcgacctgcg cacgtctatg gatggcaaat gcaaggagat cgccgaggag
601 ctgttcaccc gctcactggc tgagagcgag ctccgtagtg cccgtatga gttcccgag
661 gagagcccca ttgaacagct ggaggagcgg cggcagcggc tggagcggca gatcagccag
721 gatgtcaagc tggagccaga catcctgctt cgggccaagc aagatttcct gaagacggac
781 agtgactcgg acctacagct ctacaaggaa cagggtgagg ggcagggtga ccggagcctg
```

-continued

```
 841 cgggagcgtg atgtgctgga acgggagttt cagcgggtca ccatctctgg ggaggagaag 901 tgtggggtgc cgttcacaga cctgctggat gcagccaaga gtgtggtgcg ggcgctcttc 961 atccgggaga agtacatggc cctgtccctg cagagcttct gccccaccac ccgccgctac 1021 ctgcagcagc tggctgaaaa gcctctggag acccggacct atgaacaggg ccccgacacc 1081 cctgtgtctg ctgatgcccc ggtgcacccc cctgcgctgg agcagcaccc gtatgagcac 1141 tgtgagccaa gcaccatgcc tggggacctg gcttgggtc tgcgcatggt gcggggtgtg 1201 gtgcacgtct acacccgcag ggaacccgac gagcattgct cagaggtgga gctgccatac 1261 cctgacctgc aggaatttgt ggctgacgtc aatgtgctga tggccctgat tatcaatggc 1321 cccataaagt cattctgcta ccgccggctg cagtacctga gctccaagtt ccagatgcat 1381 gtgctactca atgagatgaa ggagctggcc gcccagaaga agtgccaca ccgagatttc 1441 tacaacatcc gcaaggtgga cacccacatc catgcctcgt cctgcatgaa ccagaagcat 1501 ctgctgcgct tcatcaagcg ggcaatgaag cggcacctgg aggagatcgt gcacgtggag 1561 cagggccgtg aacagacgct gcgggaggtc tttgagagca tgaatctcac ggcctacgac 1621 ctgagtgtgg acacgctgga tgtgcatgcg gacaggaaca ctttccatcg ctttgacaag 1681 tttaatgcca aatacaaccc tattggggag tccgtcctcc gagagatctt catcaagacg 1741 gacaacaggg tatctgggaa gtactttgct cacatcatca aggaggtgat gtcagacctg 1801 gaggagagca ataccagaa tgcagagctg cggctctcca tttacgggcg ctcgagggat 1861 gagtgggaca agctggcgcg ctgggccgtc atgcaccgcg tgcactcccc caacgtgcgc 1921 tggctggtgc aggtgccccg cctctttgat gtgtaccgta ccaagggcca gctggccaac 1981 ttccaggaga tgctggagaa catcttcctg ccactgttcg aggccactgt gcaccctgcc 2041 agccaccgg aactgcatct cttcttagag cacgtggatg gttttgacag cgtggatgat 2101 gagtccaagc ctgaaaacca tgtcttcaac ctggagagcc cctgcctga ggcgtgggtg 2161 gaggaggaca acccacccta tgcctactac ctgtactaca cctttgccaa catggccatg 2221 ttgaaccacc tgcgcaggca gagggcttc cacacgtttg tgctgaggcc acactgtggg 2281 gaggctgggc ccatccacca cctggtgtca gccttcatgc tggctgagaa catttcccac 2341 gggctccttc tgcgcaaggc ccccgtcctg cagtacctgt actacctggc ccagatcggc 2401 atcgccatgt ctccgctcag caacaacagc ctcttcctca gctatcaccg gaatccgcta 2461 ccggagtacc tgtcccgcgg cctcatggtc tccctgtcca ctgatgatcc cttgcagttc 2521 cacttcacca aggagccgct gatggaggag tacagcatcg ccacccaggt gtggaagctc 2581 agctcctgcg atatgtgtga gctggcccgc aacagcgtgc tcatgagcgg cttctcgcac 2641 aaggtaaaga gccactggct gggacccaac tataccaagg aaggccctga ggggaatgac 2701 atccgccgga ccaatgtgcc agacatccgc gtgggctacc gctacgagac cctgtgccag 2761 gagctggcgc tcatcacgca ggcagtccag agtgagatgc tggagaccat tccagaggag 2821 gcgggtatca ccatgagccc agggcctcaa tgagcctggt ccatgaagtg cccaccacat 2881 cgcagcactt ttaccacgtt ttgtcctcag accccgccca tgctgtgtgg tctctgcatg 2941 tctccattct tctctgtctc tgtcttgcat gtctcctacc atgtcactgt ccctgggcca 3001 cccagtgaaa gcaaagcctg gaatctgct cattgttgtt tgggctcagg tattgagcct 3061 gatggcccag gtattgaggg cctcccctgc tggtggccct gtcctgggat cctcagaagc 3121 ctgactgtcc tatgggcttc tccagtgtcc acaggggctt gggatggttg tggggggctg 3181 gcccctctag ccttttccggt ccttcctggg caaatctaag ccttggccag gccgaagtt 3241 taggcccctg tcttgttcat gtagccgagg ggcaggcggg ggacctctac acctctgctg
```

-continued

```
3301 tgggcacggg gctgctgagg gtctgtggaa ctccagcagc tctgcactgg gtagagctgg
3361 gcctagagct cagtcacagg cctgggcttc ctggcctgag tgggtagacg caggcggcag
3421 aggtgctgga ccacatctcc gccaagtcac tgcccagcag ccttctccgt cctgtcccca
3481 gcccacgtgc tccttgggtg tcagcttcct gtgcctctgt gggagagggc agctgccttg
3541 tgttatgtct ggggccacag ttgctgcaaa gtcctggatc tgccactcaa ccccgggagt
3601 ggtgttccca gtgtggctcc cagagctttg accagattgt gatcccagct ggcccctatg
3661 ttgtgttctg gactgaggcc tttgctgtga actgcagtgt tcatacgaa ccatctttcc
3721 tagtgcatga gaaataaaga ttatttaagt aatgagaaaa aaaaaaaaaa aaaaaaaaa
3781 aaaaa
```

(NM_203404):

SEQ. ID NO 4

```
   1 cgccgaggta tcacctggca ccacccgcac cctcaccccg tgtctccatg ccctgcctct
  61 gctccccaca cccctcacct caagctgtcc cctcacctca cgcttggctg tctcctgatc
 121 ctcagcctct cccaggtacc cctggtcctg ctgccctcac ccatcccca gactctgtag
 181 gagagtgccc gagggcggag ggccagccat gctgaccttc cttccctccc ccaggagct
 241 gttcacccgc tcactggctg agagcgagct ccgtagtgcc ccgtatgagt tccccgagga
 301 gagccccatt gaacagctgg aggagcggcg gcagcggctg gagcggcaga tcagccagga
 361 tgtcaagctg gagccagaca tcctgcttcg ggccaagcaa gatttcctga agacggacag
 421 tgactcggac ctacagctct acaaggaaca gggtgagggg cagggtgacc ggagcctgcg
 481 ggagcgtgat gtgctggaac gggagtttca gcgggtcacc atctctgggg aggagaagtg
 541 tggggtgccg ttcacagacc tgctggatgc agccaagagt gtggtgcggg cgctcttcat
 601 ccgggagaag tacatggccc tgtccctgca gagcttctgc ccaccaccc gccgctacct
 661 gcagcagctg gctgaaaagc ctctggagac ccggacctat gaacagggcc ccgacacccc
 721 tgtgtctgct gatgccccgg tgcaccccc tgcgctggag cagcacccgt atgagcactg
 781 tgagccaagc accatgcctg ggacctgggg cttgggtctg cgcatggtgc ggggtgtggt
 841 gcacgtctac acccgcaggg aacccgacga gcattgctca gaggtggagc tgccataccc
 901 tgacctgcag gaatttgtgg ctgacgtcaa tgtgctgatg ccctgatta tcaatggccc
 961 cataaagtca ttctgctacc gccggctgca gtacctgagc tccaagttcc agatgcatgt
1021 gctactcaat gagatgaagg agctggccgc ccagaagaaa gtgccacacc gagatttcta
1081 caacatccgc aaggtggaca cccacatcca tgcctcgtcc tgcatgaacc agaagcatct
1141 gctgcgcttc atcaagcggg caatgaagcg gcacctggag gagatcgtgc acgtggagca
1201 gggccgtgaa cagacgctgc gggaggtctt tgagagcatg aatctcacgg cctacgacct
1261 gagtgtggac acgctggatg tgcatgcgga caggaacact ttccatcgct ttgacaagtt
1321 taatgccaaa tacaacccta ttggggagtc cgtcctccga gagatcttca tcaagacgga
1381 caacagggta tctgggaagt actttgctca catcatcaag gaggtgatgt cagacctgga
1441 ggagagcaaa taccagaatg cagagctgcg gctctccatt tacggcgct cgagggatga
1501 gtgggacaag ctggcgcgct gggccgtcat gcaccgcgtg cactcccca acgtgcgctg
1561 gctggtgcag gtgccccgcc tctttgatgt gtaccgtacc aagggccagc tggccaactt
1621 ccaggagatg ctggagaaca tcttcctgcc actgttcgag gccactgtgc accctgccag
1681 ccacccggaa ctgcatctct tcttagagca cgtggatggt tttgacagcg tggatgatga
1741 gtccaagcct gaaaaccatg tcttcaacct ggagagcccc ctgcctgagg cgtgggtgga
```

-continued

```
1801 ggaggacaac ccaccctatg cctactacct gtactacacc tttgccaaca tggccatgtt
1861 gaaccacctg cgcaggcaga ggggcttcca cacgtttgtg ctgaggccac actgtgggga
1921 ggctgggccc atccaccacc tggtgtcagc cttcatgctg gctgagaaca tttcccacgg
1981 gctccttctg cgcaaggccc ccgtcctgca gtacctgtac tacctggccc agatcggcat
2041 cgccatgtct ccgctcagca acaacagcct cttcctcagc tatcaccgga atccgctacc
2101 ggagtacctg tcccgcggcc tcatggtctc cctgtccact gatgatccct tgcagttcca
2161 cttcaccaag gagccgctga tggaggagta cagcatcgcc acccaggtgt ggaagctcag
2221 ctcctgcgat atgtgtgagc tggcccgcaa cagcgtgctc atgagcggct tctcgcacaa
2281 ggtaaagagc cactggctgg acccaactac taccaaggaa ggccctgagg ggaatgacat
2341 ccgccggacc aatgtgccag acatccgcgt gggctaccgc tacgagaccc tgtgccagga
2401 gctggcgctc atcacgcagg cagtccgaag tgagatgctg agaccattc cagaggaggc
2461 gggtatcacc atgagcccag ggcctcaatg agcctggtcc atgaagtgcc caccacatcg
2521 cagcactttt accacgtttt gtcctcagac cccgcccatg ctgtgtggtc tctgcatgtc
2581 tccattcttc tctgtctctg tcttgcatgt ctcctaccat gtcactgtcc ctgggccacc
2641 cagtgaaagc aaagcctggg aatctgctca ttgttgtttg ggctcaggta ttgagcctga
2701 tggcccaggt attgagggcc tcccctgctg gtggccctgt cctgggatcc tcagaagcct
2761 gactgtccta tgggcttctc cagtgtccac aggggcttgg gatggttgtg ggggctggc
2821 ccctctagcc tttccggtcc ttcctgggca aatctaagcc ttggccaggg ccgaagttta
2881 ggccccctgtc ttgttcatgt agccgagggg caggcggggg acctctacac ctctgctgtg
2941 ggcacggggc tgctgagggt ctgtggaact ccagcagctc tgcactgggt agagctgggc
3001 ctagagctca gtcacaggcc tgggcttcct ggcctgagtg ggtagacgca ggcggcagag
3061 gtgctggacc acatctccgc caagtcactg cccagcagcc ttctccgtcc tgtccccagc
3121 ccacgtgctc cttgggtgtc agcttcctgt gcctctgtgg gagagggcag ctgccttgtg
3181 ttatgtctgg ggccacagtt gctgcaaagt cctggatctg ccactcaacc ccgggagtgg
3241 tgttcccagt gtggctccca gagctttgac cagattgtga tcccagctgg ccccctatgtt
3301 gtgttctgga ctgaggcctt tgctgtgaac tgcagtgttt catacgaacc atctttccta
3361 gtgcatgaga aataaagatt atttaagtaa tgagaaaaaa aaaaaaaaaa aaaaaaaaa
3421 aaa
```

(NM_001257361):

SEQ. ID NO. 5

```
  1 gtacagcctg tgccagcccc tgagggaccg gctgcagctt cactggcaaa caggcgggca
 61 aggggcacag ggctgctggc cggagctgcc tgcactctgc agaggctcgg ggtggtctgg
121 gggcccctcc gctgcagtct gcccgatccc tgccgggccc cgcccctgc ctcaagcact
181 tcccgctcga cctgcgcacg tctatggatg caaatgcaa ggagatcgcc gaggagctgt
241 tcacccgctc actggctgag agcgagctcc gtagtgcccc gtatgagttc cccgaggaga
301 gccccattga acagctggag gagcggcggc agcggctgga gcggcagatc agccaggatg
361 tcaagctgga gccagacatc ctgcttcggg ccaagcaaga tttcctgaag acggacagtg
421 actcggacct acagtctcta caaggaacagg gtgaggggca gggtgaccgg agcctgcggg
481 agcgtgatgt gctggaacgg gagtttcagc gggtcaccat ctctggggag gagaagtgtg
541 gggtgccgtt cacagacctg ctggatgcag ccaagagtgt ggtgcgggcg ctcttcatcc
601 gggagaagta catggccctg tccctgcaga gcttctgccc caccacccgc cgctacctgc
661 agcagctggc tgaaaagcct ctggagaccc ggacctatga acagggcccc gacacccctg
```

-continued

```
 721 tgtctgctga tgccccggtg cacccccctg cgctggagca gcacccgtat gagcactgtg
 781 agccaagcac catgcctggg gacctgggct tgggtctgcg catggtgcgg ggtgtggtgc
 841 acgtctacac ccgcagggaa cccgacgagc attgctcaga ggtggagctg ccatacgctg
 901 acctgcagga atttgtggct gacgtcaatg tgctgatggc cctgattatc aatgccccca
 961 taaagtcatt ctgctaccgc cggctgcagt acctgagctc caagttccag atgcatgtgc
1021 tactcaatga gatgaaggag ctggccgccc agaagaaagt gccacaccga gatttctaca
1081 acatccgcaa ggtggacacc cacatccatg cctcgtcctg catgaaccag aagcatctgc
1141 tgcgcttcat caagcgggca atgaagcggc acctggagga gatcgtgcac gtggagcagg
1201 gccgtgaaca gacgctgcgg gaggtctttg agagcatgaa tctcacggcc tacgacctga
1261 gtgtggacac gctggatgtg catgcggaca ggaacacttt ccatcgcttt gacaagttta
1321 atgccaaata caaccctatt ggggagtccg tcctccgaga gatcttcatc aagacggaca
1381 acagggtatc tgggaagtac tttgctcaca tcatcaagga ggtgatgtca gacctggagg
1441 agagcaaata ccagaatgca gagctgcggc tctccattta cgggcgctcg agggatgagt
1501 gggacaagct ggcgcgctgg gccgtcatgc accgcgtgca ctcccccaac gtgcgctggc
1561 tggtgcaggt gccccgcctc tttgatgtgt accgtaccaa gggccagctg ccaacttcc
1621 aggagatgct ggagaacatc ttcctgccac tgttcgaggc cactgtgcac cctgccagcc
1681 acccggaact gcatctcttc ttagagcacg tggatggttt tgacagcgtg gatgatgagt
1741 ccaagcctga aaaccatgtc ttcaacctgg agaccccct gcctgaggcg tgggtggagg
1801 aggacaaccc accctatgcc tactacctgt actacacctt tgccaacatg gccatgttga
1861 accacctgcg caggcagagg ggcttccaca cgtttgtgct gaggccacac tgtggggagg
1921 ctgggcccat ccaccacctg gtgtcagcct tcatgctggc tgagaacatt tcccacgggc
1981 tccttctgcg caaggccccc gtcctgcagt acctgtacta cctggcccag atcggcatcg
2041 ccatgtctcc gctcagcaac aacagcctct tcctcagcta tcaccggaat ccgctaccgg
2101 agtacctgtc ccgcggcctc atggtctccc tgtccactga tgatcccttg cagttccact
2161 tcaccaagga gccgctgatg gaggagtaca gcatcgccac ccaggtgtgg aagctcagct
2221 cctgcgatat gtgtgagctg gcccgcaaca gcgtgctcat gagcggcttc tcgcacaagg
2281 taaagagcca ctggctggga cccaactata ccaaggaagg ccctgagggg aatgacatcc
2341 gccggaccaa tgtgccagac atccgcgtgg gctaccgcta cgagaccctg tgccaggagc
2401 tggcgctcat cacgcaggca gtccagagtg agatgctgga gaccattcca gaggaggcgg
2461 gtatcaccat gagcccaggg cctcaatgag cctggtccat gaagtgccca ccacatcgca
2521 gcacttttac cacgttttgt cctcagaccc cgcccatgct gtgtggtctc tgcatgtctc
2581 cattcttctc tgtctctgtc ttgcatgtct cctaccatgt cactgtccct gggccaccca
2641 gtgaaagcaa agcctgggaa tctgctcatt gttgtttggg ctcaggtatt gagcctgatg
2701 gcccaggtat tgagggcctc ccctgctggt ggccctgtcc tgggatcctc agaagcctga
2761 ctgtcctatg ggcttctcca gtgtccacag gggcttggga tggttgtggg gggctggccc
2821 ctctagcctt tccggtcctt cctgggcaaa tctaagcctt ggccagggcc gaagtttagg
2881 cccctgtctt gttcatgtag ccgaggggca ggcggggac ctctacacct ctgctgtggg
2941 cacggggctg ctgagggtct gtggaactcc agcagctctg cactgggtag agctgggcct
3001 agagctcagt cacaggcctg ggcttcctgg cctgagtggg tagacgcagg cggcagaggt
3061 gctggaccac atctccgcca agtcactgcc cagcagcctt ctccgtcctg tccccagccc
```

-continued

```
3121 acgtgctcct tgggtgtcag cttcctgtgc ctctgtggga gagggcagct gccttgtgtt 3181 atgtctgggg ccacagttgc tgcaaagtcc tggatctgcc actcaaccc gggagtggtg 3241 ttcccagtgt ggctcccaga gctttgacca gattgtgatc ccagctggcc cctatgttgt 3301 gttctggact gaggcctttg ctgtgaactg cagtgtttca tacgaaccat ctttcctagt 3361 gcatgagaaa taaagattat ttaagtaatg agaaaaaaaa aaaaaaaaa aaaaaaaaa 3421 a
```

(NM_001308170):

SEQ. ID NO 6

```
   1 gcccagccac catcagtcac gtcactcctg ggactgagga ggcaggggag ggataagggg 61 cagagatgga ggccccactc cccgaggttg cctagacaac atgagaaatc gtggccaggg 121 cctcttccgc ctgcggagcc gctgcttcct gcatcagtca ctcccgctgg ggcggggcg 181 gaggaagggg ttggatgtgg cagagccagg ccccagccgg tgccgctcag actccccgc 241 tgtcgccgcc gtggtcccag ccatggcatc ctatccatct ggctctggca agcccaaggc 301 caaatatccc tttaagaagc gggccagcct gcaggcctcc actgcagctc caggagctgt 361 tcacccgctc actggctgag agcgagctcc gtagtgcccc gtatgagttc cccgaggaga 421 gccccattga acagctggag gagcggcggc agcggctgga gcggcagatc agccaggatg 481 tcaagctgga gccagacatc ctgcttcggg ccaagcaaga tttcctgaag acggacagtg 541 actcggacct acagctctac aaggaacagg gtgaggggca gggtgaccgg agcctgcggg 601 agcgtgatgt gctggaacgg gagtttcagc gggtcaccat ctctggggag gagaagtgtg 661 gggtgccgtt cacagacctg ctggatgcag ccaagagtgt ggtgcgggcg ctcttcatcc 721 gggagaagta catggccctg tccctgcaga gcttctgccc caccacccgc cgctacctgc 781 agcagctggc tgaaaagcct ctggagaccc ggacctatga acagggcccc gacacccctg 841 tgtctgctga tgccccggtg cacccccctg cgctggagca gcaccgtat gagcactgtg 901 agccaagcac catgcctggg gacctgggct tgggtctgcg catggtgcgg ggtgtggtgc 961 acgtctacac ccgcagggaa cccgacgagc attgctcaga ggtggagctg ccataccctg 1021 acctgcagga atttgtggct gacgtcaatg tgctgatggc cctgattatc aatggcccca 1081 taaagtcatt ctgctaccgc cggctgcagt acctgagctc caagttccag atgcatgtgc 1141 tactcaatga gatgaaggag ctggccgccc agaagaaagt gccacaccga gatttctaca 1201 acatccgcaa ggtggacacc cacatccatg cctcgtcctg catgaaccag aagcatctgc 1261 tgcgcttcat caagcgggca atgaagcggac cctggagga gatcgtgcac gtggagcagg 1321 gccgtgaaca gacgctgcgg gaggtctttg agagcatgaa tctcacggcc tacgacctga 1381 gtgtggacac gctggatgtg catgcggaca ggaacacttt ccatcgcttt gacaagttta 1441 atgccaaata caaccctatt ggggagtccg tcctccgaga gatcttcatc aagacggaca 1501 acagggtatc tggaagtac tttgctcaca tcatcaagga ggtgatgtca gacctggagg 1561 agagcaaata ccagaatgca gagctgcggc tctccattta cgggcgctcg agggatgagt 1621 gggacaagct ggcgcgctgg gccgtcatgc accgcgtgca ctcccccaac gtgcgctggc 1681 tggtgcaggt gccccgcctc tttgatgtgt accgtaccaa gggccagctg ccaacttcc 1741 aggagatgct ggaaacatc ttcctgccac tgttcgaggc cactgtgcac cctgccagcc 1801 acccggaact gcatctcttc ttagagcacg tggatggttt tgacagcgtg gatgatgagt 1861 ccaagcctga aaaccatgtc ttcaacctgg agagccccct gcctgaggcg tgggtggagg 1921 aggacaaccc accctatgcc tactacctgt actacacctt tgccaacatg gccatgttga 1981 accacctgcg caggcagagg ggcttccaca cgtttgtgct gaggccacac tgtggggagg
```

-continued

```
2041 ctgggcccat ccaccacctg gtgtcagcct tcatgctggc tgagaacatt tcccacgggc 2101 tccttctgcg caaggccccc gtcctgcagt acctgtacta cctggcccag atcggcatcg 2161 ccatgtctcc gctcagcaac aacagcctct tcctcagcta tcaccggaat ccgctaccgg 2221 agtacctgtc ccgcggcctc atggtctccc tgtccactga tgatcccttg cagttccact 2281 tcaccaagga gccgctgatg gaggagtaca gcatcgccac ccaggtgtgg aagctcagct 2341 cctgcgatat gtgtgagctg gcccgcaaca gcgtgctcat gagcggcttc tcgcacaagg 2401 taaagagcca ctggctggga cccaactata ccaaggaagg ccctgagggg aatgacatcc 2461 gccggaccaa tgtgccagac atccgcgtgg gctaccgcta cgagaccctg tgccaggagc 2521 tggcgctcat cacgcaggca gtccagagtg agatgctgga gaccattcca gaggaggcgg 2581 gtatcaccat gagcccaggg cctcaatgag cctggtccat gaagtgccca ccacatcgca 2641 gcacttttac cacgttttgt cctcagaccc cgcccatgct gtgtggtctc tgcatgtctc 2701 cattcttctc tgtctctgtc ttgcatgtct cctaccatgt cactgtccct gggccaccca 2761 gtgaaagcaa agcctgggaa tctgctcatt gttgtttggg ctcaggtatt gagcctgatg 2821 gcccaggtat tgagggcctc ccctgctggt ggccctgtcc tgggatcctc agaagcctga 2881 ctgtcctatg ggcttctcca gtgtccacag gggcttggga tggttgtggg gggctggccc 2941 ctctagcctt tccggtcctt cctgggcaaa tctaagcctt ggccagggcc gaagtttagg 3001 cccctgtctt gttcatgtag ccgaggggca ggcggggac ctctacacct ctgctgtggg 3061 cacggggctg ctgagggtct gtggaactcc agcagctctg cactgggtag agctgggcct 3121 agagctcagt cacaggcctg gcttcctgg cctgagtggg tagacgcagg cggcagaggt 3181 gctggaccac atctccgcca agtcactgcc cagcagcctt ctccgtcctg tcccagccc 3241 acgtgctcct tgggtgtcag cttcctgtgc ctctgtggga gagggcagct gccttgtgtt 3301 atgtctgggg ccacagttgc tgcaaagtcc tggatctgcc actcaacccc gggagtggtg 3361 ttcccagtgt ggctcccaga gctttgacca gattgtgatc ccagctggcc cctatgttgt 3421 gttctggact gaggcctttg ctgtgaactg cagtgtttca tacgaaccat ctttcctagt 3481 gcatgagaaa taaagattat ttaagtaatg agaaaaaaaa aaaaaaaaa aaaaaaaaa 3541 a
```

(NP_004028):

SEQ ID NO. 7

```
  1 mrnrgqglfr lrsrcflhqs lplgagrrkg ldvaepgpsr crsdspavaa vvpamasyps 61 gsgkpkakyp fkkraslqas taapearggl gapplqsars lpgpapclkh fpldlrtsmd 121 gkckeiaeel ftrslaesel rsapyefpee spieqleerr qrlerqisqd vklepdillr 181 akqdflktds dsdlqlykeq gegqgdrslr erdvlerefq rvtisgeekc gvpftdllda 241 aksvvralfi rekymalslq sfcpttrryl qqlaekplet rtyeqgpdtp vsadapvhpp 301 aleqhpyehc epstmpgdlg lglrmvrgvv hvytrrepde hcsevelpyp dlqefvadvn 361 vlmaliingp iksfcyrrlq ylsskfqmhv llnemkelaa qkkvphrdfy nirkvdthih 421 asscmnqkhl lrfikramkr hleeivhveq greqtlrevf esmnltaydl svdtldvhad 481 rntfhrfdkf nakynpiges vlreifiktd nrvsgkyfah iikevmsdle eskyqnaelr 541 lsiygrsrde wdklarwavm hrvhspnvrw lvqvprlfdv yrtkgqlanf qemleniflp 601 lfeatvhpas hpelhlfleh vdgfdsvdde skpenhvfnl esplpeawve ednppyayyl 661 yytfanmaml nhlrrqrgfh tfvlrphcge agpihhlvsa fmlaenishg lllrkapvlq 721 ylyylaqigi amsplsnnsl flsyhrnplp eylsrglmvs lstddplqfh ftkeplmeey
```

```
781 siatqvwkls scdmcelarn svlmsgfshk vkshwlgpny tkegpegndi rrtnvpdirv 841 gyryeticqe lalitqavqs emletipeea gitmspgpq
```

(NP_631895):

SEQ ID NO. 8

```
  1 maseargglg applqsarsl pgpapclkhf pldlrtsmdg kckeiaeelf trslaeselr 61 sapyefpees pieqleerrq rlerqisqdv klepdillra kqdflktdsd sdlqlykeqg 121 egqgdrslre rdvlerefqr vtisgeekcg vpftdlldaa ksvvralfir ekymalslqs 181 fcpttrrylq qlaekpletr tyeqgpdtpv sadapvhppa leqhpyehce pstmpgdlgl 241 glrmvrgvvh vytrrepdeh csevelpypd lqefvadvnv lmaliingpi ksfcyrrlqy 301 lsskfqmhvl lnemkelaaq kkvphrdfyn irkvdthiha sscmnqkhll rfikramkrh 361 leeivhveqg reqtlrevfe smnltaydls vdtldvhadr ntfhrfdkfn akynpigesv 421 lreifiktdn rvsgkyfahi ikevmsdlee skyqnaelrl siygrsrdew dklarwavmh 481 rvhspnvrwl vqvprlfdvy rtkgqlanfq emleniflpl featvhpash pelhlflehv 541 dgfdsvddes kpenhvfnle splpeawvee dnppyayyly ytfanmamln hlrrqrgfht 601 fvlrphcgea gpihhlvsaf mlaenishgl llrkapvlqy yylaqigia msplsnnslf 661 lsyhrnplpe ylsrglmvsl stddplqfhf tkeplmeeys iatqvwklss cdmcelarns 721 vlmsgfshkv kshwlgpnyt kegpegndir rtnvpdirvg yryetlcqel alitqavqse 781 mletipeeag itmspgpq
```

(NP_981949):

SEQ. ID NO. 9

```
  1 mltflpspqe lftrslaese lrsapyefpe espieqleer rqrlerqisq dvklepdill 61 rakqdflktd sdsdlqlyke qgegqgdrsl rerdvleref qrvtisgeek cgvpftdlld 121 aaksvvralf irekymalsl qsfcpttrry lqqlaekple trtyeqgpdt pvsadapvhp 181 paleqhpyeh cepstmpgdl glglrmvrgv vhvytrrepd ehcsevelpy pdlqefvadv 241 nvlmaliing piksfcyrrl qylsskfqmh vllnemkela aqkkvphrdf ynirkvdthi 301 hasscmnqkh llrfikramk rhleeivhve qgreqtlrev fesmnltayd lsvdtldvha 361 drntfhrfdk fnakynpige svlreifikt dnrvsgkyfa hiikevmsdl eeskyqnael 421 rlsiygrsrd ewdklarwav mhrvhspnvr wlvqvprlfd vyrtkgqlan fqemlenifl 481 plfeatvhpa shpelhlfle hvdgfdsvdd eskpenhvfn lesplpeawv eednppyayy 541 lyytfanmam lnhlrrqrgf htfvlrphcg eagpihhlvs afmlaenish glllrkapvl 601 qylyylaqig iamsplsnns lflsyhrnpl peylsrglmv slstddplqf hftkeplmee 661 ysiatqvwkl sscdmcelar nsvlmsgfsh kvkshwlgpn ytkegpegnd irrtnvpdir 721 vgyryetlcq elalitqavq semletipee agitmspgpq
```

(NP_001295099)

SEQ. ID NO. 10

```
  1 mwqsqapaga aqtpplsppw sqpwhpihla lasprpnipl rsgpacrppl qlqelftrsl 61 aeselrsapy efpeespieq leerrqrler qisqdvklep dillrakqdf lktdsdsdlq 121 lykeqgegqg drslrerdvl erefqrvtis geekcgvpft dlldaaksvv ralfirekym 181 alslqsfcpt trrylqqlae kpletrtyeq gpdtpvsada pvhppaleqh pyehcepstm 241 pgdlglglrm vrgvvhvytr repdehcsev elpypdlqef vadvnvlmal iingpiksfc 301 yrrlqylssk fqmhvllnem kelaaqkkvp hrdfynirkv dthihasscm nqkhllrfik 361 ramkrhleei vhveqgreqt lrevfesmnl taydlsvdtl dvhadrntfh rfdkfnakyn 421 pigesvlrei fiktdnrvsg kyfahiikev msdleeskyq naelrlsiyg rsrdewdkla 481 rwavmhrvhs pnvrwlvqvp rlfdvyrtkg qlanfqemle niflplfeat vhpashpelh
```

```
541 lflehvdgfd svddeskpen hvfnlesplp eawveednpp yayylyytfa nmamlnhlrr 601 qrgfhtfvlr phcgeagpih hlvsafmlae nishglllrk apvlqylyyl aqigiamspl 661 snnslflsyh rnplpeylsr glmvslstdd plqfhftkep lmeeysiatq vwklsscdmc 721 elarnsvlms gfshkvkshw lgpnytkegp egndirrtnv pdirvgyrye tlcqelalit 781 qavqsemlet ipeeagitms pgpq
```

(NP_001244290):                                                              SEQ. ID NO. 11
```
  1 mdgkckeiae elftrslaes elrsapyefp eespieqlee rrqrlerqis qdvklepdil 61 lrakqdflkt dsdsdlqlyk eqgegqgdrs lrerdvlere fqrvtisgee kcgvpftdll 121 daaksvvral firekymals lqsfcpttrr ylqqlaekpl etrtyeqgpd tpvsadapvh 181 ppaleqhpye hcepstmpgd lglglrmvrg vvhvytrrep dehcsevelp ypdlqefvad 241 vnvlmaliin gpiksfcyrr lqylsskfqm hvllnemkel aaqkkvphrd fynirkvdth 301 ihasscmnqk hllrfikram krhleeivhv eqgreqtlre vfesmnitay dlsvdtldvh 361 adrntfhrfd kfnakynpig esvlreifik tdnrvsgkyf ahiikevmsd leeskyqnae 421 lrlsiygrsr dewdklarwa vmhrvhspnv rwlvqvprlf dvyrtkgqla nfqemlenif 481 lplfeatvhp ashpelhlfl ehvdgfdsvd deskpenhvf nlesplpeaw veednppyay 541 ylyytfanma mlnhlrrqrg fhtfvlrphc geagpihhlv safmlaenis hglllrkapv 601 lqylyylaqi giamsplsnn slflsyhrnp lpeylsrglm vslstddplq fhftkeplme 661 eysiatqvwk lsscdmcela rnsvlmsgfs hkvkshwlgp nytkegpegn dirrtnvpdi 721 rvgyryetlc qelalitqav qsemletipe eagitmspgp q
```

(NP_001244289):                                                              SEQ. ID NO. 12
```
  1 mrnrgqglfr lrsrcflhqs lplgagrrkg ldvaepgpsr crsdspavaa wpamasyps 61 gsgkpkakyp fkkraslqas taapearggl gapplqsars lpgpapclkh fpldlrtsmd 121 gkckeiaeel ftrslaesel rsapyefpee spieqleerr qrlerqisqd vklepdillr 181 akqdflktds dsdlqlykeq gegqgdrslr erdvlerefq rvtisgeekc gvpftdllda 241 aksvvralfi rekymalslq sfcpttrryl qqlaekplet rtyeqgpdtp vsadapvhpp 301 aleqhpyehc epstmpgdlg lglrmvrgvv hvytrrepde hcsevelpyp dlqefvadvn 361 vlmaliingp iksfcyrrlq ylsskfqmhv llnemkelaa qkkvphrdfy nirkvdthih 421 asscmnqkhl lrfikramkr hleeivhveq greqtlrevf esmnltaydl svdtldvhad 481 rntfhrfdkf nakynpiges vlreifiktd nrvsgkyfah iikevmsdle eskyqnaelr 541 lsiygrsrde wdklarwavm hrvhspnvrw lvqvprlfdv yrtkgqlanf qemleniflp 601 lfeatvhpas hpelhlfleh vdgfdsvdde skpenhvfnl esplpeawve ednppyayyl 661 yytfanmaml nhlrrqrgfh tfvlrphcge agpihhlvsa fmlaenishg lllrkapvlq 721 ylyylaqigi amsplsnnsl flsyhrnplp eylsrglmvs lstddplqfh ftkeplmeey 781 siatqvwkls scdmcelarn svlmsgfshk vkshwlgpny tkegpegndi rrtnvpdirv 841 gryetlcqe lalitqavqs emletipeea gitmspgpq
```

---

What is claimed is:

1. A method for treating an AMPD2 related craving or addiction in a subject comprising administering a therapeutically effective amount of an AMPD2 inhibitor and/or a pan AMPD inhibitor, to the subject, wherein
   (a) the administering is done to decrease or treat a sugar, salt, or umami craving, or a combination thereof;
   (b) the administering is done to treat an addiction to alcohol, tobacco, nicotine, cocaine, methamphetamines, amphetamines and marijuana;
   (c) the administering is done to treat an addiction to opioids, cannabinoids, methylphenidate, phencyclidine, and substituted amphetamines, or sex; or
   (d) the administering is done to provide a diminished craving in the subject from at least one member selected from the group consisting of fructose, fructose-containing sugars, glucose, sucralose, and combinations thereof.

2. The method of claim 1, wherein the AMPD2 inhibitor comprises at least one member of the group consisting of a ribozyme, an interfering molecule, a peptide, a small molecule, an antibody targeted to at least AMPD2, and combinations thereof.

3. The method of claim 2, wherein the AMPD2 inhibitor comprises an interfering molecule, and wherein the interfering molecule comprises a member from the group consisting of a phosphothioate morpholino oligomer (PMO), miRNA, siRNA, methylated siRNA, treated-siRNA, shRNA, antisense RNA, a dicer-substrate 27-mer duplex, and any combination thereof.

4. The method of claim 1, wherein the subject is diabetic.

* * * * *

SEQUENCE LISTING

<160> NUMBER OF SEQ ID NOS: 12

<210> SEQ ID NO 1
<211> LENGTH: 4138

<212> TYPE: DNA
<213> ORGANISM: Homo sapiens

<400> SEQUENCE: 1

```
gcggggccag gcgggggcgg ggccaagggc cgcagagcct ggcgcggagc cggcgagatt      60
ttggtggggt ctcacctgtt gcgtgactcc cccacagtcc ggccgcggga gtccgaccct     120
gaatgcccag ggagtgttga gagaaatctg gacgagtttc gggtcccgct cccttgggag     180
cacgtggcct accagcctct cgattgcagg gttgggtggt cgcgacaccg gggtcgcctt     240
gaggccagtc cggctgccga ggtctgcggg agtccacctc cggccagctg caattttga     300
aagactgcct tactttcccc atctcagtgc cagggcaggg gcccttggag tgacttggct     360
ggggtctgtg gcccgatccc cctgccgtcc tcaggaccc gggctttctg ctgtacagac     420
ttctcgtggg cagcctcccc tcggaactcg ggcatcatgg cctcaggccc agccaccatc     480
agtcacgtca ctcctgggac tgaggaggca ggggagggat aaggggcaga gatggaggcc     540
ccactccccg aggttgccta gacaacatga gaaatcgtgg ccagggcctc ttccgcctgc     600
ggagccgctg cttcctgcat cagtcactcc cgctggggc ggggcggagg aagggggttgg    660
atgtggcaga gccaggcccc agccggtgcc gctcagactc cccgctgtc gccgccgtgg     720
tcccagccat ggcatcctat ccatctggct ctggcaagcc caaggccaaa tatccccttta    780
agaagcgggc cagcctgcag gcctccactg cagctccaga ggctcggggt ggtctggggg    840
ccccctccgct gcagtctgcc cgatccctgc cgggccccgc ccctgcctc aagcacttcc    900
cgctcgacct gcgcacgtct atggatggca aatgcaagga gatcgccgag gagctgttca    960
cccgctcact ggctgagagc gagctccgta gtgccccgta tgagttcccc gaggagagcc    1020
ccattgaaca gctggaggag cggcggcagc ggctggagcg gcagatcagc caggatgtca    1080
agctggagcc agacatcctg cttcgggcca agcaagattt cctgaagacg acagtgact     1140
cggacctaca gctctacaag gaacagggtg aggggcaggg tgaccggagc ctgcgggagc    1200
gtgatgtgct ggaacgggag tttcagcggg tcaccatctc tggggaggag aagtgtgggg    1260
tgccgttcac agacctgctg gatgcagcca agagtgtggt gcgggcgctc ttcatccggg    1320
agaagtacat ggccctgtcc ctgcagagct tctgccccac cacccgccgc tacctgcagc    1380
agctggctga aaagcctctg gagacccgga cctatgaaca gggcccccgac acccctgtgt    1440
ctgctgatgc cccggtgcac cccctgcgc tggagcagca cccgtatgag cactgtgagc    1500
caagcaccat gcctggggac ctgggcttgg gtctgcgcat ggtgcggggt gtggtgcacg    1560
tctacacccg cagggaaccc gacgagcatt gctcagaggt ggagctgcca tacctgacc     1620
tgcaggaatt tgtggctgac gtcaatgtgc tgatggccct gattatcaat ggcccccataa   1680
agtcattctg ctaccgccgg ctgcagtacc tgagctccaa gttccagatg catgtgctac    1740
tcaatgagat gaaggagctg gccgcccaga agaagtgcc acaccgagat ttctacaaca     1800
tccgcaaggt ggacacccac atccatgcct cgtcctgcat gaaccagaag catctgctgc    1860
gcttcatcaa gcgggcaatg aagcggcacc tggaggagat cgtgcacgtg agcagggcc     1920
gtgaacagac gctgcgggag gtctttgaga gcatgaatct cacggcctac gacctgagtg    1980
tggacacgct ggatgtgcat gcggacagga acactttcca tcgctttgac aagttttaatg   2040
ccaaatacaa ccctattggg gagtccgtcc tccgagagat cttcatcaag acggacaaca    2100
gggtatctgg gaagtacttt gctcacatca tcaaggagg gatgtcagac ctggaggaga    2160
gcaaatacca gaatgcagag ctgcggctct ccatttacgg gcgctcgagg gatgagtggg    2220
```

```
acaagctggc gcgctgggcc gtcatgcacc gcgtgcactc ccccaacgtg cgctggctgg    2280
tgcaggtgcc ccgcctcttt gatgtgtacc gtaccaaggg ccagctggcc aacttccagg    2340
agatgctgga gaacatcttc ctgccactgt tcgaggccac tgtgcaccct gccagccacc    2400
cggaactgca tctcttctta gagcacgtgg atggttttga cagcgtggat gatgagtcca    2460
agcctgaaaa ccatgtcttc aacctggaga gcccctgcc tgaggcgtgg gtggaggagg    2520
acaacccacc ctatgcctac tacctgtact acacctttgc caacatggcc atgttgaacc    2580
acctgcgcag gcagagggc ttccacacgt ttgtgctgag gccacactgt ggggaggctg    2640
ggcccatcca ccacctggtg tcagccttca tgctggctga aacatttcc cacgggctcc    2700
ttctgcgcaa ggccccgtc ctgcagtacc tgtactacct ggcccagatc ggcatcgcca    2760
tgtctccgct cagcaacaac agcctcttcc tcagctatca ccggaatccg ctaccggagt    2820
acctgtcccg cggcctcatg gtctccctgt ccactgatga tcccttgcag ttccacttca    2880
ccaaggagcc gctgatggag gagtacagca tcgccaccca ggtgtggaag ctcagctcct    2940
gcgatatgtg tgagctggcc cgcaacacg tgctcatgag cggcttctcg cacaaggtaa    3000
agagccactg gctgggaccc aactatacca aggaaggccc tgaggggaat gacatccgcc    3060
ggaccaatgt gccagacatc cgcgtgggct accgctacga gaccctgtgc caggagctgg    3120
cgctcatcac gcaggcagtc cagagtgaga tgctggagac cattccagag gaggcgggta    3180
tcaccatgag cccagggcct caatgagcct ggtccatgaa gtgcccacca catcgcagca    3240
ctttaccac gttttgtcct cagaccccgc ccatgctgtg tggtctctgc atgtctccat    3300
tcttctctgt ctctgtcttg catgtctcct accatgtcac tgtccctggg ccacccagtg    3360
aaagcaaagc ctgggaatct gctcattgtt gtttgggctc aggtattgag cctgatggcc    3420
caggtattga gggcctcccc tgctggtggc cctgtcctgg gatcctcaga agcctgactg    3480
tcctatgggc ttctccagtg tccacagggg cttgggatgg ttgtgggggg ctggcccctc    3540
tagccttttcc ggtccttcct gggcaaatct aagccttggc cagggccgaa gtttaggccc    3600
ctgtcttgtt catgtagccg aggggcaggc gggggacctc tacacctctg ctgtgggcac    3660
ggggctgctg agggtctgtg gaactccagc agctctgcac tgggtagagc tgggcctaga    3720
gctcagtcac aggcctgggc ttcctggcct gagtgggtag acgcaggcgg cagaggtgct    3780
ggaccacatc tccgccaagt cactgcccag cagccttctc cgtcctgtcc ccagcccacg    3840
tgctccttgg gtgtcagctt cctgtgcctc tgtgggagag ggcagctgcc ttgtgttatg    3900
tctggggcca cagttgctgc aaagtcctgg atctgccact caaccccggg agtggtgttc    3960
ccagtgtggc tcccagagct ttgaccagat tgtgatccca gctggcccct atgttgtgtt    4020
ctggactgag gcctttgctg tgaactgcag tgtttcatac gaaccatctt tcctagtgca    4080
tgagaaataa agattattta agtaatgaga aaaaaaaaa aaaaaaaaa aaaaaaa       4138
```

<210> SEQ ID NO 2
<211> LENGTH: 4005
<212> TYPE: DNA
<213> ORGANISM: Homo sapiens

<400> SEQUENCE: 2

```
gattctcggt tcttcccct cctcccagag ctgggctacc ccgggagctg agggtcagat      60
gtggaaggaa agtgggtgct gggttttcac ggagtatgcc tgccctgccc cgggaggact    120
gtgtttgagc ttggactcgc tcgctgctga attcctgttt gttattcttt tttcttccag    180
gctagctgga aggaccagct agcctggact ttggcttctt tgcccgggag ccctggcatg    240
```

```
atggggtgag ggctcttggt gggttagtgg agagctgggg gctggcccct ccccatcttc      300
ttttctaccc accccctccc cgcccccgc caggcccagc caccatcagt cacgtcactc        360
ctgggactga ggaggcaggg gagggataag gggcagagat ggaggcccca ctccccgagg      420
ttgcctagac aacatgagaa atcgtggcca gggcctcttc cgcctgcgga gccgctgctt      480
cctgcatcag tcactcccgc tggggcggg gcggaggaag gggttggatg tggcagagcc       540
aggcccagc cggtgccgct cagactcccc cgctgtcgcc gccgtggtcc cagccatggc       600
atcctatcca tctggctctg caagcccaa ggccaaatat cccttaaga agcgggccag        660
cctgcaggcc tccactgcag ctccagaggc tcggggtggt ctggggggcc ctccgctgca      720
gtctgcccga tccctgccgg gccccgcccc ctgcctcaag cacttcccgc tcgacctgcg      780
cacgtctatg gatggcaaat gcaaggagat cgccgaggag ctgttcaccc gctcactggc      840
tgagagcgag ctccgtagtg ccccgtatga gttccccgag gagagcccca ttgaacagct      900
ggaggagcgg cggcagcggc tggagcggca gatcagccag gatgtcaagc tggagccaga      960
catcctgctt cgggccaagc aagatttcct gaagacggac agtgactcgg acctacagct     1020
ctacaaggaa cagggtgagg ggcagggtga ccggagcctg cggagcgtg atgtgctgga      1080
acgggagttt cagcgggtca ccatctctgg ggaggagaag tgtggggtgc cgttcacaga     1140
cctgctggat gcagccaaga gtgtggtgcg ggcgctcttc atccgggaga agtacatggc     1200
cctgtccctg cagagcttct gccccaccac ccgccgctac ctgcagcagc tggctgaaaa     1260
gcctctggag acccggacct atgaacaggg ccccgacacc cctgtgtctg ctgatgcccc     1320
ggtgcaccc cctgcgctgg agcagcaccc gtatgagcac tgtgagccaa gcaccatgcc      1380
tggggacctg ggcttgggtc tgcgcatggt gcggggtgtg gtgcacgtct acacccgcag     1440
ggaacccgac gagcattgct cagaggtgga gctgccatac cctgacctgc aggaatttgt     1500
ggctgacgtc aatgtgctga tggccctgat tatcaatggc cccataaagt cattctgcta     1560
ccgccggctg cagtacctga gctccaagtt ccagatgcat gtgctactca atgagatgaa     1620
ggagctggcc gcccagaaga aagtgccaca ccgagatttc tacaacatcc gcaaggtgga     1680
cacccacatc catgcctcgt cctgcatgaa ccagaagcat ctgctgcgct tcatcaagcg     1740
ggcaatgaag cggcacctgg aggagatcgt gcacgtggag cagggccgtg aacagacgct     1800
gcgggaggtc tttgagagca tgaatctcac ggcctacgac ctgagtgtgg acacgctgga     1860
tgtgcatgcg gacaggaaca cttccatcg ctttgacaag tttaatgcca aatacaaccc      1920
tattggggag tccgtcctcc gagagatctt catcaagacg gacaacaggg tatctgggaa     1980
gtactttgct cacatcatca aggaggtgat gtcagacctg gaggagagca ataccagaa      2040
tgcagagctg cggctctcca tttacgggcg ctcgagggat gagtgggaca gctggcgcg      2100
ctgggccgtc atgcaccgcg tgcactcccc caacgtgcgc tggctggtgc aggtgccccg     2160
cctctttgat gtgtaccgta caagggcca gctggccaac ttccaggaga tgctggagaa      2220
catcttcctg ccactgttcg aggccactgt gcaccctgcc agccaccgg aactgcatct      2280
cttcttagag cacgtggatg gttttgacag cgtggatgat gagtccaagc ctgaaaacca     2340
tgtcttcaac ctggagagcc ccctgcctga ggcgtgggtg gaggaggaca cccacccta      2400
tgcctactac ctgtactaca cctttgccaa catggccatg ttgaaccacc tgcgcaggca     2460
gaggggcttc cacacgtttg tgctgaggcc acactgtggg gaggctgggc catccacca     2520
cctggtgtca gccttcatgc tggctgagaa catttcccac gggctccttc tgcgcaaggc     2580
```

```
cccgtcctg cagtacctgt actacctggc ccagatcggc atcgccatgt ctccgctcag    2640
caacaacagc ctcttcctca gctatcaccg gaatccgcta ccggagtacc tgtcccgcgg    2700
cctcatggtc tccctgtcca ctgatgatcc cttgcagttc cacttcacca aggagccgct    2760
gatggaggag tacagcatcg ccacccaggt gtggaagctc agctcctgcg atatgtgtga    2820
gctggcccgc aacagcgtgc tcatgagcgg cttctcgcac aaggtaaaga gccactggct    2880
gggacccaac tataccaagg aaggccctga ggggaatgac atccgccgga ccaatgtgcc    2940
agacatccgc gtgggctacc gctacgagac cctgtgccag gagctggcgc tcatcacgca    3000
ggcagtccag agtgagatgc tggagaccat tccagaggag gcgggtatca ccatgagccc    3060
agggcctcaa tgagcctggt ccatgaagtg cccaccacat cgcagcactt ttaccacgtt    3120
ttgtcctcag accccgccca tgctgtgtgg tctctgcatg tctccattct tctctgtctc    3180
tgtcttgcat gtctcctacc atgtcactgt ccctgggcca cccagtgaaa gcaaagcctg    3240
ggaatctgct cattgttgtt tgggctcagg tattgagcct gatggcccag gtattgaggg    3300
cctcccctgc tggtggccct gtcctgggat cctcagaagc ctgactgtcc tatgggcttc    3360
tccagtgtcc acaggggctt gggatggttg tggggggctg cccctctag cctttccggt    3420 ccttcctggg caaatctaag ccttggccag ggccgaagtt taggccctg tcttgttcat    3480 gtagccgagg ggcaggcggg ggacctctac acctctgctg tgggcacggg gctgctgagg    3540
gtctgtggaa ctccagcagc tctgcactgg gtagagctgg gcctagagct cagtcacagg    3600
cctgggcttc ctggcctgag tgggtagacg caggcggcag aggtgctgga ccacatctcc    3660
gccaagtcac tgcccagcag ccttctccgt cctgtcccca gccacgtgc tccttgggtg    3720 tcagcttcct gtgcctctgt gggagagggc agctgccttg tgttatgtct ggggccacag    3780
ttgctgcaaa gtcctggatc tgccactcaa ccccgggagt ggtgttccca gtgtggctcc    3840
cagagctttg accagattgt gatcccagct ggcccctatg ttgtgttctg gactgaggcc    3900
tttgctgtga actgcagtgt tcatacgaa ccatctttcc tagtgcatga gaaataaaga    3960
ttatttaagt aatgagaaaa aaaaaaaaaa aaaaaaaaaa aaaaa             4005
```

<210> SEQ ID NO 3  
<211> LENGTH: 3785  
<212> TYPE: DNA  
<213> ORGANISM: Homo sapiens

<400> SEQUENCE: 3

```
gcggggccag gcgggggcgg ggccaagggc cgcagagcct ggcgcggagc cggcgagatt      60 ttggtgggt ctcacctgtt gcgtgactcc cccacagtcc ggccgcggga gtccgaccct     120
gaatgcccag ggagtgttga gagaaatctg gacgagtttc gggtcccgct cccttgggag     180
cacgtggcct accagcctct cgattgcagg gttgggtggt cgcgacaccg gggtcgcctt     240
gaggccagtc cggctgccga ggtctgcggg agtccacctc cggccagctg caattttga     300 aagactgcct tactttcccc atctcagtgc cagggcaggg gcccttggag tgacttggct     360
ggggtctgtg gcccgatccc cctgccgtcc ctcaggaccc gggctttctg ctgtacagac     420
ttctcgtggg cagcctcccc tcggaactcg ggcatcatgg cctcagaggc tcggggtggt     480
ctggggcccc ctccgctgca gtctgcccga tccctgccgg gccccgcccc ctgcctcaag     540
cacttcccgc tcgacctgcg cacgtctatg gatggcaaat gcaaggagat cgccgaggag     600
ctgttcaccc gctcactggc tgagagcgag ctccgtagtg cccgtatga gttccccgag     660 gagagcccca ttgaacagct ggaggagcgg cggcagcggc tggagcggca gatcagccag     720
```

```
gatgtcaagc tggagccaga catcctgctt cgggccaagc aagatttcct gaagacggac      780
agtgactcgg acctacagct ctacaaggaa cagggtgagg ggcagggtga ccggagcctg      840
cgggagcgtg atgtgctgga acgggagttt cagcgggtca ccatctctgg ggaggagaag      900
tgtggggtgc cgttcacaga cctgctggat gcagccaaga gtgtggtgcg ggcgctcttc      960
atccgggaga agtacatggc cctgtccctg cagagcttct gccccaccac ccgccgctac     1020
ctgcagcagc tggctgaaaa gcctctggag acccggacct atgaacaggg ccccgacacc     1080
cctgtgtctg ctgatgcccc ggtgcacccc cctgcgctgg agcagcaccc gtatgagcac     1140
tgtgagccaa gcaccatgcc tggggacctg ggcttgggtc tgcgcatggt gcggggtgtg     1200
gtgcacgtct acacccgcag ggaacccgac gagcattgct cagaggtgga gctgccatac     1260
cctgacctgc aggaatttgt ggctgacgtc aatgtgctga tggccctgat tatcaatggc     1320
cccataaagt cattctgcta ccgccggctg cagtacctga gctccaagtt ccagatgcat     1380
gtgctactca atgagatgaa ggagctgccc gcccagaaga agtgccacac cgagatttc     1440 tacaacatcc gcaaggtgga cacccacatc catgcctcgt cctgcatgaa ccagaagcat     1500
ctgctgcgct tcatcaagcg ggcaatgaag cggcacctgg aggagatcgt gcacgtggag     1560
cagggccgtg aacagacgct gcgggaggtc tttgagagca tgaatctcac ggcctacgac     1620
ctgagtgtgg acacgctgga tgtgcatgcg gacaggaaca cttteccatcg ctttgacaag     1680 tttaatgcca aatacaaccc tattggggag tccgtcctcc gagagatctt catcaagacg     1740
gacaacaggg tatctgggaa gtactttgct cacatcatca aggaggtgat gtcagacctg     1800
gaggagagca aataccagaa tgcagagctg cggctctcca tttacgggcg ctcgagggat     1860
gagtgggaca agctggcgcg ctgggccgtc atgcaccgcg tgcactcccc caacgtgcgc     1920
tggctggtgc aggtgccccg cctctttgat gtgtaccgta ccaagggcca gctggccaac     1980
ttccaggaga tgctggagaa catcttcctg ccactgttcg aggccactgt gcaccctgcc     2040
agccacccgg aactgcatct cttcttagag cacgtggatg ttttgacag cgtggatgat     2100 gagtccaagc ctgaaaaacca tgtcttcaac ctggagagcc ccctgcctga ggcgtgggtg     2160
gaggaggaca acccacccta tgcctactac ctgtactaca cctttgccaa catggccatg     2220
ttgaaccacc tgcgcaggca gaggggcttc cacacgtttg tgctgaggcc acactgtggg     2280
gaggctgggc ccatccacca cctggtgtca gccttcatgc tggctgagaa catttcccac     2340
gggctccttc tgcgcaaggc ccccgtcctg cagtacctgt actacctggc ccagatcggc     2400
atcgccatgt ctccgctcag caacaacagc ctcttcctca gctatcaccg gaatccgcta     2460
ccggagtacc tgtcccgcgg cctcatggtc tccctgtcca ctgatgatcc cttgcagttc     2520
cacttcacca aggagccgct gatggaggag tacagcatcg ccacccaggt gtggaagctc     2580
agctcctgcg atatgtgtga gctggcccgc aacagcgtgc tcatgagcgg cttctcgcac     2640
aaggtaaaga gccactggct gggacccaac tataccaagg aaggccctga ggggaatgac     2700
atccgccgga ccaatgtgcc agacatccgc gtgggctacc gctacgagac cctgtgccag     2760
gagctggcgc tcatcacgca ggcagtccag agtgagatgc tggagaccat tccagaggag     2820
gcgggtatca ccatgagccc agggcctcaa tgagcctggt ccatgaagtg cccaccacat     2880
cgcagcactt ttaccacgtt ttgtcctcag accccgccca tgctgtgtgg tctctgcatg     2940
tctccattct tctctgtctc tgtcttgcat gtctcctacc atgtcactgt ccctgggcca     3000
cccagtgaaa gcaaagcctg ggaatctgct cattgttgtt tgggctcagg tattgagcct     3060
```

```
gatggcccag gtattgaggg cctcccctgc tggtggccct gtcctgggat cctcagaagc      3120
ctgactgtcc tatgggcttc tccagtgtcc acaggggctt gggatggttg tgggggggctg    3180 gcccctctag cctttccggt ccttcctggg caaatctaag ccttggccag ggccgaagtt     3240
taggcccctg tcttgttcat gtagccgagg ggcaggcggg ggacctctac acctctgctg    3300
tgggcacggg gctgctgagg gtctgtggaa ctccagcagc tctgcactgg gtagagctgg    3360
gcctagagct cagtcacagg cctgggcttc ctggcctgag tgggtagacg caggcggcag    3420
aggtgctgga ccacatctcc gccaagtcac tgcccagcag ccttctccgt cctgtcccca    3480
gcccacgtgc tccttgggtg tcagcttcct gtgcctctgt gggagagggc agctgccttg    3540
tgttatgtct ggggccacag ttgctgcaaa gtcctggatc tgccactcaa ccccgggagt    3600
ggtgttccca gtgtggctcc cagagctttg accagattgt gatcccagct ggcccctatg    3660
ttgtgttctg gactgaggcc tttgctgtga actgcagtgt ttcatacgaa ccatctttcc    3720
tagtgcatga gaaataaaga ttatttaagt aatgagaaaa aaaaaaaaaa aaaaaaaaa     3780 aaaaa                                                                 3785

<210> SEQ ID NO 4
<211> LENGTH: 3423
<212> TYPE: DNA
<213> ORGANISM: Homo sapiens

<400> SEQUENCE: 4
cgccgaggta tcacctggca ccacccgcac cctcaccccg tgtctccatg ccctgcctct       60
gctccccaca cccctcacct caagctgtcc cctcacctca cgcttggctg tctcctgatc      120
ctcagcctct cccaggtacc cctggtcctg ctgccctcac ccatccccag gactctgtag      180
gagagtgccc gagggcggag ggccagccat gctgaccttc cttccctccc ccaggagct      240 gttcacccgc tcactggctg agagcgagct ccgtagtgcc ccgtatgagt tccccgagga      300
gagccccatt gaacagctgg aggagcggcg gcagcggctg gagcggcaga tcagccagga     360
tgtcaagctg gagccagaca tcctgcttcg ggccaagcaa gatttcctga agacggacag     420
tgactcggac ctacagctct acaaggaaca gggtgagggg cagggtgacc ggagcctgcg     480
ggagcgtgat gtgctggaac gggagtttca gcgggtcacc atctctgggg aggagaagtg    540
tggggtgccg ttcacagacc tgctggatgc agccaagagt gtggtgcggg cgctcttcat     600
ccgggagaag tacatggccc tgtccctgca gagcttctgc ccaccaccc gccgctacct     660 gcagcagctg gctgaaaagc ctctggagac ccggacctat gaacagggcc ccgacacccc    720
tgtgtctgct gatgccccgg tgcaccccc tgcgctggag cagcacccgt atgagcactg    780
tgagccaagc accatgcctg ggacctggg cttgggtctg cgcatggtgc ggggtgtggt     840
gcacgtctac acccgcaggg aacccgacga gcattgctca gaggtggagc tgccataccc    900
tgacctgcag gaatttgtgg ctgacgtcaa tgtgctgatg ccctgattta tcaatggccc     960
cataaagtca ttctgctacc gccggctgca gtacctgagc tccaagttcc agatgcatgt    1020
gctactcaat gagatgaagg agctggccgc ccagaagaaa gtgccacacc gagatttcta    1080
caacatccgc aaggtggaca cccacatcca tgcctcgtcc tgcatgaacc agaagcatct    1140
gctgcgcttc atcaagcggg caatgaagcg gcacctggag gagatcgtgc acgtggagca    1200
gggccgtgaa cagacgctgc gggaggtctt tgagagcatg aatctcacgg cctacgacct    1260
gagtgtggac acgctggatg tgcatgcgga caggaacact ttccatcgct ttgacaagtt    1320
taatgccaaa tacaacccta ttggggagtc cgtcctccga gagatcttca tcaagacgga    1380
```

```
caacagggta tctgggaagt actttgctca catcatcaag gaggtgatgt cagacctgga   1440
ggagagcaaa taccagaatg cagagctgcg gctctccatt tacgggcgct cgagggatga   1500
gtgggacaag ctggcgcgct gggccgtcat gcaccgcgtg cactccccca acgtgcgctg   1560
gctggtgcag gtgccccgcc tctttgatgt gtaccgtacc aagggccagc tggccaactt   1620
ccaggagatg ctggagaaca tcttcctgcc actgttcgag gccactgtgc accctgccag   1680
ccaccccgga actgcatctct tcttagagca cgtggatggt tttgacagcg tggatgatga   1740
gtccaagcct gaaaaccatg tcttcaacct ggagagcccc ctgcctgagg cgtgggtgga   1800
ggaggacaac ccaccctatg cctactacct gtactacacc tttgccaaca tggccatgtt   1860
gaaccacctg cgcaggcaga ggggcttcca cacgtttgtg ctgaggccac actgtgggga   1920
ggctgggccc atccaccacc tggtgtcagc cttcatgctg gctgagaaca tttcccacgg   1980
gctccttctg cgcaaggccc ccgtcctgca gtacctgtac tacctggccc agatcggcat   2040
cgccatgtct ccgctcagca acaacagcct cttcctcagc tatcaccgga atccgctacc   2100
ggagtacctg tcccgcggcc tcatggtctc cctgtccact gatgatccct gcagttcca   2160 cttcaccaag gagccgctga tggaggagta cagcatcgcc acccaggtgt ggaagctcag   2220
ctcctgcgat atgtgtgagc tggcccgcaa cagcgtgctc atgagcggct ctcgcacaa   2280 ggtaaagagc cactggctgg gacccaacta taccaaggaa ggccctgagg ggaatgacat   2340
ccgccggacc aatgtgccag acatccgcgt gggctaccgc tacgagaccc tgtgccagga   2400
gctggcgctc atcacgcagg cagtccgag tgagatgctg gagaccattc cagaggaggc   2460
gggtatcacc atgagcccag ggcctcaatg agcctggtcc atgaagtgcc caccacatcg   2520
cagcactttt accacgtttt gtcctcagac cccgcccatg ctgtgtggtc tctgcatgtc   2580
tccattcttc tctgtctctg tcttgcatgt ctcctaccat gtcactgtcc ctgggccacc   2640
cagtgaaagc aaagcctggg aatctgctca ttgttgttg ggctcaggta ttgagcctga   2700
tgccccaggt attgagggcc tccctgctg gtggccctgt cctgggatcc tcagaagcct   2760
gactgtccta tgggcttctc cagtgtccac agggcttgg gatggttgtg ggggctggc   2820 ccctctagcc tttccggtcc ttcctgggca aatctaagcc ttggcaggg ccgaagttta   2880 ggcccctgtc ttgttcatgt agccgagggg caggcggggg acctctacac ctctgctgtg   2940
ggcacggggc tgctgagggt ctgtggaact ccagcagctc tgcactgggt agagctggc   3000 ctagagctca gtcacaggcc tgggcttcct ggcctgagtg ggtagacgca ggcggcagag   3060
gtgctggacc acatctccgc caagtcactg cccagcagcc ttctccgtcc tgtcccagc   3120 ccacgtgctc cttgggtgtc agcttcctgt gcctctgtgg gagagggcag ctgccttgtg   3180
ttatgtctgg ggccacagtt gctgcaaagt cctggatctg ccactcaacc ccgggagtgg   3240
tgttcccagt gtggctccca gagctttgac cagattgtga tcccagctgg ccctatgtt   3300 gtgttctgga ctgaggcctt tgctgtgaac tgcagtgttt catacgaacc atctttccta   3360
gtgcatgaga aataaagatt atttaagtaa tgagaaaaaa aaaaaaaaaa aaaaaaaaa   3420 aaa                                                                 3423
```

<210> SEQ ID NO 5
<211> LENGTH: 3421
<212> TYPE: DNA
<213> ORGANISM: Homo sapiens

<400> SEQUENCE: 5

-continued

| | | |
|---|---|---|
| gtacagcctg tgccagcccc tgagggaccg gctgcagctt cactggcaaa caggcgggca | 60 | |
| aggggcacag ggctgctggc cggagctgcc tgcactctgc agaggctcgg ggtggtctgg | 120 | |
| gggcccctcc gctgcagtct gcccgatccc tgccgggccc cgcccccctgc ctcaagcact | 180 | |
| tcccgctcga cctgcgcacg tctatggatg caaatgcaa ggagatcgcc gaggagctgt | 240 | |
| tcacccgctc actggctgag agcgagctcc gtagtgcccc gtatgagttc cccgaggaga | 300 | |
| gccccattga acagctggag gagcggcggc agcggctgga gcggcagatc agccaggatg | 360 | |
| tcaagctgga gccagacatc ctgcttcggg ccaagcaaga tttcctgaag acggacagtg | 420 | |
| actcggacct acagctctac aaggaacagg gtgaggggca gggtgaccgg agcctgcggg | 480 | |
| agcgtgatgt gctggaacgg gagtttcagc gggtcaccat ctctggggag gagaagtgtg | 540 | |
| gggtgccgtt cacagacctg ctggatgcag ccaagagtgt ggtgcgggcg ctcttcatcc | 600 | |
| gggagaagta catggccctg tccctgcaga gcttctgccc caccaccgc cgctacctgc | 660 | |
| agcagctggc tgaaaagcct ctggagaccc ggacctatga acaggcccc gacacccctg | 720 | |
| tgtctgctga tgccccggtg cacccccctg cgctggagca gcaccgtat gagcactgtg | 780 | |
| agccaagcac catgcctggg gacctgggct tgggtctgcg catggtgcgg ggtgtggtgc | 840 | |
| acgtctacac ccgcagggaa cccgacgagc attgctcaga ggtggagctg ccataccctg | 900 | |
| acctgcagga atttgtggct gacgtcaatg tgctgatggc cctgattatc aatggcccca | 960 | |
| taaagtcatt ctgctaccgc cggctgcagt acctgagctc caagttccag atgcatgtgc | 1020 | |
| tactcaatga gatgaaggag ctggccgccc agaagaaagt gccacaccga gatttctaca | 1080 | |
| acatccgcaa ggtggacacc cacatccatg cctcgtcctg catgaaccag aagcatctgc | 1140 | |
| tgcgcttcat caagcgggca atgaagcggc acctggagga gatcgtgcac gtggagcagg | 1200 | |
| gccgtgaaca cgactgcgg gaggtctttg agagcatgaa tctcacggcc tacgacctga | 1260 | |
| gtgtggacac gctggatgtg catgcggaca ggaacacttt ccatcgcttt gacaagttta | 1320 | |
| atgccaaata caaccctatt ggggagtccg tcctccgaga gatcttcatc aagacggaca | 1380 | |
| acagggtatc tgggaagtac tttgctcaca tcatcaagga ggtgatgtca gacctggagg | 1440 | |
| agagcaaata ccagaatgca gagctgcggc tctccatttta cgggcgctcg agggatgagt | 1500 | |
| gggacaagct ggcgcgctgg gccgtcatgc accgcgtgca ctcccccaac gtgcgctggc | 1560 | |
| tggtgcaggt gccccgcctc tttgatgtgt accgtaccaa gggccagctg gccaacttcc | 1620 | |
| aggagatgct ggagaacatc ttcctgccac tgttcgaggc cactgtgcac cctgccagcc | 1680 | |
| acccggaact gcatctcttc ttagagcacg tggatggttt tgacagcgtg gatgatgagt | 1740 | |
| ccaagcctga aaaccatgtc ttcaacctgg agagcccct gctgaggcg tgggtggagg | 1800 | |
| aggcaacccc accctatgcc tactacctgt actacaccctt tgccaacatg gccatgttga | 1860 | |
| accacctgcg caggcagagg ggcttccaca cgtttgtgct gaggccacac tgtggggagg | 1920 | |
| ctgggcccat ccaccacctg gtgtcagcct tcatgctggc tgagaacatt tcccacgggc | 1980 | |
| tccttctgcg caaggccccc gtcctgcagt acctgtacta cctggcccag atcggcatcg | 2040 | |
| ccatgtctcc gctcagcaac aacagcctct tcctcagcta tcaccggaat ccgctaccgg | 2100 | |
| agtacctgtc ccgcggcctc atggtctccc tgtccactga tgatccctg cagttccact | 2160 | |
| tcaccaagga gccgctgatg gaggagtaca gcatcgccac ccaggtgtgg aagctcagct | 2220 | |
| cctgcgatat gtgtgagctg gccgcaacaa gcgtgctcat gagcggcttc tcgcacaagg | 2280 | |
| taaagagcca ctggctggga cccaactata ccaaggaagg ccctgagggg aatgacatcc | 2340 | |
| gccggaccaa tgtgccagac atccgcgtgg gctaccgcta cgagaccctg tgccaggagc | 2400 | |

```
tggcgctcat cacgcaggca gtccagagtg agatgctgga gaccattcca gaggaggcgg    2460
gtatcaccat gagcccaggg cctcaatgag cctggtccat gaagtgccca ccacatcgca    2520
gcacttttac cacgttttgt cctcagaccc cgcccatgct gtgtggtctc tgcatgtctc    2580
cattcttctc tgtctctgtc ttgcatgtct cctaccatgt cactgtccct gggccaccca    2640
gtgaaagcaa agcctgggaa tctgctcatt gttgtttggg ctcaggtatt gagcctgatg    2700
gcccaggtat tgagggcctc ccctgctggt ggccctgtcc tgggatcctc agaagcctga    2760
ctgtcctatg ggcttctcca gtgtccacag gggcttggga tggttgtggg gggctggccc    2820
ctctagcctt tccggtcctt cctgggcaaa tctaagcctt ggccagggcc gaagtttagg    2880
cccctgtctt gttcatgtag ccgaggggca ggcgggggac ctctacacct ctgctgtggg    2940
cacggggctg ctgagggtct gtggaactcc agcagtctg cactgggtag agctgggcct     3000
agagctcagt cacaggcctg ggcttcctgg cctgagtggg tagacgcagg cggcagaggt    3060
gctggaccac atctccgcca agtcactgcc agcagcctt ctccgtcctg tccccagccc     3120
acgtgctcct tgggtgtcag cttcctgtgc ctctgtggga gagggcagct gccttgtgtt    3180
atgtctgggg ccacagttgc tgcaaagtcc tggatctgcc actcaacccc gggagtggtg    3240
ttcccagtgt ggctcccaga gctttgacca gattgtgatc ccagctggcc cctatgttgt    3300
gttctggact gaggcctttg ctgtgaactg cagtgtttca tacgaaccat ctttcctagt    3360
gcatgagaaa taagattat ttaagtaatg agaaaaaaaa aaaaaaaaa aaaaaaaaa       3420 a                                                                   3421

<210> SEQ ID NO 6
<211> LENGTH: 3541
<212> TYPE: DNA
<213> ORGANISM: Homo sapiens

<400> SEQUENCE: 6
gcccagccac catcagtcac gtcactcctg ggactgagga ggcaggggag ggataagggg      60
cagagatgga ggccccactc cccgaggttg cctagacaac atgagaaatc gtggccaggg     120
cctcttccgc ctgcggagcc gctgcttcct gcatcagtca ctcccgctgg gggcggggcg     180
gaggaagggg ttggatgtgg cagagccagg ccccagccgg tgccgctcag actccccgc     240 tgtcgccgcc gtggtcccag ccatggcatc ctatccatct ggctctggca agcccaaggc     300
caaatatccc tttaagaagc gggccagcct gcaggcctcc actgcagctc caggagctgt     360
tcacccgctc actggctgag agcgagctcc gtagtgcccc gtatgagttc cccgaggaga     420
gccccattga acagctggag gagcggcggc agcggctgga gcggcagatc agccaggatg     480
tcaagctgga gccagacatc ctgcttcggg ccaagcaaga tttcctgaag acggacagtg     540
actcggacct acagctctac aaggaacagg gtgaggggca gggtgaccgg agcctgcggg     600
agcgtgatgt gctggaacgg gagtttcagc gggtcaccat ctctggggag agaagtgtg     660 gggtgccgtt cacagacctg ctggatgcag ccaagagtgt ggtgcgggcg ctcttcatcc     720
gggagaagta catggccctg tccctgcaga gcttctgccc caccacccgc cgctacctgc     780
agcagctggc tgaaaagcct ctggagaccc ggacctatga acagggcccc gacacccctg     840
tgtctgctga tgccccggtg cacccccctg cgctggagca gcaccgtat gagcactgtg      900 agccaagcac catgcctggg gacctgggct tgggtctgcg catggtgcgg ggtgtggtgc     960
acgtctacac ccgcagggaa cccgacgagc attgctcaga ggtggagctg ccatacccctg   1020
```

| | | | | |
|---|---|---|---|---|
| acctgcagga | atttgtggct | gacgtcaatg | tgctgatggc | cctgattatc | aatggcccca | 1080 |
| taaagtcatt | ctgctaccgc | cggctgcagt | acctgagctc | caagttccag | atgcatgtgc | 1140 |
| tactcaatga | gatgaaggag | ctggccgccc | agaagaaagt | gccacaccga | gatttctaca | 1200 |
| acatccgcaa | ggtggacacc | cacatccatg | cctcgtcctg | catgaaccag | aagcatctgc | 1260 |
| tgcgcttcat | caagcgggca | atgaagcggc | acctggagga | gatcgtgcac | gtggagcagg | 1320 |
| gccgtgaaca | gacgctgcgg | gaggtctttg | agagcatgaa | tctcacggcc | tacgacctga | 1380 |
| gtgtggacac | gctggatgtg | catgcggaca | ggaacacttt | ccatcgcttt | gacaagttta | 1440 |
| atgccaaata | caaccctatt | ggggagtccg | tcctccgaga | gatcttcatc | aagacggaca | 1500 |
| acagggtatc | tggaagtac | tttgctcaca | tcatcaagga | ggtgatgtca | gacctggagg | 1560 |
| agagcaaata | ccagaatgca | gagctgcggc | tctccattta | cgggcgctcg | agggatgagt | 1620 |
| gggacaagct | ggcgcgctgg | gccgtcatgc | accgcgtgca | ctcccccaac | gtgcgctggc | 1680 |
| tggtgcaggt | gccccgcctc | tttgatgtgt | accgtaccaa | gggccagctg | gccaacttcc | 1740 |
| aggagatgct | ggagaacatc | ttcctgccac | tgttcgaggc | cactgtgcac | cctgccagcc | 1800 |
| acccggaact | gcatctcttc | ttagagcacg | tggatggttt | tgacagcgtg | gatgatgagt | 1860 |
| ccaagcctga | aaaccatgtc | ttcaacctgg | agagccccct | gcctgaggcg | tgggtggagg | 1920 |
| aggacaaccc | accctatgcc | tactacctgt | actacacctt | tgccaacatg | gccatgttga | 1980 |
| accacctgcg | caggcagagg | ggcttccaca | cgtttgtgct | gaggccacac | tgtgggggagg | 2040 |
| ctgggcccat | ccaccacctg | gtgtcagcct | tcatgctggc | tgagaacatt | tcccacgggc | 2100 |
| tccttctgcg | caaggccccc | gtcctgcagt | acctgtacta | cctggcccag | atcggcatcg | 2160 |
| ccatgtctcc | gctcagcaac | aacagcctct | tcctcagcta | tcaccggaat | ccgctaccgg | 2220 |
| agtacctgtc | ccgcggcctc | atggtctccc | tgtccactga | tgatcccttg | cagttccact | 2280 |
| tcaccaagga | gccgctgatg | gaggagtaca | gcatcgccac | ccaggtgtgg | aagctcagct | 2340 |
| cctgcgatat | gtgtgagctg | gcccgcaaca | gcgtgctcat | gagcggcttc | tcgcacaagg | 2400 |
| taaagagcca | ctggctggga | cccaactata | ccaaggaagg | ccctgagggg | aatgacatcc | 2460 |
| gccggaccaa | tgtgccagac | atccgcgtgg | gctaccgcta | cgagaccctg | tgccaggagc | 2520 |
| tggcgctcat | cacgcaggca | gtccagagtg | agatgctgga | gaccattcca | gaggaggcgg | 2580 |
| gtatcaccat | gagcccaggg | cctcaatgag | cctggtccat | gaagtgccca | ccacatcgca | 2640 |
| gcactttac | cacgttttgt | cctcagaccc | cgcccatgct | gtgtggtctc | tgcatgtctc | 2700 |
| cattcttctc | tgtctctgtc | ttgcatgtct | cctaccatgt | cactgtccct | gggccaccca | 2760 |
| gtgaaagcaa | agcctgggaa | tctgctcatt | gttgtttggg | ctcaggtatt | gagcctgatg | 2820 |
| gcccaggtat | tgagggcctc | ccctgctggt | ggccctgtcc | tgggatcctc | agaagcctga | 2880 |
| ctgtcctatg | ggcttctcca | gtgtccacag | gggcttggga | tggttgtggg | gggctggccc | 2940 |
| ctctagcctt | tccggtcctt | cctgggcaaa | tctaagcctt | ggccagggcc | gaagtttagg | 3000 |
| cccctgtctt | gttcatgtag | ccgaggggca | ggcggggac | ctctacacct | ctgctgtggg | 3060 |
| cacggggctg | ctgagggtct | gtggaactcc | agcagctctg | cactgggtag | agctgggcct | 3120 |
| agagctcagt | cacaggcctg | ggcttcctgg | cctgagtggg | tagacgcagg | cggcagaggt | 3180 |
| gctggaccac | atctccgcca | agtcactgcc | cagcagcctt | ctccgtcctg | tccccagccc | 3240 |
| acgtgctcct | tgggtgtcag | cttcctgtgc | ctctgtggga | gagggcagct | gccttgtgtt | 3300 |
| atgtctgggg | ccacagttgc | tgcaaagtcc | tggatctgcc | actcaacccc | gggagtggtg | 3360 |
| ttcccagtgt | ggctcccaga | gctttgacca | gattgtgatc | ccagctggcc | cctatgttgt | 3420 |

-continued

```
gttctggact gaggcctttg ctgtgaactg cagtgtttca tacgaaccat ctttcctagt    3480
gcatgagaaa taaagattat ttaagtaatg agaaaaaaaa aaaaaaaaaa aaaaaaaaa     3540 a                                                                    3541
```

<210> SEQ ID NO 7
<211> LENGTH: 879
<212> TYPE: PRT
<213> ORGANISM: Homo sapiens

<400> SEQUENCE: 7

Met Arg Asn Arg Gly Gln Gly Leu Phe Arg Leu Arg Ser Arg Cys Phe
1               5                   10                  15

Leu His Gln Ser Leu Pro Leu Gly Ala Gly Arg Arg Lys Gly Leu Asp
            20                  25                  30

Val Ala Glu Pro Gly Pro Ser Arg Cys Arg Ser Asp Ser Pro Ala Val
        35                  40                  45

Ala Ala Val Val Pro Ala Met Ala Ser Tyr Pro Ser Gly Ser Gly Lys
    50                  55                  60

Pro Lys Ala Lys Tyr Pro Phe Lys Lys Arg Ala Ser Leu Gln Ala Ser
65                  70                  75                  80

Thr Ala Ala Pro Glu Ala Arg Gly Gly Leu Gly Ala Pro Pro Leu Gln
                85                  90                  95

Ser Ala Arg Ser Leu Pro Gly Pro Ala Pro Cys Leu Lys His Phe Pro
            100                 105                 110

Leu Asp Leu Arg Thr Ser Met Asp Gly Lys Cys Lys Glu Ile Ala Glu
        115                 120                 125

Glu Leu Phe Thr Arg Ser Leu Ala Glu Ser Glu Leu Arg Ser Ala Pro
    130                 135                 140

Tyr Glu Phe Pro Glu Glu Ser Pro Ile Glu Gln Leu Glu Glu Arg Arg
145                 150                 155                 160

Gln Arg Leu Glu Arg Gln Ile Ser Gln Asp Val Lys Leu Glu Pro Asp
                165                 170                 175

Ile Leu Leu Arg Ala Lys Gln Asp Phe Leu Lys Thr Asp Ser Asp Ser
            180                 185                 190

Asp Leu Gln Leu Tyr Lys Glu Gln Gly Glu Gly Gln Gly Asp Arg Ser
        195                 200                 205

Leu Arg Glu Arg Asp Val Leu Glu Arg Glu Phe Gln Arg Val Thr Ile
    210                 215                 220

Ser Gly Glu Glu Lys Cys Gly Val Pro Phe Thr Asp Leu Leu Asp Ala
225                 230                 235                 240

Ala Lys Ser Val Val Arg Ala Leu Phe Ile Arg Glu Lys Tyr Met Ala
                245                 250                 255

Leu Ser Leu Gln Ser Phe Cys Pro Thr Thr Arg Arg Tyr Leu Gln Gln
            260                 265                 270

Leu Ala Glu Lys Pro Leu Glu Thr Arg Thr Tyr Glu Gln Gly Pro Asp
        275                 280                 285

Thr Pro Val Ser Ala Asp Ala Pro Val His Pro Ala Leu Glu Gln
    290                 295                 300

His Pro Tyr Glu His Cys Glu Pro Ser Thr Met Pro Gly Asp Leu Gly
305                 310                 315                 320

Leu Gly Leu Arg Met Val Arg Gly Val Val His Val Tyr Thr Arg Arg
                325                 330                 335

Glu Pro Asp Glu His Cys Ser Glu Val Glu Leu Pro Tyr Pro Asp Leu

-continued

```
                340             345             350
Gln Glu Phe Val Ala Asp Val Asn Val Leu Met Ala Leu Ile Ile Asn
            355                 360                 365
Gly Pro Ile Lys Ser Phe Cys Tyr Arg Arg Leu Gln Tyr Leu Ser Ser
        370                 375                 380
Lys Phe Gln Met His Val Leu Leu Asn Glu Met Lys Glu Leu Ala Ala
385                 390                 395                 400
Gln Lys Lys Val Pro His Arg Asp Phe Tyr Asn Ile Arg Lys Val Asp
                405                 410                 415
Thr His Ile His Ala Ser Ser Cys Met Asn Gln Lys His Leu Leu Arg
            420                 425                 430
Phe Ile Lys Arg Ala Met Lys Arg His Leu Glu Glu Ile Val His Val
        435                 440                 445
Glu Gln Gly Arg Glu Gln Thr Leu Arg Glu Val Phe Glu Ser Met Asn
        450                 455                 460
Leu Thr Ala Tyr Asp Leu Ser Val Asp Thr Leu Asp Val His Ala Asp
465                 470                 475                 480
Arg Asn Thr Phe His Arg Phe Asp Lys Phe Asn Ala Lys Tyr Asn Pro
                485                 490                 495
Ile Gly Glu Ser Val Leu Arg Glu Ile Phe Ile Lys Thr Asp Asn Arg
            500                 505                 510
Val Ser Gly Lys Tyr Phe Ala His Ile Ile Lys Glu Val Met Ser Asp
        515                 520                 525
Leu Glu Glu Ser Lys Tyr Gln Asn Ala Glu Leu Arg Leu Ser Ile Tyr
        530                 535                 540
Gly Arg Ser Arg Asp Glu Trp Asp Lys Leu Ala Arg Trp Ala Val Met
545                 550                 555                 560
His Arg Val His Ser Pro Asn Val Arg Trp Leu Val Gln Val Pro Arg
                565                 570                 575
Leu Phe Asp Val Tyr Arg Thr Lys Gly Gln Leu Ala Asn Phe Gln Glu
            580                 585                 590
Met Leu Glu Asn Ile Phe Leu Pro Leu Phe Glu Ala Thr Val His Pro
        595                 600                 605
Ala Ser His Pro Glu Leu His Leu Phe Leu Glu His Val Asp Gly Phe
        610                 615                 620
Asp Ser Val Asp Asp Glu Ser Lys Pro Glu Asn His Val Phe Asn Leu
625                 630                 635                 640
Glu Ser Pro Leu Pro Glu Ala Trp Val Glu Glu Asp Asn Pro Pro Tyr
                645                 650                 655
Ala Tyr Tyr Leu Tyr Tyr Thr Phe Ala Asn Met Ala Met Leu Asn His
            660                 665                 670
Leu Arg Arg Gln Arg Gly Phe His Thr Phe Val Leu Arg Pro His Cys
        675                 680                 685
Gly Glu Ala Gly Pro Ile His His Leu Val Ser Ala Phe Met Leu Ala
        690                 695                 700
Glu Asn Ile Ser His Gly Leu Leu Leu Arg Lys Ala Pro Val Leu Gln
705                 710                 715                 720
Tyr Leu Tyr Tyr Leu Ala Gln Ile Gly Ile Ala Met Ser Pro Leu Ser
                725                 730                 735
Asn Asn Ser Leu Phe Leu Ser Tyr His Arg Asn Pro Leu Pro Glu Tyr
            740                 745                 750
Leu Ser Arg Gly Leu Met Val Ser Leu Ser Thr Asp Asp Pro Leu Gln
        755                 760                 765
```

```
Phe His Phe Thr Lys Glu Pro Leu Met Glu Glu Tyr Ser Ile Ala Thr
        770                 775                 780

Gln Val Trp Lys Leu Ser Ser Cys Asp Met Cys Glu Leu Ala Arg Asn
785                 790                 795                 800

Ser Val Leu Met Ser Gly Phe Ser His Lys Val Lys Ser His Trp Leu
                805                 810                 815

Gly Pro Asn Tyr Thr Lys Glu Gly Pro Glu Gly Asn Asp Ile Arg Arg
            820                 825                 830

Thr Asn Val Pro Asp Ile Arg Val Gly Tyr Arg Tyr Glu Thr Leu Cys
        835                 840                 845

Gln Glu Leu Ala Leu Ile Thr Gln Ala Val Gln Ser Glu Met Leu Glu
    850                 855                 860

Thr Ile Pro Glu Glu Ala Gly Ile Thr Met Ser Pro Gly Pro Gln
865                 870                 875

<210> SEQ ID NO 8
<211> LENGTH: 798
<212> TYPE: PRT
<213> ORGANISM: Homo sapiens

<400> SEQUENCE: 8

Met Ala Ser Glu Ala Arg Gly Gly Leu Gly Ala Pro Pro Leu Gln Ser
1               5                   10                  15

Ala Arg Ser Leu Pro Gly Pro Ala Pro Cys Leu Lys His Phe Pro Leu
                20                  25                  30

Asp Leu Arg Thr Ser Met Asp Gly Lys Cys Lys Glu Ile Ala Glu Glu
            35                  40                  45

Leu Phe Thr Arg Ser Leu Ala Glu Ser Glu Leu Arg Ser Ala Pro Tyr
        50                  55                  60

Glu Phe Pro Glu Glu Ser Pro Ile Glu Gln Leu Glu Glu Arg Arg Gln
65                  70                  75                  80

Arg Leu Glu Arg Gln Ile Ser Gln Asp Val Lys Leu Glu Pro Asp Ile
                85                  90                  95

Leu Leu Arg Ala Lys Gln Asp Phe Leu Lys Thr Asp Ser Asp Ser Asp
                100                 105                 110

Leu Gln Leu Tyr Lys Glu Gln Gly Glu Gly Gln Gly Asp Arg Ser Leu
            115                 120                 125

Arg Glu Arg Asp Val Leu Glu Arg Glu Phe Gln Arg Val Thr Ile Ser
        130                 135                 140

Gly Glu Glu Lys Cys Gly Val Pro Phe Thr Asp Leu Leu Asp Ala Ala
145                 150                 155                 160

Lys Ser Val Val Arg Ala Leu Phe Ile Arg Glu Lys Tyr Met Ala Leu
                165                 170                 175

Ser Leu Gln Ser Phe Cys Pro Thr Thr Arg Arg Tyr Leu Gln Gln Leu
                180                 185                 190

Ala Glu Lys Pro Leu Glu Thr Arg Thr Tyr Gln Gly Pro Asp Thr
            195                 200                 205

Pro Val Ser Ala Asp Ala Pro Val His Pro Ala Leu Glu Gln His
    210                 215                 220

Pro Tyr Glu His Cys Glu Pro Ser Thr Met Pro Gly Asp Leu Gly Leu
225                 230                 235                 240

Gly Leu Arg Met Val Arg Gly Val Val His Val Tyr Thr Arg Arg Glu
                245                 250                 255

Pro Asp Glu His Cys Ser Glu Val Glu Leu Pro Tyr Pro Asp Leu Gln
```

-continued

```
                260                 265                 270
Glu Phe Val Ala Asp Val Asn Val Leu Met Ala Leu Ile Ile Asn Gly
            275                 280                 285
Pro Ile Lys Ser Phe Cys Tyr Arg Arg Leu Gln Tyr Leu Ser Ser Lys
        290                 295                 300
Phe Gln Met His Val Leu Leu Asn Glu Met Lys Glu Leu Ala Ala Gln
305                 310                 315                 320
Lys Lys Val Pro His Arg Asp Phe Tyr Asn Ile Arg Lys Val Asp Thr
                325                 330                 335
His Ile His Ala Ser Ser Cys Met Asn Gln Lys His Leu Leu Arg Phe
            340                 345                 350
Ile Lys Arg Ala Met Lys Arg His Leu Glu Glu Ile Val His Val Glu
        355                 360                 365
Gln Gly Arg Glu Gln Thr Leu Arg Glu Val Phe Glu Ser Met Asn Leu
    370                 375                 380
Thr Ala Tyr Asp Leu Ser Val Asp Thr Leu Asp Val His Ala Asp Arg
385                 390                 395                 400
Asn Thr Phe His Arg Phe Asp Lys Phe Asn Ala Lys Tyr Asn Pro Ile
                405                 410                 415
Gly Glu Ser Val Leu Arg Glu Ile Phe Ile Lys Thr Asp Asn Arg Val
            420                 425                 430
Ser Gly Lys Tyr Phe Ala His Ile Ile Lys Glu Val Met Ser Asp Leu
        435                 440                 445
Glu Glu Ser Lys Tyr Gln Asn Ala Glu Leu Arg Leu Ser Ile Tyr Gly
    450                 455                 460
Arg Ser Arg Asp Glu Trp Asp Lys Leu Ala Arg Trp Ala Val Met His
465                 470                 475                 480
Arg Val His Ser Pro Asn Val Arg Trp Leu Val Gln Val Pro Arg Leu
                485                 490                 495
Phe Asp Val Tyr Arg Thr Lys Gly Gln Leu Ala Asn Phe Gln Glu Met
            500                 505                 510
Leu Glu Asn Ile Phe Leu Pro Leu Phe Glu Ala Thr Val His Pro Ala
        515                 520                 525
Ser His Pro Glu Leu His Leu Phe Leu Glu His Val Asp Gly Phe Asp
    530                 535                 540
Ser Val Asp Asp Glu Ser Lys Pro Glu Asn His Val Phe Asn Leu Glu
545                 550                 555                 560
Ser Pro Leu Pro Glu Ala Trp Val Glu Glu Asp Asn Pro Pro Tyr Ala
                565                 570                 575
Tyr Tyr Leu Tyr Tyr Thr Phe Ala Asn Met Ala Met Leu Asn His Leu
            580                 585                 590
Arg Arg Gln Arg Gly Phe His Thr Phe Val Leu Arg Pro His Cys Gly
        595                 600                 605
Glu Ala Gly Pro Ile His His Leu Val Ser Ala Phe Met Leu Ala Glu
    610                 615                 620
Asn Ile Ser His Gly Leu Leu Leu Arg Lys Ala Pro Val Leu Gln Tyr
625                 630                 635                 640
Leu Tyr Tyr Leu Ala Gln Ile Gly Ile Ala Met Ser Pro Leu Ser Asn
                645                 650                 655
Asn Ser Leu Phe Leu Ser Tyr His Arg Asn Pro Leu Pro Glu Tyr Leu
            660                 665                 670
Ser Arg Gly Leu Met Val Ser Leu Ser Thr Asp Asp Pro Leu Gln Phe
        675                 680                 685
```

```
His Phe Thr Lys Glu Pro Leu Met Glu Glu Tyr Ser Ile Ala Thr Gln
            690                 695                 700

Val Trp Lys Leu Ser Ser Cys Asp Met Cys Glu Leu Ala Arg Asn Ser
705                 710                 715                 720

Val Leu Met Ser Gly Phe Ser His Lys Val Lys Ser His Trp Leu Gly
                725                 730                 735

Pro Asn Tyr Thr Lys Glu Gly Pro Glu Gly Asn Asp Ile Arg Arg Thr
                740                 745                 750

Asn Val Pro Asp Ile Arg Val Gly Tyr Arg Tyr Glu Thr Leu Cys Gln
                755                 760                 765

Glu Leu Ala Leu Ile Thr Gln Ala Val Gln Ser Glu Met Leu Glu Thr
        770                 775                 780

Ile Pro Glu Glu Ala Gly Ile Thr Met Ser Pro Gly Pro Gln
785                 790                 795

<210> SEQ ID NO 9
<211> LENGTH: 760
<212> TYPE: PRT
<213> ORGANISM: Homo sapiens

<400> SEQUENCE: 9

Met Leu Thr Phe Leu Pro Ser Pro Gln Glu Leu Phe Thr Arg Ser Leu
1               5                   10                  15

Ala Glu Ser Glu Leu Arg Ser Ala Pro Tyr Glu Phe Pro Glu Glu Ser
            20                  25                  30

Pro Ile Glu Gln Leu Glu Glu Arg Arg Gln Arg Leu Glu Arg Gln Ile
        35                  40                  45

Ser Gln Asp Val Lys Leu Glu Pro Asp Ile Leu Leu Arg Ala Lys Gln
    50                  55                  60

Asp Phe Leu Lys Thr Asp Ser Asp Ser Asp Leu Gln Leu Tyr Lys Glu
65                  70                  75                  80

Gln Gly Glu Gly Gln Gly Asp Arg Ser Leu Arg Glu Arg Asp Val Leu
                85                  90                  95

Glu Arg Glu Phe Gln Arg Val Thr Ile Ser Gly Glu Glu Lys Cys Gly
            100                 105                 110

Val Pro Phe Thr Asp Leu Leu Asp Ala Ala Lys Ser Val Val Arg Ala
        115                 120                 125

Leu Phe Ile Arg Glu Lys Tyr Met Ala Leu Ser Leu Gln Ser Phe Cys
    130                 135                 140

Pro Thr Thr Arg Arg Tyr Leu Gln Gln Leu Ala Glu Lys Pro Leu Glu
145                 150                 155                 160

Thr Arg Thr Tyr Glu Gln Gly Pro Asp Thr Pro Val Ser Ala Asp Ala
                165                 170                 175

Pro Val His Pro Pro Ala Leu Glu Gln His Pro Tyr Glu His Cys Glu
            180                 185                 190

Pro Ser Thr Met Pro Gly Asp Leu Gly Leu Gly Leu Arg Met Val Arg
        195                 200                 205

Gly Val Val His Val Tyr Thr Arg Arg Glu Pro Asp Glu His Cys Ser
    210                 215                 220

Glu Val Glu Leu Pro Tyr Pro Asp Leu Gln Glu Phe Val Ala Asp Val
225                 230                 235                 240

Asn Val Leu Met Ala Leu Ile Ile Asn Gly Pro Ile Lys Ser Phe Cys
                245                 250                 255

Tyr Arg Arg Leu Gln Tyr Leu Ser Ser Lys Phe Gln Met His Val Leu
```

```
                260                 265                 270
Leu Asn Glu Met Lys Glu Leu Ala Ala Gln Lys Lys Val Pro His Arg
        275                 280                 285

Asp Phe Tyr Asn Ile Arg Lys Val Asp Thr His Ile His Ala Ser Ser
        290                 295                 300

Cys Met Asn Gln Lys His Leu Leu Arg Phe Ile Lys Arg Ala Met Lys
305                 310                 315                 320

Arg His Leu Glu Glu Ile Val His Val Glu Gln Gly Arg Glu Gln Thr
                325                 330                 335

Leu Arg Glu Val Phe Glu Ser Met Asn Leu Thr Ala Tyr Asp Leu Ser
        340                 345                 350

Val Asp Thr Leu Asp Val His Ala Asp Arg Asn Thr Phe His Arg Phe
        355                 360                 365

Asp Lys Phe Asn Ala Lys Tyr Asn Pro Ile Gly Glu Ser Val Leu Arg
        370                 375                 380

Glu Ile Phe Ile Lys Thr Asp Asn Arg Val Ser Gly Lys Tyr Phe Ala
385                 390                 395                 400

His Ile Ile Lys Glu Val Met Ser Asp Leu Glu Glu Ser Lys Tyr Gln
                405                 410                 415

Asn Ala Glu Leu Arg Leu Ser Ile Tyr Gly Arg Ser Arg Asp Glu Trp
        420                 425                 430

Asp Lys Leu Ala Arg Trp Ala Val Met His Arg Val His Ser Pro Asn
        435                 440                 445

Val Arg Trp Leu Val Gln Val Pro Arg Leu Phe Asp Val Tyr Arg Thr
        450                 455                 460

Lys Gly Gln Leu Ala Asn Phe Gln Glu Met Leu Glu Asn Ile Phe Leu
465                 470                 475                 480

Pro Leu Phe Glu Ala Thr Val His Pro Ala Ser His Pro Glu Leu His
                485                 490                 495

Leu Phe Leu Glu His Val Asp Gly Phe Asp Ser Val Asp Asp Glu Ser
        500                 505                 510

Lys Pro Glu Asn His Val Phe Asn Leu Glu Ser Pro Leu Pro Glu Ala
        515                 520                 525

Trp Val Glu Glu Asp Asn Pro Pro Tyr Ala Tyr Tyr Leu Tyr Tyr Thr
        530                 535                 540

Phe Ala Asn Met Ala Met Leu Asn His Leu Arg Arg Gln Arg Gly Phe
545                 550                 555                 560

His Thr Phe Val Leu Arg Pro His Cys Gly Glu Ala Gly Pro Ile His
                565                 570                 575

His Leu Val Ser Ala Phe Met Leu Ala Glu Asn Ile Ser His Gly Leu
        580                 585                 590

Leu Leu Arg Lys Ala Pro Val Leu Gln Tyr Leu Tyr Tyr Leu Ala Gln
        595                 600                 605

Ile Gly Ile Ala Met Ser Pro Leu Ser Asn Asn Ser Leu Phe Leu Ser
        610                 615                 620

Tyr His Arg Asn Pro Leu Pro Glu Tyr Leu Ser Arg Gly Leu Met Val
625                 630                 635                 640

Ser Leu Ser Thr Asp Asp Pro Leu Gln Phe His Phe Thr Lys Glu Pro
                645                 650                 655

Leu Met Glu Glu Tyr Ser Ile Ala Thr Gln Val Trp Lys Leu Ser Ser
        660                 665                 670

Cys Asp Met Cys Glu Leu Ala Arg Asn Ser Val Leu Met Ser Gly Phe
        675                 680                 685
```

```
Ser His Lys Val Lys Ser His Trp Leu Gly Pro Asn Tyr Thr Lys Glu
690                 695                 700

Gly Pro Glu Gly Asn Asp Ile Arg Arg Thr Asn Val Pro Asp Ile Arg
705                 710                 715                 720

Val Gly Tyr Arg Tyr Glu Thr Leu Cys Gln Glu Leu Ala Leu Ile Thr
                725                 730                 735

Gln Ala Val Gln Ser Glu Met Leu Glu Thr Ile Pro Glu Ala Gly
            740                 745                 750

Ile Thr Met Ser Pro Gly Pro Gln
            755                 760

<210> SEQ ID NO 10
<211> LENGTH: 804
<212> TYPE: PRT
<213> ORGANISM: Homo sapiens

<400> SEQUENCE: 10

Met Trp Gln Ser Gln Ala Pro Ala Gly Ala Gln Thr Pro Pro Leu
1               5                   10                  15

Ser Pro Pro Trp Ser Gln Pro Trp His Pro Ile His Leu Ala Leu Ala
                20                  25                  30

Ser Pro Arg Pro Asn Ile Pro Leu Arg Ser Gly Pro Ala Cys Arg Pro
            35                  40                  45

Pro Leu Gln Leu Gln Glu Leu Phe Thr Arg Ser Leu Ala Glu Ser Glu
50                  55                  60

Leu Arg Ser Ala Pro Tyr Glu Phe Pro Glu Glu Ser Pro Ile Glu Gln
65                  70                  75                  80

Leu Glu Glu Arg Arg Gln Arg Leu Glu Arg Gln Ile Ser Gln Asp Val
                85                  90                  95

Lys Leu Glu Pro Asp Ile Leu Leu Arg Ala Lys Gln Asp Phe Leu Lys
                100                 105                 110

Thr Asp Ser Asp Ser Asp Leu Gln Leu Tyr Lys Glu Gln Gly Glu Gly
            115                 120                 125

Gln Gly Asp Arg Ser Leu Arg Glu Arg Asp Val Leu Glu Arg Glu Phe
130                 135                 140

Gln Arg Val Thr Ile Ser Gly Glu Lys Cys Gly Val Pro Phe Thr
145                 150                 155                 160

Asp Leu Leu Asp Ala Ala Lys Ser Val Val Arg Ala Leu Phe Ile Arg
                165                 170                 175

Glu Lys Tyr Met Ala Leu Ser Leu Gln Ser Phe Cys Pro Thr Thr Arg
            180                 185                 190

Arg Tyr Leu Gln Gln Leu Ala Glu Lys Pro Leu Glu Thr Arg Thr Tyr
        195                 200                 205

Glu Gln Gly Pro Asp Thr Pro Val Ser Ala Asp Ala Pro Val His Pro
210                 215                 220

Pro Ala Leu Glu Gln His Pro Tyr Glu His Cys Glu Pro Ser Thr Met
225                 230                 235                 240

Pro Gly Asp Leu Gly Leu Gly Leu Arg Met Val Arg Gly Val Val His
                245                 250                 255

Val Tyr Thr Arg Arg Glu Pro Asp Glu His Cys Ser Glu Val Glu Leu
            260                 265                 270

Pro Tyr Pro Asp Leu Gln Glu Phe Val Ala Asp Val Asn Val Leu Met
        275                 280                 285

Ala Leu Ile Ile Asn Gly Pro Ile Lys Ser Phe Cys Tyr Arg Arg Leu
```

```
            290                 295                 300
Gln Tyr Leu Ser Ser Lys Phe Gln Met His Val Leu Leu Asn Glu Met
305                 310                 315                 320

Lys Glu Leu Ala Ala Gln Lys Lys Val Pro His Arg Asp Phe Tyr Asn
                325                 330                 335

Ile Arg Lys Val Asp Thr His Ile His Ala Ser Ser Cys Met Asn Gln
                340                 345                 350

Lys His Leu Leu Arg Phe Ile Lys Arg Ala Met Lys Arg His Leu Glu
                355                 360                 365

Glu Ile Val His Val Glu Gln Gly Arg Glu Gln Thr Leu Arg Glu Val
            370                 375                 380

Phe Glu Ser Met Asn Leu Thr Ala Tyr Asp Leu Ser Val Asp Thr Leu
385                 390                 395                 400

Asp Val His Ala Asp Arg Asn Thr Phe His Arg Phe Asp Lys Phe Asn
                405                 410                 415

Ala Lys Tyr Asn Pro Ile Gly Glu Ser Val Leu Arg Glu Ile Phe Ile
                420                 425                 430

Lys Thr Asp Asn Arg Val Ser Gly Lys Tyr Phe Ala His Ile Ile Lys
                435                 440                 445

Glu Val Met Ser Asp Leu Glu Glu Ser Lys Tyr Gln Asn Ala Glu Leu
            450                 455                 460

Arg Leu Ser Ile Tyr Gly Arg Ser Arg Asp Glu Trp Asp Lys Leu Ala
465                 470                 475                 480

Arg Trp Ala Val Met His Arg Val His Ser Pro Asn Val Arg Trp Leu
                485                 490                 495

Val Gln Val Pro Arg Leu Phe Asp Val Tyr Arg Thr Lys Gly Gln Leu
                500                 505                 510

Ala Asn Phe Gln Glu Met Leu Glu Asn Ile Phe Leu Pro Leu Phe Glu
                515                 520                 525

Ala Thr Val His Pro Ala Ser His Pro Glu Leu His Leu Phe Leu Glu
            530                 535                 540

His Val Asp Gly Phe Asp Ser Val Asp Asp Glu Ser Lys Pro Glu Asn
545                 550                 555                 560

His Val Phe Asn Leu Glu Ser Pro Leu Pro Glu Ala Trp Val Glu Glu
                565                 570                 575

Asp Asn Pro Pro Tyr Ala Tyr Tyr Leu Tyr Tyr Thr Phe Ala Asn Met
                580                 585                 590

Ala Met Leu Asn His Leu Arg Arg Gln Arg Gly Phe His Thr Phe Val
                595                 600                 605

Leu Arg Pro His Cys Gly Glu Ala Gly Pro Ile His His Leu Val Ser
            610                 615                 620

Ala Phe Met Leu Ala Glu Asn Ile Ser His Gly Leu Leu Leu Arg Lys
625                 630                 635                 640

Ala Pro Val Leu Gln Tyr Leu Tyr Tyr Leu Ala Gln Ile Gly Ile Ala
                645                 650                 655

Met Ser Pro Leu Ser Asn Asn Ser Leu Phe Leu Ser Tyr His Arg Asn
                660                 665                 670

Pro Leu Pro Glu Tyr Leu Ser Arg Gly Leu Met Val Ser Leu Ser Thr
                675                 680                 685

Asp Asp Pro Leu Gln Phe His Phe Thr Lys Glu Pro Leu Met Glu Glu
            690                 695                 700

Tyr Ser Ile Ala Thr Gln Val Trp Lys Leu Ser Ser Cys Asp Met Cys
705                 710                 715                 720
```

```
Glu Leu Ala Arg Asn Ser Val Leu Met Ser Gly Phe Ser His Lys Val
                725                 730                 735

Lys Ser His Trp Leu Gly Pro Asn Tyr Thr Lys Glu Gly Pro Glu Gly
            740                 745                 750

Asn Asp Ile Arg Arg Thr Asn Val Pro Asp Ile Arg Val Gly Tyr Arg
        755                 760                 765

Tyr Glu Thr Leu Cys Gln Glu Leu Ala Leu Ile Thr Gln Ala Val Gln
    770                 775                 780

Ser Glu Met Leu Glu Thr Ile Pro Glu Glu Ala Gly Ile Thr Met Ser
785                 790                 795                 800

Pro Gly Pro Gln

<210> SEQ ID NO 11
<211> LENGTH: 761
<212> TYPE: PRT
<213> ORGANISM: Homo sapiens

<400> SEQUENCE: 11

Met Asp Gly Lys Cys Lys Glu Ile Ala Glu Glu Leu Phe Thr Arg Ser
1               5                   10                  15

Leu Ala Glu Ser Glu Leu Arg Ser Ala Pro Tyr Glu Phe Pro Glu Glu
            20                  25                  30

Ser Pro Ile Glu Gln Leu Glu Glu Arg Arg Gln Arg Leu Glu Arg Gln
        35                  40                  45

Ile Ser Gln Asp Val Lys Leu Glu Pro Asp Ile Leu Leu Arg Ala Lys
    50                  55                  60

Gln Asp Phe Leu Lys Thr Asp Ser Asp Ser Asp Leu Gln Leu Tyr Lys
65                  70                  75                  80

Glu Gln Gly Glu Gly Gln Gly Asp Arg Ser Leu Arg Glu Arg Asp Val
            85                  90                  95

Leu Glu Arg Glu Phe Gln Arg Val Thr Ile Ser Gly Leu Glu Lys Cys
        100                 105                 110

Gly Val Pro Phe Thr Asp Leu Leu Asp Ala Ala Lys Ser Val Val Arg
    115                 120                 125

Ala Leu Phe Ile Arg Glu Lys Tyr Met Ala Leu Ser Leu Gln Ser Phe
130                 135                 140

Cys Pro Thr Thr Arg Arg Tyr Leu Gln Gln Leu Ala Glu Lys Pro Leu
145                 150                 155                 160

Glu Thr Arg Thr Tyr Glu Gln Gly Pro Asp Thr Pro Val Ser Ala Asp
            165                 170                 175

Ala Pro Val His Pro Pro Ala Leu Glu Gln His Pro Tyr Glu His Cys
        180                 185                 190

Glu Pro Ser Thr Met Pro Gly Asp Leu Gly Leu Gly Leu Arg Met Val
    195                 200                 205

Arg Gly Val Val His Val Tyr Thr Arg Arg Glu Pro Asp Glu His Cys
210                 215                 220

Ser Glu Val Glu Leu Pro Tyr Pro Asp Leu Gln Glu Phe Val Ala Asp
225                 230                 235                 240

Val Asn Val Leu Met Ala Leu Ile Ile Asn Gly Pro Ile Lys Ser Phe
            245                 250                 255

Cys Tyr Arg Arg Leu Gln Tyr Leu Ser Ser Lys Phe Gln Met His Val
        260                 265                 270

Leu Leu Asn Glu Met Lys Glu Leu Ala Ala Gln Lys Lys Val Pro His
    275                 280                 285
```

```
Arg Asp Phe Tyr Asn Ile Arg Lys Val Asp Thr His Ile His Ala Ser
    290                 295                 300

Ser Cys Met Asn Gln Lys His Leu Leu Arg Phe Ile Lys Arg Ala Met
305                 310                 315                 320

Lys Arg His Leu Glu Glu Ile Val His Val Glu Gln Gly Arg Glu Gln
                325                 330                 335

Thr Leu Arg Glu Val Phe Glu Ser Met Asn Leu Thr Ala Tyr Asp Leu
                340                 345                 350

Ser Val Asp Thr Leu Asp Val His Ala Asp Arg Asn Thr Phe His Arg
            355                 360                 365

Phe Asp Lys Phe Asn Ala Lys Tyr Asn Pro Ile Gly Glu Ser Val Leu
    370                 375                 380

Arg Glu Ile Phe Ile Lys Thr Asp Asn Arg Val Ser Gly Lys Tyr Phe
385                 390                 395                 400

Ala His Ile Ile Lys Glu Val Met Ser Asp Leu Glu Glu Ser Lys Tyr
                405                 410                 415

Gln Asn Ala Glu Leu Arg Leu Ser Ile Tyr Gly Arg Ser Arg Asp Glu
                420                 425                 430

Trp Asp Lys Leu Ala Arg Trp Ala Val Met His Arg Val His Ser Pro
            435                 440                 445

Asn Val Arg Trp Leu Val Gln Val Pro Arg Leu Phe Asp Val Tyr Arg
    450                 455                 460

Thr Lys Gly Gln Leu Ala Asn Phe Gln Glu Met Leu Glu Asn Ile Phe
465                 470                 475                 480

Leu Pro Leu Phe Glu Ala Thr Val His Pro Ala Ser His Pro Glu Leu
                485                 490                 495

His Leu Phe Leu Glu His Val Asp Gly Phe Asp Ser Val Asp Asp Glu
                500                 505                 510

Ser Lys Pro Glu Asn His Val Phe Asn Leu Glu Ser Pro Leu Pro Glu
            515                 520                 525

Ala Trp Val Glu Glu Asp Asn Pro Tyr Ala Tyr Tyr Leu Tyr Tyr
            530                 535                 540

Thr Phe Ala Asn Met Ala Met Leu Asn His Leu Arg Arg Gln Arg Gly
545                 550                 555                 560

Phe His Thr Phe Val Leu Arg Pro His Cys Gly Glu Ala Gly Pro Ile
                565                 570                 575

His His Leu Val Ser Ala Phe Met Leu Ala Glu Asn Ile Ser His Gly
            580                 585                 590

Leu Leu Leu Arg Lys Ala Pro Val Leu Gln Tyr Leu Tyr Tyr Leu Ala
            595                 600                 605

Gln Ile Gly Ile Ala Met Ser Pro Leu Ser Asn Asn Ser Leu Phe Leu
    610                 615                 620

Ser Tyr His Arg Asn Pro Leu Pro Glu Tyr Leu Ser Arg Gly Leu Met
625                 630                 635                 640

Val Ser Leu Ser Thr Asp Asp Pro Leu Gln Phe His Phe Thr Lys Glu
                645                 650                 655

Pro Leu Met Glu Glu Tyr Ser Ile Ala Thr Gln Val Trp Lys Leu Ser
                660                 665                 670

Ser Cys Asp Met Cys Glu Leu Ala Arg Asn Ser Val Leu Met Ser Gly
            675                 680                 685

Phe Ser His Lys Val Lys Ser His Trp Leu Gly Pro Asn Tyr Thr Lys
    690                 695                 700
```

Glu Gly Pro Glu Gly Asn Asp Ile Arg Arg Thr Asn Val Pro Asp Ile
705                 710                 715                 720

Arg Val Gly Tyr Arg Tyr Glu Thr Leu Cys Gln Glu Leu Ala Leu Ile
            725                 730                 735

Thr Gln Ala Val Gln Ser Glu Met Leu Glu Thr Ile Pro Glu Glu Ala
        740                 745                 750

Gly Ile Thr Met Ser Pro Gly Pro Gln
        755                 760

<210> SEQ ID NO 12
<211> LENGTH: 879
<212> TYPE: PRT
<213> ORGANISM: Homo sapiens

<400> SEQUENCE: 12

Met Arg Asn Arg Gly Gln Gly Leu Phe Arg Leu Arg Ser Arg Cys Phe
1               5                   10                  15

Leu His Gln Ser Leu Pro Leu Gly Ala Gly Arg Arg Lys Gly Leu Asp
            20                  25                  30

Val Ala Glu Pro Gly Pro Ser Arg Cys Arg Ser Asp Ser Pro Ala Val
        35                  40                  45

Ala Ala Val Val Pro Ala Met Ala Ser Tyr Pro Ser Gly Ser Gly Lys
    50                  55                  60

Pro Lys Ala Lys Tyr Pro Phe Lys Lys Arg Ala Ser Leu Gln Ala Ser
65                  70                  75                  80

Thr Ala Ala Pro Glu Ala Arg Gly Gly Leu Gly Ala Pro Pro Leu Gln
                85                  90                  95

Ser Ala Arg Ser Leu Pro Gly Pro Ala Pro Cys Leu Lys His Phe Pro
            100                 105                 110

Leu Asp Leu Arg Thr Ser Met Asp Gly Lys Cys Lys Glu Ile Ala Glu
        115                 120                 125

Glu Leu Phe Thr Arg Ser Leu Ala Glu Ser Glu Leu Arg Ser Ala Pro
    130                 135                 140

Tyr Glu Phe Pro Glu Glu Ser Pro Ile Glu Gln Leu Glu Glu Arg Arg
145                 150                 155                 160

Gln Arg Leu Glu Arg Gln Ile Ser Gln Asp Val Lys Leu Glu Pro Asp
                165                 170                 175

Ile Leu Leu Arg Ala Lys Gln Asp Phe Leu Lys Thr Asp Ser Asp Ser
            180                 185                 190

Asp Leu Gln Leu Tyr Lys Glu Gln Gly Glu Gly Gln Gly Asp Arg Ser
        195                 200                 205

Leu Arg Glu Arg Asp Val Leu Glu Arg Glu Phe Gln Arg Val Thr Ile
    210                 215                 220

Ser Gly Glu Glu Lys Cys Gly Val Pro Phe Thr Asp Leu Leu Asp Ala
225                 230                 235                 240

Ala Lys Ser Val Val Arg Ala Leu Phe Ile Arg Glu Lys Tyr Met Ala
                245                 250                 255

Leu Ser Leu Gln Ser Phe Cys Pro Thr Thr Arg Arg Tyr Leu Gln Gln
            260                 265                 270

Leu Ala Glu Lys Pro Leu Glu Thr Arg Thr Tyr Glu Gln Gly Pro Asp
        275                 280                 285

Thr Pro Val Ser Ala Asp Ala Pro Val His Pro Ala Leu Glu Gln
    290                 295                 300

His Pro Tyr Glu His Cys Glu Pro Ser Thr Met Pro Gly Asp Leu Gly
305                 310                 315                 320

```
Leu Gly Leu Arg Met Val Arg Gly Val Val His Val Tyr Thr Arg Arg
                325                 330                 335

Glu Pro Asp Glu His Cys Ser Glu Val Glu Leu Pro Tyr Pro Asp Leu
            340                 345                 350

Gln Glu Phe Val Ala Asp Val Asn Val Leu Met Ala Leu Ile Ile Asn
        355                 360                 365

Gly Pro Ile Lys Ser Phe Cys Tyr Arg Arg Leu Gln Tyr Leu Ser Ser
    370                 375                 380

Lys Phe Gln Met His Val Leu Leu Asn Glu Met Lys Glu Leu Ala Ala
385                 390                 395                 400

Gln Lys Lys Val Pro His Arg Asp Phe Tyr Asn Ile Arg Lys Val Asp
                405                 410                 415

Thr His Ile His Ala Ser Ser Cys Met Asn Gln Lys His Leu Leu Arg
            420                 425                 430

Phe Ile Lys Arg Ala Met Lys Arg His Leu Glu Glu Ile Val His Val
        435                 440                 445

Glu Gln Gly Arg Glu Gln Thr Leu Arg Glu Val Phe Glu Ser Met Asn
    450                 455                 460

Leu Thr Ala Tyr Asp Leu Ser Val Asp Thr Leu Asp Val His Ala Asp
465                 470                 475                 480

Arg Asn Thr Phe His Arg Phe Asp Lys Phe Asn Ala Lys Tyr Asn Pro
                485                 490                 495

Ile Gly Glu Ser Val Leu Arg Glu Ile Phe Ile Lys Thr Asp Asn Arg
            500                 505                 510

Val Ser Gly Lys Tyr Phe Ala His Ile Ile Lys Glu Val Met Ser Asp
        515                 520                 525

Leu Glu Glu Ser Lys Tyr Gln Asn Ala Glu Leu Arg Leu Ser Ile Tyr
    530                 535                 540

Gly Arg Ser Arg Asp Glu Trp Asp Lys Leu Ala Arg Trp Ala Val Met
545                 550                 555                 560

His Arg Val His Ser Pro Asn Val Arg Trp Leu Val Gln Val Pro Arg
                565                 570                 575

Leu Phe Asp Val Tyr Arg Thr Lys Gly Gln Leu Ala Asn Phe Gln Glu
            580                 585                 590

Met Leu Glu Asn Ile Phe Leu Pro Leu Phe Glu Ala Thr Val His Pro
        595                 600                 605

Ala Ser His Pro Glu Leu His Leu Phe Leu Glu His Val Asp Gly Phe
    610                 615                 620

Asp Ser Val Asp Asp Glu Ser Lys Pro Glu Asn His Val Phe Asn Leu
625                 630                 635                 640

Glu Ser Pro Leu Pro Glu Ala Trp Val Glu Asp Asn Pro Pro Tyr
                645                 650                 655

Ala Tyr Tyr Leu Tyr Tyr Thr Phe Ala Asn Met Ala Met Leu Asn His
            660                 665                 670

Leu Arg Arg Gln Arg Gly Phe His Thr Phe Val Leu Arg Pro His Cys
        675                 680                 685

Gly Glu Ala Gly Pro Ile His His Leu Val Ser Ala Phe Met Leu Ala
    690                 695                 700

Glu Asn Ile Ser His Gly Leu Leu Leu Arg Lys Ala Pro Val Leu Gln
705                 710                 715                 720

Tyr Leu Tyr Tyr Leu Ala Gln Ile Gly Ile Ala Met Ser Pro Leu Ser
                725                 730                 735
```

-continued

```
Asn Asn Ser Leu Phe Leu Ser Tyr His Arg Asn Pro Leu Pro Glu Tyr
            740             745             750

Leu Ser Arg Gly Leu Met Val Ser Leu Ser Thr Asp Asp Pro Leu Gln
        755             760             765

Phe His Phe Thr Lys Glu Pro Leu Met Glu Glu Tyr Ser Ile Ala Thr
    770             775             780

Gln Val Trp Lys Leu Ser Ser Cys Asp Met Cys Glu Leu Ala Arg Asn
785             790             795                         800

Ser Val Leu Met Ser Gly Phe Ser His Lys Val Lys Ser His Trp Leu
            805             810             815

Gly Pro Asn Tyr Thr Lys Glu Gly Pro Glu Gly Asn Asp Ile Arg Arg
            820             825             830

Thr Asn Val Pro Asp Ile Arg Val Gly Tyr Arg Tyr Glu Thr Leu Cys
            835             840             845

Gln Glu Leu Ala Leu Ile Thr Gln Ala Val Gln Ser Glu Met Leu Glu
        850             855             860

Thr Ile Pro Glu Glu Ala Gly Ile Thr Met Ser Pro Gly Pro Gln
865             870             875
```